(12) United States Patent
Drewe et al.

(10) Patent No.: US 6,906,203 B1
(45) Date of Patent: Jun. 14, 2005

(54) SUBSTITUTED 4H-CHROMENE AND ANALOGS AS ACTIVATORS OF CASPASES AND INDUCERS OF APOPTOSIS AND THE USE THEREOF

(75) Inventors: John A. Drewe, Carlsbad, CA (US); Sui Xiong Cai, San Diego, CA (US); Yan Wang, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 09/705,840

(22) Filed: Nov. 6, 2000

Related U.S. Application Data

(60) Provisional application No. 60/185,211, filed on Feb. 24, 2000, and provisional application No. 60/163,584, filed on Nov. 5, 1999.

(51) Int. Cl.[7] ............................................. C07D 295/04
(52) U.S. Cl. ..................................................... 548/577
(58) Field of Search ................................ 548/577, 430; 514/411

(56) References Cited

U.S. PATENT DOCUMENTS

| | | | |
|---|---|---|---|
| 4,698,345 A | * 10/1987 | Dicker et al. | 514/291 |
| 5,281,619 A | 1/1994 | Dell et al. | 514/454 |

(Continued)

FOREIGN PATENT DOCUMENTS

| | | |
|---|---|---|
| EP | 0 537 949 A1 | 4/1993 |
| EP | 0 599 514 A2 | 6/1994 |
| EP | 0 618 206 A1 | 10/1994 |
| EP | 0 619 314 A1 | 10/1994 |
| WO | WO 96/20721 | 7/1996 |
| WO | WO 98/24427 | 6/1998 |
| WO | WO 99/18856 | 4/1999 |
| WO | WO 99/54286 A2 | 10/1999 |
| WO | WO 00/04901 | 2/2000 |
| WO | WO 02/092083 A1 | 11/2002 |
| WO | WO 02/092594 A1 | 11/2002 |
| WO | WO 03/096982 A2 | 11/2003 |
| WO | WO 03/097806 A2 | 11/2003 |

OTHER PUBLICATIONS

Steedman's Medical Dictionary, 27th Edition, Pugh, M.B., et al., eds., Lippincott Williams & Wilkins, Philadelphia, PA, p. 897, col. 1, line 28, through p. 898, col. 1, line 8 (Jan. 2000).

(Continued)

Primary Examiner—D. Margaret Seaman
Assistant Examiner—Binta Robinson
(74) Attorney, Agent, or Firm—Sterne, Kessler, Goldstein & Fox P.L.L.C.

(57) ABSTRACT

The present invention is directed to substituted 4H-chromene and analogs thereof, represented by the general Formula I:

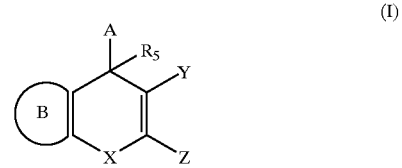

(I)

wherein A, B, X, Y, Z and $R_5$ are defined herein. The present invention also relates to the discovery that compounds having Formula I are activators of caspases and inducers of apoptosis. Therefore, the activators of caspases and inducers of apoptosis of this invention can be used to induce cell death in a variety of clinical conditions in which uncontrolled growth and spread of abnormal cells occurs.

27 Claims, 6 Drawing Sheets

U.S. PATENT DOCUMENTS

| | | | |
|---|---|---|---|
| 5,284,868 A | 2/1994 | Dell et al. | 514/454 |
| 5,434,160 A | 7/1995 | Dell et al. | 514/291 |
| 5,514,706 A | 5/1996 | Ambler et al. | 514/454 |
| 5,571,818 A | 11/1996 | Williams | 514/291 |
| 5,574,034 A | 11/1996 | Williams | 514/232.8 |
| 5,576,325 A | 11/1996 | Williams | 514/291 |
| 5,637,589 A | 6/1997 | Lee et al. | 514/291 |
| 5,726,204 A | 3/1998 | Lee et al. | 514/455 |
| 5,847,165 A | 12/1998 | Lee et al. | 549/280 |
| 6,160,010 A | 12/2000 | Uckun et al. | |
| 6,221,900 B1 | 4/2001 | Uckun et al. | |
| 6,258,824 B1 | 7/2001 | Yang | |
| 6,294,575 B1 | 9/2001 | Uckun et al. | |
| 6,303,652 B1 | 10/2001 | Uckun et al. | |
| 6,365,626 B1 | 4/2002 | Uckun et al. | |
| 6,388,092 B2 | 5/2002 | Yang | |
| 2003/0065018 A1 | 4/2003 | Cai et al. | |
| 2003/0114485 A1 | 6/2003 | Cai et al. | |

OTHER PUBLICATIONS

"Anti–inflammatory Agents" in the "Product Category Index" of the *Physician's Desk Reference*, 56th Edition, Medical Economics Company, Inc., Montvale, NJ, p. 206 (Nov. 2001).

*Steedman's Medical Dictionary*, 27th Edition, Pugh, M.B., et al., eds., Lippincott Williams & Wilkins, Philadelphia, PA, p. 276, col. 2, lines 57–63 (Jan. 2000).

"Antineoplastics,"In the"Product Category Index" of the *Physician's Desk Reference*, 56th Edition, Medical Economics Company, Inc., Montvale, NJ, p. 206 (Nov. 2001).

Bode, A., and Dong, Z., "Apoptosis induction by arsenic: mechanisms of action and possible clinical applications for treating therapy–resistant cancers," *Drug Resist. Update* 1:21–29, (Feb. 2000) PubMed, http://www/ncbi.nlm.nih.gov/entrez/query.fcgi?cmd=Retrieve&db=PubMed&list_uids=11 4.9.8 accessed on Nov. 5, 2002.

Ding, Z., et al., "Resistance to apoptosis is correlated with the reduced caspase–3 activation and enhanced expression of antiapoptotic proteins in human cervical multidrug–resistant cells," (Apr. 2000) PubMed, http://www/ncbi.nlm.nih.gov/entrez/query.fcgi?cmd=Retrieve&db=PubMed&list_uids=10 7.5.3 accessed on Nov. 5, 2002.

Norgaard, J.M., and Hokland, P., "Biology of multiple drug resistance in acute leukemia," *Int J. Hematol.* 72:290–297, (Oct. 2000) (see p. 290, seventh sentence), erratum 73:132 (Jan. 2001) PubMed, http://www/ncbi.nlm.nih.gov/entrez/query.fcgi?cmd=Retrieve&db=PubMed&list_uids=11 1.8.5 accessed on Nov. 5, 2002.

Barinaga, M., "Cell Suicide: By ICE, Not Fire," *Science* 263:754–756, American Association for the Advancement of Science (Feb. 1994).

Bloxham, J. et al., "Preparation of Some New Benzylidenemalononitriles by an $S_NAr$ Reaction: Application to Naphtho [1,2–b] pyran Synthesis," *Heterocycles* 38:399–408, Elsevier Science Publishers B.V. (Feb. 1994).

Chandrasekhar, S. et al., "Identification of a Novel Chemical Series That Blocks Interleukin–1–Stimulated Metalloprotease Activity in Chondrocytes," *J. Pharmacol. Exp. Ther.* 273: 1519–1528, Williams & Wilkins (1995).

McCarty, M.F., "Polyphenol–mediated inhibition of AP–1 transactivating activity may slow cancer growth by impeding angiogenesis and tumor invasiveness," *Medical Hypotheses* 50:511–514, Harcourt Brace & Co. Ltd. (May 1998).

Paull, K.D. et al., "Identification of Novel Antimitotic Agents Acting at the Tubulin Level by Computer–assisted Evaluation of Differential Cytotoxicity Data," *Cancer Res.* 52:3892–3900, American Association for Cancer Research (Jul. 1992).

Ruddon, R.W., "Biochemistry of Cancer," in *Holland Frei Cancer Medicine*, Fifth Edition, section 1, chapter 7, B.C. Decker, accessed Apr. 12, 2002 at <http://www.ncbi.nlm.nih.gov/books/bv.fcgi?call=bv.View . . ShowSection&rid=cmed. chapter.d>.

Salvesen, G.S. and Dixit, V.M., "Caspase activation: The induced–proximity model," *Proc. Natl. Acad. Sci. USA* 96:10964–10967, National Academy of Sciences of the United States of America (Sep. 1999).

Wolf, B.B., and Green, D.R., "Suidical Tendencies: Apoptotic Cell Death by Caspase Family Proteinases," *J. Biol. Chem.* 274:20049–20052, The American Society for Biochemistry and Molecular Biology, Inc. (Jul. 1999).

Ellis, R.E. et al., "Mechanisms and Functions of Cell Death," *Annu. Rev. Cell. Biol.* 7:663–698, Annual Reviews, Inc. (1991).

Friesen, C. et al., "Involvement of the CD95 (APO–1/Fas) receptor/ligand system in drug–induced apoptosis in leukemia cells," *Nature Med.* 2:574–577, Nature Publishing Group (1996).

Los, M. et al., "Cross–Resistance of CD95– and Drug–Induced Apoptosis as a Consequence of Deficient Activation of Caspases (ICE/Ced–3 Proteases)," *Blood* 90:3118–3129, The American Society of Hematology (1997).

Orrenius, S., "Apoptosis: molecular mechanisms and implications for human disease," J. Internal Med. 237:529–536, Blackwell Science Ltd. (1995).

Schmitt, E. et al., "The Bcl–xL and Bax–α control points: modulation of apoptosis induced by cancer chemotherapy and relation to TPCK–sensitive protease and caspase activation," *Biochem. Cell Biol.* 75:301–314, NRC Canada (1997).

Sharanin, Y.A. et al., "Synthesis of 2–amino–4H–chromenes," *Chem. Abstracts* 99:631, Abstract No. 212393z, American Chemical Society (1983).

Thornberry, N.A., "The caspase family of cysteine proteases," *Br. Med. Bull.* 53:478–490, The Royal Society of Medicine Press Limited (1997).

Thornberry, N.A., "Caspases: key mediators of apoptosis," *Chemistry & Biology* 5:R97–R103, Current Biology Ltd. (1998).

Wiernicki, T.R. et al., "Inhibition of Vascular Smooth Muscle Cell Proliferation and Arterial Intimal Thickening by a Novel Antiproliferative Naphthopyran," *J. Pharmacol. Exp. Ther.* 278:1452–1459, Williams & Wilkins (1996).

Wyllie, A.H., "Cell death: a new classification separating apoptosis from necrosis," in *Cell death in biology and pathology*, Bowen, I.D. and R.A. Lockshin, eds., Chapman and Hall, 1981, pp. 9–34.

Wyllie, A.H. et al., "Cell Death: The Significance of Apoptosis," *Intl. Rev. Cytol.* 68:251–306, Academic Press, Inc. (1980).

International Search Report for International Application No. PCT/US00/30374, mailed Jun. 15, 2001.

"aryl," *Hawley's Condensed Chemical Dictionary*, Thirteenth Edition, p. 94, John Wiley & Sons, Inc. (1997).

Al–Mousawi, S.M. et al., "Synthesis of New Condensed 2–Amino–4H–pyran–3–carbonitriles and of 2–Aminoquinoline–3–carbonitriles," *Organic Preparations and Procedures Int. 31*:305–313, Organic Preparations and Procedures Inc. (Jun. 1999).

Batteux, F. et al., "Gene Therapy of Experimental Autoimmuine Thyroiditis by In Vivo Administration of Plasmid DNA Coding for Fas Ligand," *J. Immunol. 162*:603–608, The American Association of Immunologists (Jan. 1999).

Birch, K.A. et al., "LY290181, an Inhibitor of Diabetes–Induced Vascular Dysfunction, Blocks Protein Kinase C–Stimulated Transcriptional Activation Through Inhibition of Transcription Factor Binding to a Phorbol Response Element," *Diabetes 45*:642–650, The American Diabetes Association (1996).

Boirivant, M. et al., "Lamina Propria T Cells in Crohn's Disease and Other Gastrointestinal Inflammation Show Defective CD2 Pathway–Induced Apoptosis," *Gastroenterology 116*:557–565, American Gastroenterological Association (Mar. 1999).

Coven, T.R. et al., "PUVA–induced lymphocyte apoptosis: Mechanism of action in psoriasis," *Photodermatol. Photoimmunol. Photomed. 15*:22–27, Munksgaard (Feb. 1999).

Elagamey, A.G.A. et al., "Nitriles in Heterocyclic Synthesis: Novel Synthesis of Benzo[b]pyrans, Naphtho[1,2–b]pyrans, Naphtho[2,1–b]pyrans, Pyrano[3,2–h]quinolines and Pyrano[3,2–C]quinolines," *Collection Czechoslovak Chem. Commun. 53*:1534–1538, Institute of Organic Chemistry and Biochemistry (1988).

Greenwald, R.B. et al., "Drug Delivery Systems Employing 1,4– or 1,6–Elimination: Poly(ethylene glycol) Prodrugs of Amine–Containing Compounds," *J. Med. Chem. 42*:3657–3667, American Chemical Society (Sep. 1999) (Published on Web, Aug. 13, 1999).

Heenen, M. et al., "Methotrexate induces apoptotic cell death in human keratinocytes," *Arch. Dermatol. Res. 290*:240–245, Springer–Verlag (May 1998).

Infante, A.J. et al., "The clinical spectrum in a large kindred with autoimmune lymphoproliferative syndrome caused by a Fas mutation that impairs lymphocyte apoptosis," *J. Pediatr. 133*:629–633, Mosby, Inc. (Nov. 1998).

Klokol, G.V. et al., "Cyclization of Nitriles. XXIII. Addition of Active Phenols to Electron–deficient Ethylenes, Accompanied by Cyclization to 2–Amino–4H–benzo[b]pyrans. Crystal Structure of 2–Amino–4–(2–fluorophenyl)–3–ethoxycarbonyl–4H–naphtho[2,1–b]pyran," *Zh. Org. Khim. 23*:412–421, Nauka, Leningradskoe otdelenie (1987).

Klokol, G.V. et al., "Cyclization of Nitriles. XXIII. Addition of Active Phenols to Electron–deficient Ethylenes, Accompanied by Cyclization to 2–Amino–4H–benzo[b]pyrans. Crystal Structure of 2–Amino–4–(2–fluorophenyl)–3–ethoxycarbonyl–4H–naphtho[2,1–b]pyran," *J. Org. Chem. USSR 23*:369–377 (1987).

Leu, Y.–L. et al., "Design and Synthesis of Water–Soluble Glucuronide Derivatives of Camptothecin for Cancer Prodrug Monotherapy and Antibody–Directed Enzyme Prodrug Therapy (ADEPT)," *J. Med. Chem. 42*:3623–3628, American Chemical Society (Sep. 1999) (Published on Web, Aug. 24, 1999).

López–Hoyos, M. et al., "Regulation of B cell apoptosis by Bcl–2 and Bcl–$X_L$ and its role in the development of autoimmune diseases (Review)," *Int. J. Mol. Med. 1*:475–483 (Feb. 1998).

O'Reilly, L.A. and Strasser, A., "Apoptosis and autoimmune disease," *Inflamm. Res. 48*:5–21, Birkhäuser Verlag (Jan. 1999).

Ohsako, S. and Elkon, K.B., "Apoptosis in the effector phase of autoimmune diabetes, multiple sclerosis and thyroiditis," *Cell Death Differ. 6*:13–21, Stockton Press (Jan. 1999).

Ozawa, M. et al., "312–nanometer Ultraviolet B Light (Narrow–Band UVB) Induces Apoptosis of T Cells within Psoriatic Lesions," *J. Exp. Med. 189*:711–718, The Rockefeller University Press (Feb. 1999).

Panda, D. et al., "Suppression of Microtubule Dynamics by LY290181. A Potential Mechanism for its Antiproliferative Action," *J. Biol. Chem. 272*:7681–7687, The American Society for Biochemistry and Molecular Biology, Inc. (1997).

Radwan, S.M. et al., "Synthesis and Some Reactions of New Benzo[B]pyran Derivatives," *Phsophorus. Sulfur. and Silicon 101*:297–211, Gordon and Breach Publishers (1995).

Savill, J., "Apoptosis in resolution of inflammation," *J. Leukoc. Biol. 61*:375–380, Society for Leukocyte Biology (1997).

Sharanin, Yu.A. and Klokol, G.V., "Synthesis of 2–Amino–4H–chromenes," *Zh. Org. Khim. 19*:1782–1784, Nauka, Leningradskoe otdelenie (1983).

Sharanin, Yu.A. and Klokol, G.V., "Synthesis of 2–Amino–4H–chromenes," *J. Org. Chem. USSR 19*:1582–1583 (1983).

Smith, C.W. et al., "The Anti–rheumatic Potential of a Series of 2,4–Di–substituted–4H–napththo[1,2–b]pyran–3–carbonitriles," *Bioorg. Med. Chem. Lett. 5*:2783–2788, Elsevier Science Ltd. (1995).

Vaishnaw, A.K. et al., "The molecular basis for apoptotic defects in patients with CD95 (Fas/Apo–1) mutations," *J. Clin. Invest. 103*:355–363, American Society for Clinical Investigation (Feb. 1999).

Wakisaka, S. et al., "Modulation by proinflammatory cytokines of Fas/Fas ligand–mediated apoptotic cell death of synovial cells in patients with rheumatoid arthritis (RA)," *Clin. Exp. Immunol. 114*:199–128, Blackwell Science (Oct. 1998).

Wood, D.L. et al., "Inhibition of Mitosis and Microtubule Function through Direct Tubulin Binding by a Novel Antiproliferative Naphthopyran LY290181," *Mol. Pharmacol. 52*:437–444, The American Society for Pharmacology and Experimental Therapeutics (1997).

Zhou, T. et al., "Bisindolylmaleimide VIII facilitates Fas––mediated apoptosis and inhibits T cell–mediated autoimmune disease," *Nat. Med. 5*:42–48, Nature Publishing Group (Jan. 1999).

Elgamal, M.H.A., et al., "Synthesis of some novel nitrogenous furocoumarin derivatives," *Chem. Abs.*, Accession No. 128:321530, American Chemical Society (Apr. 1998).

Tawada, H., et al., "Synthesis of 3–ureido derivatives of coumarin and 2–quinolone as potent acyl–CoA:cholesterol acyltransferase inhibitors," *Chem. Abs.*, Accession No. 123:339669, 1 page, American Chemical Society (1995).

Meguro, K., et al., "Tricyclic heterocyclic compounds, their production and use," *Chem. Abs.*, Accession No. 117:69733, 2 pages, American Chemical Society (1992).

Al-Mousawi, S.M., et al., "Synthesis of new condensed 2-amino-4H-pyran-3-carbonitriles and of 2-aminoquinoline-3-carbonitriles," *Chem. Abs.*, Accession No. 131:199593, 2 pages, American Chemical Society (Jun. 1999).

El Aziz El-Taweel, M.A., et al., "Synthesis of 4H-naptho [1,2-b]pyrans, benzo[h]coumarins, 4H-naphtol[2,1-b:6.5-b]dipyrans 4H-naphtho[1,2-b:3,4-b']dipyrans and pyridine derivatives," *Chem. Abs.*, Accession No. 125:114568, 2 pages, American Chemical Society (1995).

Woods, L.L., and Sterling, J., "New synthesis of naphtho[1,2-b]pyran-2-ones," *Chem. Abs.*, Accession No. 60:45584, 1 page, American Chemical Society (1964).

Radwan, A.M., et al., "A new route for the synthesis of 1,2,4-triazole and 3,4-disubstituted cinnoline derivatives," *Chem. Abs.*, Accession No. 124:117193, 1 page, American Chemical Society (1995).

Pending Non-Provisional U.S. Appl. No. 10/146,139, Cai et al., filed May 16, 2002 (Not Published).

Seaman, D.M., Office Communication for U.S. Appl. No. 10/146,136, 12 pages, United States Patent and Trademark Office (mailed May 7, 2003).

Esmond, R.W., Applicants' Amendments to the Claims for U.S. Appl. No. 10/146,136, 11 pages, "Amendment And Reply Under 37 C.F.R. § 1.111," (filed Sep. 8, 2003).

Seaman, D.M., Office Communication for U.S. Appl. No. 10/146,136, 17 pages, United States Patent and Trademark Office (mailed Nov. 7, 2003).

Esmond, R.W., Applicants' Amendments to the Claims for U.S. Appl. No. 10/146,136, 10 pages, "Amendment And Reply Under 37 C.F.R. § 1.116," (filed Feb. 4, 2004).

Rao, D., Office Communication for U.S. Appl. No. 10/146,138, 11 pages, United States Patent and Trademark Office (mailed Aug. 26, 2004).

U.S. Appl. No. 2003/0065018 A1, "Substituted 4H-Chromenes and Analogs as activators of caspases and inducers of apoptosis and the use thereof", Cai et al.*

* cited by examiner

147D & FC3.008

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Synthetic Peptide

<400> SEQUENCE: 1

Asp Glu Val Asp
1

US 6,906,203 B1

SUBSTITUTED 4H-CHROMENE AND ANALOGS AS ACTIVATORS OF CASPASES AND INDUCERS OF APOPTOSIS AND THE USE THEREOF

CROSS REFERENCE TO RELATED APPLICATIONS

This application claims the benefit of Provisional Application No. 60/185,211, filed Feb. 24, 2000, and Provisional Application No. 60/163,584, filed Nov. 5, 1999, the contents of which are fully incorporated by reference herein.

FIELD OF THE INVENTION

This invention is in the field of medicinal chemistry. In particular, the invention relates to substituted 4H-chromene and analogs, and the discovery that these compounds are activators of caspases and inducers of apoptosis. The invention also relates to the use of these compounds as therapeutically effective anti-cancer agents.

DESCRIPTION OF BACKGROUND ART

Organisms eliminate unwanted cells by a process variously known as regulated cell death, programmed cell death or apoptosis. Such cell death occurs as a normal aspect of animal development as well as in tissue homeostasis and aging (Glucksmann, A., Biol. Rev. Cambridge Philos. Soc. 26:59–86 (1951); Glucksmann, A., Archives de Biologie 76:419–437 (1965); Ellis, et al., Dev. 112:591–603 (1991); Vaux, et al., Cell 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., J. Internal Medicine 237:529–536 (1995)).

Apoptosis is achieved through an endogenous mechanism of cellular suicide (Wyllie, A. H., in Cell Death in Biology and Pathology, Bowen and Lockshin, eds., Chapman and Hall (1981), pp. 9–34). A cell activates its internally encoded suicide program as a result of either internal or external off signals. The suicide program is executed through the activation of a carefully regulated genetic program (Wyllie, et al., Int. Rev. Cyt. 68:251 (1980); Ellis, et al., Ann. Rev. Cell Bio. 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., J. Internal Medicine 237:529–536 (1995)).

It has been found that a group of proteases are a key element in apoptosis (see, e.g., Thornberry, Chemistry and Biology 5:R97–R103 (1998); Thornberry, British Med. Bull. 53:478490 (1996)). Genetic studies in the iematode Caenorhabditis elegans revealed that apoptotic cell death involves at least 14 genes, two of which are the pro-apoptotic (death-promoting) ced (for cell death abnormal) genes, ced-3 and ced4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (Apoptosis and Cancer Chemotherapy, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal-they become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., Biochem. Cell. Biol. 75:301–314 (1997)). BCL-like proteins include BCL and BAX-alpha, which appear to function upstream of caspase activation. BC-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., Blood 90:3118–3129 (1997); Friesen, et al., Nat. Med. 2:574 (1996)). The mechanism of action of current antineoplastic drugs frequently involves an attack at specific phases of the cell cycle. In brief, the cell cycle refers to the stages through which cells normally progress during their lifetimes. Normally, cells exist in a resting phase termed $G_o$. During multiplication, cells progress to a stage in which DNA synthesis occurs, termed S. Later, cell division, or mitosis occurs, in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, for example colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., Goodman and Gilman's The Pharmacological Basis of Therapeutics, Ninth Edition, McGraw-Hill, New York (1996), pp. 1225–1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducer of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

EP537949 discloses derivatives of 4H-naphthol[1,2-b] pyran as antiproliferatives:

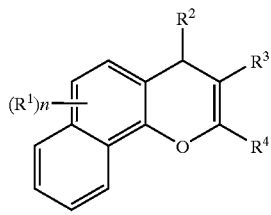

wherein,
each $R^1$ is independently halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —COOR$^5$ where $R^5$ is an ester group, —CONR$^6$R$^7$ or —NR$^6$R$^7$ where $R^6$ and $R^7$ are each hydrogen or $C_{1-4}$ alkyl;

$R^2$ is phenyl, napthyl or heteroaryl selected from thienyl, pyridyl, benzothienyl, quinolinyl, benzofuranyl or benzimidazolyl, wherein said phenyl, napthyl and heteroaryl groups are optionally substituted, or $R^2$ is furanyl optionally substituted with $C_{1-4}$ alkyl;

$R^3$ is nitrile, carboxy, —COOR$^8$ where $R^8$ is an ester group, —CONR$^9$R$^{10}$ where $R^9$ and $R^{10}$ are each hydrogen or $C_{1-4}$ alkyl or $R^{11}SO_2$ where $R^{11}$ is $C_{1-4}$ alkyl or optionally substituted phenyl;

$R^4$ is —NR$^{12}$R$^{13}$, —NHCOR$^{12}$, —N(COR$^{12}$)$_2$ or —N=CHOCH$_2$R$^{12}$ where $R^{12}$ and $R^{13}$ are each hydrogen or $C_{1-4}$ alkyl optionally substituted with carboxy, or $R^4$ is

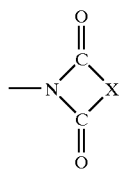

where X is $C_{2-4}$ alkylene, or $R^4$ is —NHSO$_2$R$^{14}$ where $R^{14}$ is $C_{1-4}$ alkyl or optionally substituted phenyl; and
n is 0–2.

U.S. Pat. No. 5,281,619 discloses naphthopyrans for therapy of diabetic complications:

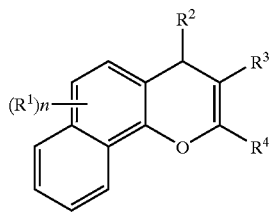

wherein,
$R^1$ is $C_{1-4}$ alkoxy, OH or COOH;
$R^2$ is optionally substituted phenyl;
$R^3$ is nitrile, or $R^3$ is carboxy or —COOR$^8$ when $R^2$ is phenyl substituted with 3-nitro or 3-trifluoromethyl and $R^8$ is an ester group;
$R^4$ is NR$^{12}$R$^{13}$, —NHCOR$^{12}$, —N(COR$^{12}$)$_2$ or —N=CHOCH$_2$R$^{12}$, wherein $R^{12}$ and $R^{13}$ are each H or $C_{1-4}$ alkyl; and
n is 0–2.

EP599514 discloses the preparation of pyranoquinoline derivatives as inhibitors of cell proliferation:

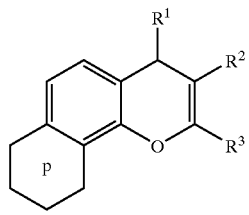

wherein $R^1$ is optionally substituted phenyl or optionally substituted heteroaryl selected from thienyl, pyridyl, benzothienyl, quinolinyl, benzofuranyl or benzimidazolyl, or $R^1$ is furanyl optionally substituted with $C_{1-4}$ alkyl;

$R^2$ is nitrile, carboxy, —CO$_2$R$^4$ wherein $R^4$ is an ester group, —CON(R$^5$)R$^6$ where $R^5$ and $R^6$ are independently H or $C_{1-4}$ alkyl, or $R^7SO_2$ where $R^7$ is $C_{1-4}$ alkyl or optionally substituted phenyl;

$R^3$ is —NR$^8$R$^9$, —NHCOR$^8$, —N(CO$_2$R$^8$)$_2$, —N=CHOR$^8$ where $R^8$ and $R^9$ are independently H or $C_{1-4}$ alkyl, or —NHSO$_2$R$^{10}$ where $R^{10}$ is $C_{1-4}$ alkyl or optionally substituted phenyl, or

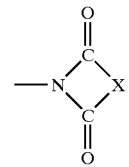

where X is $C_{2-4}$ alkylene; and
the ring P represents a pyridine fused to the benzopyran nucleus.

EP618206 discloses the preparation of naphthopyran and pyranoquinoline as immunosuppressants and cell proliferation inhibitors:

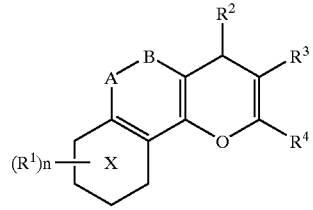

wherein,
A—B is CH$_2$CH$_2$ or CH=CH; each $R^1$ is independently halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, nitrogen-containing heterocyclyl, nitro, trifluoromethoxy, —COOR$^5$ where $R^5$ is an ester group, —COR$^6$, —CONR$^6$R$^7$ or —NR$^6$R$^7$ where $R^6$ and $R^7$ are each hydrogen or $C_{1-4}$ alkyl;

$R^2$ is phenyl, napthyl or heteroaryl selected from thienyl, pyridyl, benzothienyl, quinolinyl, benzofuranyl or benzimidazolyl, wherein said phenyl, napthyl and heteroaryl groups are optionally substituted, or $R^2$ is furanyl optionally substituted with $C_{1-4}$ alkyl;

$R^3$ is nitrile, carboxy, —$COOR^8$ where $R^8$ is an ester group, —$CONR^9R^{10}$ where $R^9$ and $R^{10}$ are each hydrogen or $C_{1-4}$ alkyl, or $SO_2R^{11}$ where $R^{11}$ is $C_{1-4}$ alkyl or optionally substituted phenyl-$C_{1-4}$ alkyl;

$R^4$ is 1-pyrrolyl, 1-imidazolyl or 1-pyrazolyl, each of which is optionally substituted by one or two $C_{1-4}$ alkyl, carboxyl, hydroxyl-$C_{1-4}$ alkyl or —CHO groups, or $R^4$ is 1-(1,2,4-triazolyl), 1-(1,3,4-triazolyl) or 2-(1,2,3-triazolyl), each of which is optionally substituted by a $C_{1-4}$ alkyl or $C_{1-4}$ perfluoroalkyl group, or $R^4$ is 1-tetrazolyl optionally substituted by $C_{1-4}$ alkyl;

X is a pyridine or a benzene ring; and n is 0–2.

EP619314 discloses the preparation of 4-phenyl4H-naphtho(2,1-b)pyran derivatives:

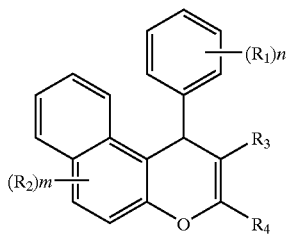

wherein, $R_1$ and $R_2$ are independently halo, trifluoromethyl, $C_1$–$C_4$ alkoxy, hydroxy, nitro, $C_1$–$C_4$ alkyl, $C_1$–$C_4$ alkylthio, hydroxy-$C_1$–$C_4$ alkyl, hydroxy-$C_1$–$C_4$ alkoxy, trifluoromethoxy, carboxy, —$COOR_8$ where $R_8$ is an ester group, —$COR_9$, —$CONR_9R_{10}$ or —$NR_9R_{10}$ where $R_9$ and $R_{10}$ are each hydrogen or $C_1$–$C_4$ alkyl;

$R_3$ is nitrile, carboxy or —$CO_2R_{11}$ wherein $R_{11}$ is an ester group;

$R_4$ is —$NR_{12}R_{13}$, —$NR_{12}COR_{13}$, —$N(COR_{12})_2$ or —N═CHOCH$_2R_{12}$ where $R_{12}$ and $R_{13}$ are each hydrogen or $C_{1-4}$ alkyl, or $R_4$ is

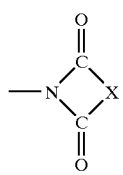

where X is $C_2$–$C_4$ alkylene, or $R_4$ is optionally substituted 1-pyrrolyl; and m and n are each independently 0–2. The compounds arc said to be useful for the treatment of restenosis, immune disease, and diabetic complications.

Smith, et al., (*Bioorg. Med. Chem. Lett.* 5:2783–2788 (1995)) reported the anti-rheumatic potential of a series of 2,4-di-substituted-4H-naphtho[1,2-b]pyran-3-carbonitriles. They reported that 4-(3-nitrophenyl)-2-(N-succinimido)-4H-naphtho[1,2-b]pyran-3-carbonitrile has proved to be acid stable and still retains biological activity:

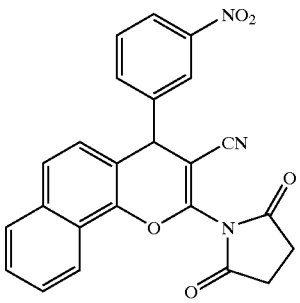

Birch, et al., (*Diabetes* 45:642–650 (1996)) reported that LY290181, an inhibitor of diabetes-induced vascular dysfunction, blocks protein kinase C-stimulated transcriptional activation through inhibition of transcription factor binding to a phorbol response element.

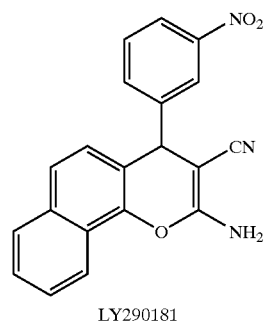

LY290181

Panda, et al, (*J. Biol. Chem.* 272: 7681–7687 (1997)) reported the suppression of microtubule dynamics by LY290181, which might be the potential mechanism for its antiproliferative action.

Wood, et al, (*Mol. Pharmacol.* 52: 437–444 (1997)) reported that LY290181 inhibited mitosis and microtubule function through direct tubulin binding.

PCT published patent application WO9824427 disclosed antimicrotubule compositions and methods for treating or preventing inflammatory diseases. LY290181 was listed as an antimicrotubule agent.

SUMMARY OF THE INVENTION

The present invention is related to the discovery that substituted 4H-chromene and analogs, as represented in Formula I, are activators of the caspase cascade and inducers of apoptosis. Thus, an aspect of the present invention is directed to the use of compounds of Formula I as inducers of apoptosis.

A second aspect of the present invention is to provide a method for treating, preventing or ameliorating neoplasia and cancer by administering a compound of Formula I to a mammal in need of such treatment.

Many of compounds within the scope of the present invention are novel compounds. Therefore, a third aspect of the present invention is to provide novel compounds of Formula L and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A fifth aspect of the present invention is directed to methods for the preparation of novel compounds of Formula I.

BRIEF DESCRIPTION OF THE DRAWINGS

FIG. 1A depicts control cells. FIG. 1B depicts cells treated with 100 nM of 2-amino-3-cyano-7-dimethylamino-4-(3-methoxy-4,5-methylenedioxyphenyl)-4H-chromene for 24 h, showing shrunken and fragmented nuclei.

FIG. 2A: DMSO treated control cells. FIG. 2B: cells treated with 1 μM of staurosporine for 3 h. FIG. 2C: cells treated with 2.5 μM of 2-amino-3-cyano-7-diethylamino-4-(3-methoxy-4,5-methylenedioxyphenyl)-4H-chromene for 5 h. FIG. 2D: cells treated with 2.5 μM of 2-amino-3-cyano-7-dimethylamino-4-(3-methoxy-4,5-methylenedioxyphenyl)-4H-chromene for 15 h. FIG. 2E: cells treated with 2.5 μM of 2-amino-3-cyano-7-dimethylamino-4-(3-methoxy-4,5-methylenedioxyphenyl)-4H-chromene for 30 h.

FIG. 3 shows increasing percent mitotic arrest with increasing drug concentration up to a concentration of 1.0 μM.

FIG. 4A: control cells showing most of the cells in G1. FIG. 4B: cells treated with 1 μM of 2-amino-3-cyano-7-dimethylamino-4-(3-methoxy-4,5-methylenedioxyphenyl)-4H-chromene for 18 h showing progression and arrest in S/G2/M.

FIG. 5A: control cells showing most of the cells in G1. FIG. 5B: cells treated with 1 μM of 2-amino-3-cyano-7-dimethylamino-4-(3-methoxy-4,5-methylenedioxyphenyl)-4H-chromene for 18 h showing progression and arrest in G2/M. FIG. 5C: cells treated with 1 μM of 2-amino-3-cyano-7-dimethylamino-4-(3,4-methylenedioxyphenyl)-4H-chromene for 18 h showing progression and arrest in G2/M.

FIG. 6A: control cells showing most of the cells in G1. FIG. 6B: cells treated with 1 μM of 2-amino-3-cyano-7-dimethylamino-4-(3-methoxy-4,5-methylenedioxyphenyl)-4H-chromene for 18 h showing progression and arrest in G2/M. FIG. 6C: cells treated with 1 μM of 2-amino-3-cyano-7-dimethylamino-4-(3,4-methylenedioxyphenyl)-4-H-chromene for 18 h showing progression and arrest in G2/M.

DETAILED DESCRIPTION OF THE INVENTION

Figure 1A:
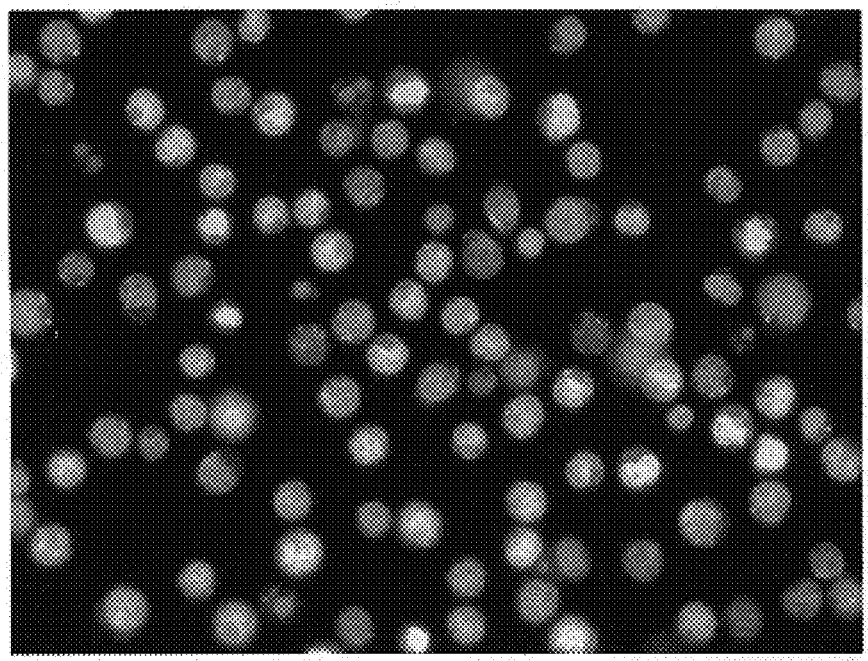
FIGS. 1A–B depict fluorescent micrographs of Jurkat cells as controls and as treated with drug and stained with a fluorescent DNA probe, Syto16.

The present invention arises out of the discovery that substituted 4H-chromene and analogs, as represented in Formula I are potent and highly efficacious activators of the caspase cascade and inducers of apoptosis. Therefore compounds of Formula I are useful for treating disorders responsive to induction of apoptosis.

Specifically, compounds useful in this aspect of the present invention are represented by Formula I:

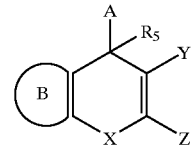

(I)

or pharmaceutically acceptable salts or prodrugs thereof, wherein:

X is O, S or $NR_6$, wherein $R_6$ is hydrogen or optionally substituted alkyl,

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aninoalkyl; or $R_x$ and $R_y$ are taken together with the nitrogen to which they are attached to form a heterocycle;

Z is $NR_8R_9$, $NHCOR_8$, $N(COR_8)_2$, $N(COR_8)(COR_9)$, $N=CHOR_8$ or $N=CHR_8$. wherein $R_8$ and $R_9$ are independently H, $C_{1-4}$ alkyl or aryl, or $R_8$ and $R_9$ are combined together with the group attached to them to form a heterocycle;

$R_5$ is hydrogen or $C_{1-10}$ alkyl;

A is optionally substituted and is aryl, heteroaryl, saturted carbocyclic, partially saturated carbocyclic, saturated heterocyclic, partially saturated heterocyclic, arylalkyl or heteroarylalkyl; and B is an optionally substituted aromatic or heteroaromatic ring.

Preferred compounds of Formula I include compounds wherein A is phenyl, naphthyl, pyridyl, quinolyl, isoquinolyl, thienyl, furyl, pyrrolyl, 2-phenylethyl or cyclohexyl, any of which is optionally substituted.

Preferably B is optionally substituted and selected from the group consisting of benzo, naphtho, indolo, quino and isoquino. Preferably, $R_5$ is hydrogen. Preferably, X is O or S. Most preferably, X is O. Preferably, Z is $NH_2$. Preferably, Y is CN.

Preferred structures of Formula I are substituted 4H-chromene and analogs represented by Formulae II–IV. In particular, a preferred embodiment is represented by Formula II:

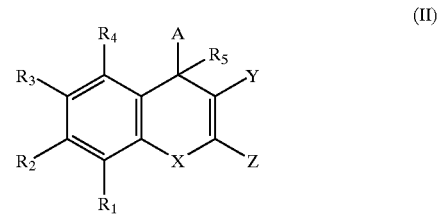

(II)

or pharmaceutically acceptable salts or prodrugs thereof, wherein $R_5$, X, Y, Z and A are as defined previously with respect to Formula 1; and $R_1$–$R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_1$ and $R_2$, or $R_2$ and $R_3$, or $R_3$ and $R_4$, taken together with the atoms to which they are attached form an aryl, heteroaryl, partially saturated carbocyclic or partially saturated heterocyclic group, wherein said group is optionally substituted.

Preferred are compounds of Formula II, wherein $R_1$ and $R_2$, or $R_2$ and $R_3$, or $R_3$ and $R_4$, taken together form a structure selected from the group consisting of —OCH$_2$O, —(CH$_2$)$_3$—, —(CH$_2$)$_4$—, —OCH$_2$CH$_2$O, —CH$_2$N(R)CH$_2$—, —CH$_2$CH$_2$N(R)CH$_2$—, —CH$_2$N(R)CH$_2$CH$_2$—, —N(R)H=CH—, —CH=CH—N(R)—, —O—CH=CH—, —CH=CH—O—, —S—CH=CH—, —CH=CH—S— and —N=CH—CH=N—, wherein R is hydrogen, C$_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Also preferred arm compounds of Formula II, wherein $R_1$ and $R_2$, or $R_2$ and $R_3$, or $R_3$ and $R_4$, taken together form a structure selected from the group consisting of —H=CH—CH=CH—, —N=CH—CH=CH—, —CH=N—CH=CH—, —CH=CH—N=CH— and CH=CH—CH=N—.

Preferred compounds falling within the scope of Formula II include compounds wherein $R_1$–$R_4$ are independently hydrogen, halogen, hydroxy, C$_{1-10}$ alkyl, hydroxyalkyl, aminoalkyl, carboxyalkyl, amino, acylamido, acyloxy, alkoxy, methylenedioxy or alkylthiol. Preferably $R_5$ is hydrogen; X is O; Z is NH$_2$ and Y is CN. Preferably A is optionally substituted phenyl, naphthyl, pyridyl, quinolyl, isoquinolyl, thienyl, furyl, pyrrolyl, 2-phenylethyl or cyclohexyl.

Another preferred embodiment is represented by Formula III:

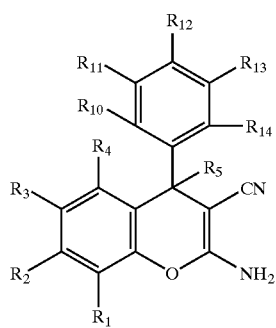

(III)

or pharmaceutically acceptable salts or prodrugs thereof, wherein $R_1$–$R_5$ are as defined previously with respect to Formulae I and II; and $R_{10}$–$R_{14}$ are independently hydrogen, halo, haloalkyl, aryl, fused aryl, carbocyclic, a heterocyclic group, a heteroaryl group, C$_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{10}$ and $R_{11}$, or $R_{11}$ and $R_{12}$, taken together with the atoms to which they are attached form an aryl, heteroaryl, partially saturated carbocyclic or partially saturated heterocyclic group, wherein said group is optionally substituted.

Preferred are compounds of Formula III, wherein $R_{10}$ and $R_{11}$, or $R_{11}$ and $R_{12}$, taken together form a structure selected from the group consisting of —OCH$_2$O—, —(CH$_2$)$_3$—, —(CH$_2$)$_4$—, —OCH$_2$CH$_2$O, —CH$_2$N(R)CH$_2$—, —CH$_2$CH$_2$N(R)CH$_2$—, —CH$_2$N(R)CH$_2$CH$_2$—, CH=CH—CH=CH—, —N(R)—CH=CH—, —CH=CH—N(R)—, —O—CH=CH—, —CH=CH—O—, —S—CH=CH—, —CH=CH—S—, —N=CH—CH=CH—, —CH=N—CH=CH—, —CH=CH—N=CH— and —N=CH—CH=N—, wherein R is hydrogen, C$_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Preferred compounds falling within the scope of Formula III include compounds wherein $R_1$–$R_4$ are independently hydrogen, halogen, hydroxy, C$_{1-10}$ alkyl, hydroxyalkyl, aninoalkyl, carboxyalkyl, amino, acylamido, acyloxy, alkoxy, methylenedioxy or alkylthiol. Preferably $R_5$ is hydrogen.

Another preferred embodiment is represented by Formula IV:

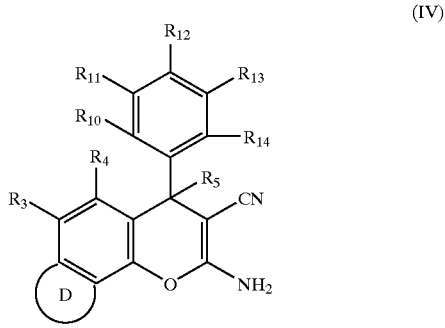

(IV)

or pharmaceutically acceptable salts or prodrugs thereof, wherein;

$R_3$–$R_4$ are independently hydrogen, halo, haloalkyl, aryl, fused aryl, carbocyclic, a heterocyclic group, a heteroaryl group, C$_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or C$_{1-10}$ alkyl;

$R_{10}$–$R_{14}$ are independently hydrogen, halo, haloalkyl, aryl, fused aryl, carbocyclic, a heterocyclic group, a heteroaryl group, C$_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{10}$ and $R_{11}$, or $R_{11}$ and $R_{12}$, taken together with the atoms to which they are attached form an aryl, heteroaryl, partially saturated carbocyclic or partially saturated heterocyclic group, wherein the group is optionally substituted; and D is an optionally substituted aromatic or heteroaromatic ring.

Preferred compounds falling within the scope of Formula IV include compounds wherein $R_3$–$R_4$ are hydrogen. Preferably R$_5$ is hydrogen. Another group of preferred compounds are those wherein R$_{10}$ and R$_{14}$ are hydrogen. Preferably D is an optionally substituted aromatic or heteroaromatic ring selected from the group consisting of benzo, pyrido, furo, thieno, pyrrolo, imidazo and pyrazo.

Exemplary preferred compounds that may be employed in the method of the invention include, without limitation:

- 2-Amino-3-cyano-7-dimethylamino-4-(3-methoxy-4,5-methylene-dioxyphenyl)-4H-chromene;
- 2-Amino-3-cyano-7-dimethylamino-4-(3,4-methylenedioxyphenyl)-4H-chromene;
- 2-Amino-3-cyano-7-dimethylamino-4-(1-naphthyl)-4H-chromene;
- 2-Amino-3-cyano-7-dimethylamino-4-(2-naphthyl)-4H-chromene;
- 2-Amino-3-cyano-7-dimethylamino-4-(3-bromo-4-methoxyphenyl)-4H-chromene;
- 2-Amino-3-cyano-7-dimethylamino-4-(3-bromo-4,6-dimethoxy-phenyl)-4H-chromene;
- 2-Amino-3-cyano-7-dimethylamino-4-(4-trifluoromethylphenyl)-4H-chromene;
- 2-Amino-3-cyano-7-dimethylamino-4-(3-trifluoromethylphenyl)-4H-chromene;
- 2-Amino-3-cyano-7-diethylamino-4-(3-bromo-4-fluorophenyl)-4H-chromene;
- 2-Amino-3-cyano-7-dimethylamino-4-(3,4,5-trimethoxyphenyl)-4H-chromene;
- 2-Acetamido-3-cyano-7-dimethylamino-4-(3,4methylenedioxyphenyl)-4H-chromene;
- 2-Di(ethoxycarbonyl)amino-3-cyano-7-dimethylamino-4-(3,4-methylenedioxyphenyl)-4H-chromene;
- 2-Amino-3-cyano-7-dimethylamino-4-(2-chloro-4,5-methylenedioxy-phenyl)-4H-chromene;
- 2-Amino-3-cyano-7-diethylamino-4-(3-pyridyl)-4H-chromene;
- 2-Amino-3-cyano-7-diethylamino-4-(4-methyl-3-nitrophenyl)-4H-chromene;
- 2-Amino-3-cyano-7-dimethylamino-4-(3,4-dimethylphenyl)-4H-chromene;
- 3-Cyano-7-dimethylamino-4-(4,5-methylenedioxyphenyl)-2-propionamido-4H-chromene;
- 2-Amino-3-cyano-7-dimethylamino-4-(3,5-dimethylphenyl)-4H-chromene;
- 2-Amino-3-cyano-7-dimethylamino-4-(2-fluoro-5-methoxyphenyl)-4H-chromene;
- 2-Amino-3-cyano-7-dimethylamino-4-(3-methoxy-4,5-methylenedioxyphenyl)-4H-chromene;
- 2-Amino-3-cyano-7-dimethylamino-4-phenyl-4H-chromene;
- 2-Benzylidenamino-3-cyano-7-dimethylamino-4-phenyl-4H-chromene;
- 2-Amino-3-cyano-7-dimethylamino-4-cyclohexyl-4H-chromene;
- 2-Amino-3-cyano-7-dimethylamino-4-(2-fluoro-3-trifluoromethylphenyl)-4H-chromene;
- 2-Amino-3-cyano-7-dimethylamino-4-(2,4,5-trifluorophenyl)-4H-chromene;
- 2-Amino-3-cyano-7-dimethylamino-4-(2,3,4-trifluorophenyl)-4H-chromene;
- 2-Amino-3-cyano-7-dimethylamino-4-(2-fluoro-5-nitrophenyl)-4H-chromene;
- 2-Amino-3-cyano-7-dimethylamino-4-(4-chloro-3-nitrophenyl)-4H-chromene;
- 2-Amino-3-cyano-7-dimethylamino-4-(3-nitrophenyl)-4H-chromene;
- 2-Amino-3-cyano-7-dimethylamino-4-(3-bromo-4,5-dimethoxyphenyl)-4H-chromene;
- 2-Amino-3-cyano-7-dimethylamino-4-(3,4-ethylenedioxyphenyl)-4H-chromene;
- 2-Amino-3-cyano-7-dimethylamino-4-(3,4-methoxyphenyl)-4H-chromene;
- 2-Amino-3-cyano-7-dimethylamino-4-(4-fluoro-3-trifluoromethyl-phenyl)-4H-chromene;
- 2-Amino-3-cyano-7-dimethylamino-4-(3-pyridyl)-4H-chromene;
- 2-Amino-3-cyano-6,7-methylenedioxy-4-(3-methoxy-4,5-methylenedioxyphenyl)-4H-chromene;
- 2-Amino-3-cyano-7-dimethylamino-4-(3-methoxy-4,5-methylenedioxyphenyl)-4H-chromene;
- 2-Amino-3-cyano-7-dimethylamino-4(2-fluoro-5-trifluoromethylphenyl)-4H-chromene;
- 2-Amino-3-cyano-7-dimethylamino-4-(3-fluoro-4-trifluoromethylphenyl)-4H-chromene;
- 2-Amino-3-cyano-7-dimethylamino-4-(3,4-difluoromethylenedioxy-phenyl)-4H-chromene;
- 2-Amino-3-cyano-7-dimethylamino-4-(3,4-difluoro-5-trifluoromethylphenyl)-4H-chromene;
- 2-Amino-3-cyano-7-dimethylamino-4-(5-nitro-2-furyl)-4H-chromene;
- 2-Amino-3-cyano-7-dimethylamino-4-(5-nitro-2-thienyl)-4H-chromene;
- 2-Amino-3-cyano-7-dimethylamino-4-(2-chloro-5-trifluoromethylphenyl)-4H-chromene;
- 2-Amino-3-cyano-7-dimethylamino-4-(3-chloro-6-nitrophenyl)-4H-chromene;
- 2-Amino-3-cyano-7-dimethylamino-4-(2-chloro-5-nitrophenyl)-4H-chromene;
- 2-Amino-3-cyano-7-dimethylamino-4-(3-phenoxyphenyl)-4H-chromene;
- 2-Amino-3-cyano-7-dimethylamino-4-(2-pyridyl)-4H-chromene;
- 2-Amino-3-cyano-7-dimethylamino-4-(2-phenylethyl)-4H-chromene;
- 2-Amino-3-cyano-7-dimethylamino-4-(3-fluoro-6-nitrophenyl)-4H-chromene;
- 2-Amino-3-cyano-7-dimethylamino-4-(4-chloro-5-trifluoromethylphenyl)-4H-chromene;
- 2-Amino-3-cyano-7-dimethylamino-4-(2,3-difluoro-4-trifluoromethylphenyl)-4H-chromene;
- 2,7-Diamino-3-cyano-4-(3-methoxy-4,5-methylenedioxyphenyl)-4H-chromene;
- 2-Amino-3-cyano-7-dimethylamino-4-(4-pyridyl)-4H-chromene;
- 2-Amino-3-cyano-7-dimethylamino-4-(3,5-dimethoxyphenyl)-4H-4-chromene;
- 2-Amino-3-cyano-7-dimethylamino-4-(3-(4-methoxyphenoxy)phenyl)-4H-chromene;
- 2-Amino-3-cyano-7-dimethylamino-4-(3,5-dichlorophenyl)-4H-chromene;
- 2-Amino-3-cyano-7-dimethylamino-4-(3-fluoro-6-trifluoromethylphenyl)-4H-chromene;
- 2-Amino-3-cyano-7-dimethylamino-4-(3-quinolyl)-4H-chromene;

2-Amino-3-cyano-7-dimethylamino-4-(2-quinolyl)-4H-chromene;
2-Amino-3-cyano-7-dimethylamino-4-phenylmethyl-4H-chromene;
2-Amino-3-cyano-7-dimethylamino-4-(4-carboxaldehydephenyl)-4H-chromene;
2-Amino-3-cyano-7-dimethylamino-4-(4-bromo-3,5-dimethoxyphenyl)-4H-chromene;
2-Amino-7-acetamido-3-cyano-4(3-bromo-4,5-dimethoxyphenyl)-4H-chromene;
2,7-Diamino-3-cyano(3-bromo-4,5-methoxyphenyl)-4H-chromene;
2-Amino-3-cyano-4-(3-methoxy-4,5-methylenedioxyphenyl)-6,7,8,9,10,11-hexahydro-4H-pyrido[3,2,1-ij]quino[5,6-b]pyran;
2-Amino-3-cyano-4-(3-methoxy-4,5-methylenedioxyphenyl)-4H-indolo[4,5-b]pyran;
2-Amino-3-cyano-7-ethylamino-6-methyl-4-(3-methoxy-4,5-methylenedioxyphenyl)-4H-chromene;
2,7-Diamino-3-cyano-8-methyl-4-(3-methoxy-4,5-methylenedioxyphenyl)-4H-chromene;
2-Amino-7-chloroacetamido-3-cyano-4-(3-bromo-4,5-dimethoxyphenyl)-4H-chromene;
2-Amino-3-cyano-4-(2-bromo-4,5-dimethoxyphenyl)-4H-indolo[4,5-b]pyran;
2-Amino-3-cyano-7-dimethylamino-4-(3-bromophenyl)-4H-chromene;
2-Amino-3-cyano-7-dimethylamino-4-(3,5-dibromophenyl)-4H-chromene;
2-Amino-3-cyano-7-dimethylamino-4-(3-cyanophenyl)-4H-chromene;
2-Amino-3-cyano-7-dimethylamino-4-(3-methylphenyl)-4H-chromene;
2-Amino-3-cyano-7-dimethylamino-4-(3-chlorophenyl)-4H-chromene;
2-Amino-3-cyano-4-(3-bromo-4,5-dimethoxyphenyl)-4H-naphtho[1,2-b]pyran;
2-Amino-3-cyano-4-(3-bromo-4,5-dimethoxyphenyl)-4H-indolo[4,5-b]pyran;
2-Amino-3-cyano-4-(3-bromo-4,5-dimethoxyphenyl)-8-methyl-4H-indolo[4,5-b]pyran;
2-Amino-3-cyano-7-dimethylamino-4-(3-methoxyphenyl)-4H-chromene;
2-Amino-3-cyano-4-(3,4,5-trimethoxyphenyl)-4H-indolo[4,5-b]pyran;
2-Amino-3-cyano-4-(3-nitrophenyl)-4H-indolo[4,5-b]pyran;
2-Amino-3-cyano-4-(3-cyanophenyl)-4H-indolo[4,5-b]pyran;
2-Amino-3-cyano-7-dimethylamino-4-(3,5-difluorophenyl)-4H-chromene;
2-Amino-3-cyano-4-(3,5-dimethoxyphenyl)-4H-indolo[4,5-b]pyran;
2-Amino-3-cyano-7-dimethylamino-4-(3,5-bis(trifluoromethyl)phenyl)-4H-chromene;
2-Amino-3-cyano-7-dimethylamino-4-(3-bromo-5-methoxyphenyl)-4H-chromene;
2-Amino-3-cyano-4-(4-bromo-3,5-dimethoxyphenyl)-4H-naphtho[1,2-b]pyran;
2-Amino-3-cyano-4-(3-methoxy-4,5-methelenedioxyphenyl)-4H-naphtho[1,2-b]pyran;
2-Amino-3-cyano-4-(3,4,5-trimethoxyphenyl)-4H-naphtho[1,2-b]pyran;
2-Amino-3-cyano-7-dimethylamino-4-(4-chloromethylphenyl)-4H-chromene;
2-Amino-3-cyano-7-dimethylamino-4-(3-chloromethylphenyl)-4H-chromene;
2-Amino-3-cyano-7-dimethylamino-4-(3-cyano-4-fluorophenyl)-4H-chromene;
2-Amino-3-cyano-7-dimethylamino-4-(3-nitro-4-fluorophenyl)-4H-chromene;
2-Amino-3-cyano-7-dimethylamino-4-(3-bromo-4,5-methylenedioxyphenyl)-4H-chromene;
2-Amino-3-cyano-7-methoxy-4-(3-bromo-4,5-dimethoxyphenyl)-4H-chromene;
2-Amino-3-cyano-7-dimethylamino-4-(3-trifluoromethylthiophenyl)-4H-chromene;
2-Amino-3-cyano-7-dimethylamino-4-(3-fluorophenyl)-4H-chromene;
2-Amino-3-cyano-7-dimethylamino-4-(3-difluoromethoxyphenyl)-4H-chromene;
2-Amino-3-cyano-7-dimethylamino-4-(3-hydroxyphenyl)-4H-chromene;
2-Amino-3-cyano-7-dimethylamino-4-(3-trifluoromethoxyphenyl)-4H-chromene;
2-Amino-3-cyano-7-dimethylamino-4-(3-methylaminophenyl)-4H-chromene;
2-Amino-3-cyano-7-dimethylamino-4-(3-dimethylaminophenyl-4H-chromene;
2-Amino-3-cyano-7-dimethylamino-4-(3-iodo-4,5-dimethoxyphenyl)-4H-naphtho[1,2-b]pyran;
2-Amino-3-cyano-7-dimethylamino-4-(3-iodo-4,5-dimethoxyphenyl)-4H-chromene;
2-Amino-3-cyano-7-dimethylamino-4-(4-acetoxy-3,5-dimethoxyphenyl)-4H-chromene;
2-Amino-3-cyano-7-dimethylamino-4-(4-acetoxy-3,5-dimethoxyphenyl)-4H-naphtho[1,2-b]pyran;
2-Amino-3-cyano-7-dimethylamino-4-(5-methyl-3-pyridyl)-4H-chromene;
2-Amino-3-cyano-7-dimethylamino-4-(3-chloro-4,5-dimethoxyphenyl)-4H-chromene;
2-Chloroacetamido-3-cyano-7-dimethylamino-4-(3-bromo-4,5-dimethoxyphenyl)-4H-chromene;
2-Acrylamido-3-cyano-7-dimethylamino-4-(3-bromo-4,5-dimethoxyphenyl)-4H-chromene;
3Cyano-7-dimethylamino-2-succinimido-4-(3-bromo-4,5-dimethoxyphenyl)-4H-chromene;
3-Cyano-7-dimethylamino-2-phenylureido-4-(3-bromo-4,5-dimethoxyphenyl)-4H-chromene;
9-Acetamide-2-amino-3-cyano-4-(3-bromo-4,5-dimethoxyphenyl)-4H-indolo[4,5-b]pyran;
2-Amino-3-cyano-7-methylamino-4-(5-bromo-3-pyridyl)-4H-chromene;
2-Amino-3-cyano-7-dimethylamino-4-(6-methyl-3-pyridyl)-4H-chromene;
2-Amino-3-cyano-7-dimethylamino-4-(6methyl-2-pyridyl)-4H-chromene;
2-Amino-3-cyano-7-dimethylamino-4-(2-bromo-4,5-methylenedioxyphenyl)-4H-chromene;
2-Amino-3-cyano-4-(3-bromo-4,5-dimethoxyphenyl)-4H-naphtho[2,1-b]pyran;
2-Amino-3-cyano-7-dimethylamino-4-(4-chloro-2-nitrophenyl)-4H-chromene;
2-Amino-3-cyano-4-(3-bromo-4,5-dimethoxyphenyl)-4H-quino[5,6-b]pyran;

2-Amino-3-cyano-4-(3-bromo-4,5-dimethoxyphenyl)-4H-isoquino[5,6-b]pyran;
2-Amino-3-cyano-4-(3-bromo-4,5-dimethoxyphenyl)-4H-quino[8,7-b]pyran;
2-Amino-3-cyano-7-ethoxy-4-(3-bromo-4,5methoxyphenyl)-4H-chromene;
2-Amino-3-cyano-4-(3-bromo-4,5-dimethoxyphenyl)-7,8,9,10-tetrahydro-4H-naphtho[1,2-b]pyran;
2-Amino-3-cyano-4-(3-bromo-4,5-dimethoxyphenyl)-7,8-dimethyl4H-chromene;
2-Amino-3-cyano-4-(3,4,5-trimethoxyphenyl-4H-quino[5,6-b]pyran;
2-Amino-3-cyano-4-(3-bromo-4-hydroxy-5-methoxyphenyl)-4H-naphtho[1,2-b]pyran;
2-Amino-6-chloro-3-cyano-4-(3-bromo-4-hydroxy-5-methoxyphenyl)-4H-naphtho[1,2-b]pyran;
2-Amino-3-cyano-7-methoxy-4-(3,4,5-trimethoxyphenyl)-4H-chromene;
2-Amino-3-cyano-7-methoxy-4-(3,5-dimethoxyphenyl)-4H-chromene;
2-Amino-3-cyano-7-methoxy-4-(3-methoxyphenyl)-4H-chromene;
2-Amino-3-cyano-7-methoxy-4-(3-cyanophenyl)-4H-chromene;
2-Amino-3-cyano-7-methoxy-4-(3-chlorophenyl)-4H-chromene;
2-Amino-3-cyano-7-methoxy-4-(3-nitrophenyl)-4H-chromene;
2-Amino-3-cyano-7-methoxy-4-(3-bromophenyl)-4H-chromene;
2-Amino-3-cyano-7-methoxy-4-(5-methyl-3-pyridyl)-4H-chromene;
2-Amino-3-cyano-7-methoxy-4-(5-methoxy-3-pyridyl)-4H-chromene;
2-Amino-3-cyano-7-methoxy-4-(5-methylthio-3-pyridyl)-4H-chromene;
2-Amino-3-cyano-7-methoxy-4-(5-chloro-3-pyridyl)-4H-chromene;
2-Amino-3-cyano-7-methoxy-4-(5-bromo-3-pyridyl)-4H-chromene;
2-Amino-3-cyano-7-methyl-4-(3-bromo-4,5-dimethoxyphenyl)-4H-chromene;
2-Amino-3-cyano-7-chloro-4-(3-bromo-4,5-dimethoxyphenyl)-4H-chromene;
2-Amino-3-cyano-7-bromo-4-(3-bromo-4,5-dimethoxyphenyl)-4H-chromene;
2-Amino-3-cyano-7-bromo-4-(5-methyl-3-pyridyl)-4H-chromene;
2-Amino-3-cyano-7-chloro-4-(5-methyl-3-pyridyl)-4H-chromene;
2-Amino-3-cyano-7-ethylamino-4-(3-bromo-4,5-dimethoxyphenyl)-4H-chromene;
2-Amino-3-cyano-7-ethylamino-4-(5-methyl-3-pyridyl)-4H-chromene; and
2-Amino-3-cyano-7-hydroxy-4-(3-bromo-4,5-dimethoxyphenyl)-4H-chromene.

The present invention is also directed to novel compounds within the scope of Formulae I–IV.

Exemplary preferred novel compounds of this invention include, without limitation:

2-Amino-3-cyano-7-dimethylamino-4-(3,4-methylenedioxyphenyl)-4H-chromene;
2-Amino-3-cyano-7-dimethylamino-4-(2-naphthyl)-4H-chromene;
2-Amino-3-cyano-7-dimethylamino-4-(3,4,5-trimethoxyphenyl)-4H-chromene;
2-Acetamido-3-cyano-7-dimethylamino-4-(3,4-methylenedioxyphenyl)-4H-chromene;
2-Di(ethoxycarbonyl)amino-3-cyano-7-dimethylamino-4-(3,4-methylenedioxyphenyl)-4H-chromene;
2-Amino-3-cyano-7-dimethylamino-4-(2-chloro-4,5-methylenedioxyphenyl)-4H-chromene;
2-Amino-3-cyano-7-dimethylamino-4-(4-methyl-3-nitrophenyl)-4H-chromene;
2-Amino-3-cyano-7-dimethylamino-4-(3,4-dimethylphenyl)-4H-chromene;
3-Cyano-7-dimethylamino-4-(4,5-methylenedioxyphenyl)-2-propionamido-4H-chromene;
2-Amino-3-cyano-7-dimethylamino-4-(3,5-dimethylphenyl)-4H-chromene;
2-Amino-3-cyano-7-dimethylamino-4-(2-fluoro-5-methoxyphenyl)-4H-chromene;
2-Amino-3-cyano-7-dimethylamino-4-(3-methoxy-4,5-methylenedioxyphenyl)-4H-chromene;
2-Amino-3-cyano-7-dimethylamino-4-phenyl-4H-chromene;
2-Benzylidenamino-3-cyano-7-dimethylamino-4-phenyl-4H-chromene;
2-Amino-3-cyano-7-dimethylamino-4-cyclohexyl-4H-chromene;
2-Amino-3-cyano-7-dimethylamino-4-(2-fluoro-3-trifluoromethylphenyl)-4H-chromene;
2-Amino-3-cyano-7-dimethylamino-4-(2,4,5-trifluorophenyl)-4H-chromene;
2-Amino-3-cyano-7-dimethylamino-4-(2,3,4-trifluorophenyl)-4H-chromene;
2-Amino-3-cyano-7-dimethylamino-4-(2-fluoro-5-nitrophenyl)-4H-chromene;
2-Amino-3-cyano-7-dimethylamino-4-(4-chloro-3-nitrophenyl)-4H-chromene;
2-Amino-3-cyano-7-dimethylamino-4-(3-nitrophenyl)-4H-chromene;
2-Amino-3-cyano-7-dimethylamino-4-(3-bromo-4,5-dimethoxyphenyl)-4H-chromene;
2-Amino-3-cyano-7-dimethylamino-4-(3,4-ethylenedioxyphenyl)-4H-chromene;
2-Amino-3-cyano-7-dimethylamino-4-(3,4-dimethoxyphenyl)-4H-chromene;
2-Amino-3-cyano-7-dimethylamino-4-(4-fluoro-3-trifluoromethyl-phenyl)-4H-chromene;
2-Amino-3-cyano-7-dimethylamino-4-(3-pyridyl)-4H-chromene;
2-Amino-3-cyano-6,7-methylenedioxy-4-(3-methoxy-4,5-methylene-dioxyphenyl)-4H-chromene;
2-Amino-3-cyano-7-ethylamino-4-(3-methoxy-4,5-methylenedioxyphenyl)-4H-chromene;
2-Amino-3-cyano-7-dimethylamino-4-(2-fluoro-5-trifluoromethylphenyl)-4H-chromene;
2-Amino-3-cyano-7-dimethylamino-4-(3-fluoro-4-trifluoromethylphenyl)-4H-chromene;
2-Amino-3-cyano-7-dimethylamino-4-(3,4-difluoromethylenedioxyphenyl)-4H-chromene;
2-Amino-3-cyano-7-dimethylamino-4-(3,4-difluoro-5-trifluoromethylphenyl)-4H-chromene;

2-Amino-3-cyano-7-dimethylamino-4-(5-nitro-2-furyl)-4H-chromene;
2-Amino-3-cyano-7-dimethylamino-4-(5-nitro-2-thienyl)-4H-chromene;
2-Amino-3-cyano-7-dimethylamino-4-(2-chloro-5-trifluoromethylphenyl)-4H-chromene;
2-Amino-3-cyano-7-dimethylamino-4-(3-chloro-6-nitrophenyl)-4H-chromene;
2-Amino-3-cyano-7-dimethylamino-4-(2-chloro-5-nitrophenyl)-4H-chromene;
2-Amino-3-cyano-7-dimethylamino-4-(3-phenoxyphenyl)-4H-chromene;
2-Amino-3-cyano-7-dimethylamino-2-pyridyl)-4H-chromene;
2-Amino-3-cyano-7-dimethylamino-4-(2-phenylethyl)-4H-chromene;
2-Amino-3-cyano-7-dimethylamino-4-(3-fluoro-6-nitrophenyl)-4H-chromene;
2-Amino-3-cyano-7-dimethylamino-4-(4-chloro-5-trifluoromethylphenyl)-4H-chromene;
2-Amino-3-cyano-7-dimethylamino-4-(2,3-difluoro-4-trifluoromethylphenyl)-4H-chromene;
2,7-Diamino-3-cyano-4-(3-methoxy-4,5-methylenedioxyphenyl)-4H-chromene;
2-Amino-3-cyano-7-dimethylamino-4-(4-pyridyl)-4H-chromene;
2-Amino-3-cyano-7-dimethylamino-4-(3,5-dimethoxyphenyl)-4H-chromene;
2-Amino-3-cyano-7-dimethylamino-4-(3-(4-methoxyphenoxy)phenyl)-4H-chromene;
2-Amino-3-cyano-7-dimethylamino-4-(3,5-dichlorophenyl)-4H-chromene;
2-Amino-3-cyano-7-dimethylamino-4-(3-fluoro-6-trifluoromethylphenyl)-4H-chromene;
2-Amino-3-cyano-7-dimethylamino-4-(3-quinolyl)-4H-chromene;
2-Amino-3-cyano-7-dimethylamino-4-(2-quinolyl)-4H-chromene;
2-Amino-3-cyano-7-dimethylamino-4-phenylmethyl-4H-chromene;
2-Amino-3-cyano-7-dimethylamino-4-(4-carboxaldehydephenyl)-4H-chromene;
2-Amino-3-cyano-7-dimethylamino-4-(4-bromo-3,5-dimethoxyphenyl)-4H-chromene;
2-Amino-7-acetamido-3-cyano-4-(3-bromo-4,5-dimethoxyphenyl)-4H-chromene;
2,7-Diamino-3-cyano-4-(3-bromo-4,5-dimethoxyphenyl)-4H-chromene;
2-Amino-3-cyano-4-(3-methoxy-4,5-methylenedioxyphenyl)-6,7,8,9,10,11-hexahydro-4H-pyrido[3,2,1-ij]quino[5,6-b]pyran;
2-Amino-3-cyano-4-(3-methoxy-4,5-methylenedioxyphenyl)-4H-indolo[4,5-b]pyran;
2-Amino-3-cyano-7-ethylamino-6-methyl-4-(3-methoxy-4,5-methylenedioxyphenyl)-4H-chromene;
2,7-Diamino-3-cyano-8-methyl-4-(3-methoxy-4,5-methylenedioxyphenyl)-4H-chromene;
2-Amino-7-chloroacetamido-3-cyano-4-(3-bromo-4,5-dimethoxyphenyl)-4H-chromene;
2-Amino-3-cyano-4-(2-bromo-4,5-dimethoxyphenyl)-4H-indolo[4,5-b]pyran;
2-Amino-3-cyano-7-dimethylamino-4-(3-bromophenyl)-4H-chromene;
2-Amino-3-cyano-7-dimethylamino-4-(3,5-dibromophenyl)-4H-chromene;
2-Amino-3-cyano-7-dimethylamino-4-(3-cyanophenyl)-4H-chromene;
2-Amino-3-cyano-7-dimethylamino-4-(3-methylphenyl)-4H-chromene;
2-Amino-3-cyano-7-dimethylamino-4-(3-chlorophenyl)-4H-chromene;
2-Amino-3-cyano-4-(3-bromo-4,5-dimethoxyphenyl)-4H-naphtho[1,2-b]pyran;
2-Amino-3-cyano-4-(3-bromo-4,5-dimethoxyphenyl)-4H-indolo[4,5-b]pyran;
2-Amino-3-cyano-4-(3-bromo-4,5-dimethoxyphenyl)-8-methyl-4H-indolo[4,5-b]pyran;
2-Amino-3-cyano-7-dimethylamino-4-(3-methoxyphenyl)-4H-chromene;
2-Amino-3-cyano-4-(3,4,5-trimethoxyphenyl)-4H-indolo[4,5-b]pyran;
2-Amino-3-cyano-4-(3-nitrophenyl)-4H-indolo[4,5-b]pyran;
2-Amino-3-cyano-4-(3-cyanophenyl)-4H-indolo[4,5-b]pyran;
2-Amino-3-cyano-7-dimethylamino-4-(3,5-difluorophenyl)-4H-chromene;
2-Amino-3-cyano-4-(3,5-dimethoxyphenyl)-4H-indolo[4,5-b]pyran;
2-Amino-3-cyano-7-dimethylamino-4-(3,5-bis(trifluoromethyl)phenyl)-4H-chromene;
2-Amino-3-cyano-7-dimethylamino-4-(3-bromo-5-methoxyphenyl)-4H-chromene;
2-Amino-3-cyano-4-(4-bromo-3,5-dimethoxyphenyl)-4H-naphtho[1,2-b]pyran;
2-Amino-3-cyano-4-(3-methoxy-4,5-methelenedioxyphenyl)-4H-naphtho[1,2-b]pyran;
2-Amino-3-cyano-4-(3,4,5-trimethoxyphenyl)-4H-naphthol[1,2-b]pyran;
2-Amino-3-cyano-7-dimethylamino-4-(4-chloromethylphenyl)-4H-chromene;
2-Amino-3-cyano-7-dimethylamino-4-(3-chloromethylphenyl)-4H-chromene;
2-Amino-3-cyano-7-dimethylamino-4-(3-cyano-4-fluorophenyl)-4H-chromene;
2-Amino-3-cyano-7-dimethylamino-4-(3-nitro-4-fluorophenyl)-4H-chromene;
2-Amino-3-cyano-7-dimethylamino-4-(3-bromo-4,5-methylenedioxyphenyl)-4H-chromene;
2-Amino-3-cyano-7-methoxy-4-(3-bromo-4,5-dimethoxyphenyl)-4H-chromene;
2-Amino-3-cyano-7-dimethylamino-4-(3-trifluoromethylthiophenyl)-4H-chromene;
2-Amino-3-cyano-7-dimethylamino-4-(3-difluoromethoxyphenyl)-4H-chromene;
2-Amino-3-cyano-7-dimethylamino-4-(3-hydroxyphenyl)-4H-chromene;
2-Amino-3-cyano-7-dimethylamino-4-(3-trifluoromethoxyphenyl)-4H-chromene;
2-Amino-3-cyano-7-dimethylamino-4-(3-methylaminophenyl)-4H-chromene;
2-Amino-3-cyano-7-dimethylamino-4-(3-dimethylaminophenyl-4H-chromene;
2-Amino-3-cyano-7-dimethylamino-4-(3-iodo-4,5-dimethoxyphenyl)-4H-naphtho[1,2-b]pyran;

2-Amino-3-cyano-7-dimethylamino-4-(3-iodo-4,5-dimethoxyphenyl)-4H-chromene;
2-Amino-3-cyano-7-dimethylamino-4-(4-acetoxy-3,5-dimethoxyphenyl)-4H-chromene;
2-Amino-3-cyano-7-dimethylamino-4-(4-acetoxy-3,5-dimethoxyphenyl)-4H-naphtho[1,2-b]pyran;
2-Amino-3-cyano-7-dimethylamino-4-(5-methyl-3-pyridyl)-4H-chromene;
2-Amino-3-cyano-7-dimethylamino-4-(3-chloro-4,5-dimethoxy-phenyl)-4H-chromene;
2-Chloroacetamido-3-cyano-7-dimethylamino-4-(3-bromo-4,5-dimethoxyphenyl)-4H-chromene;
2-Acrylamido-3-cyano-7-dimethylamino-4-(3-bromo-4,5-dimethoxy-phenyl)-4H-chromene;
3-Cyano-7-dimethylamino-2-succinimido-4-(3-bromo-4,5-dimethoxyphenyl)-4H-chromene;
3-Cyano-7-dimethylamino-2-phenylureido-4-(3-bromo-4,5-dimethoxyphenyl)-4H-chromene;
9-Acetamide-2-amino-3-cyano-4-(3-bromo-4,5-dimethoxyphenyl)-4H-indolo[4,5-b]pyran;
2-Amino-3-cyano-7-dimethylamino-4-(5-bromo-3-pyridyl)-4H-chromene;
2-Amino-3-cyano-7-dimethylamino-4-(6methyl-3-pyridyl)-4H-chromene;
2-Amino-3-cyano-7-dimethylamino-4-(6methyl-2-pyridyl)-4H-chromene;
2-Amino-3-cyano-7-dimethylamino-4-(2-bromo-4,5-methylenedioxyphenyl)-4H-chromene;
2-Amino-3-cyano-4-(3-bromo-4,5-dimethoxyphenyl)-4H-naphtho[2,1-b]pyran;
2-Amino-3-cyano-7-dimethylamino-4-(4-chloro-2-nitrophenyl)-4H-chromene;
2-Amino-3-cyano-4-(3-bromo-4,5-dimethoxyphenyl)-4H-quino[5,6-b]pyran;
2-Amino-3-cyano-4-(3-bromo-4,5-dimethoxyphenyl)-4H-isoquino[5,6-b]pyran;
2-Amino-3-cyano-4-(3-bromo-4,5-dimethoxyphenyl)-4H-quino[8,7-b]pyran;
2-Amino-3-cyano-7-ethoxy-4-(3-bromo-4,5-dimethoxyphenyl)-4H-chromene;
2-Amino-3-cyano-4-(3-bromo-4,5-dimethoxyphenyl)-7,8,9,10-tetrahydro-4H-naphtho[1,2-b]pyran;
2-Amino-3-cyano-4-(3-bromo-4,5-dimethoxyphenyl)-7,8-dimethyl-4H-chromene;
2-Amino-3-cyano-4-(3,4,5-trimethoxyphenyl-4H-quino[5,6-b]pyran;
2-Amino-3-cyano-7-methoxy-4-(3,4,5-trimethoxyphenyl)-4H-chromene;
2-Amino-3-cyano-7-methoxy-4-(3,5-dimethoxyphenyl)-4H-chromene;
2-Amino-3-cyano-7-methoxy-4-(3-methoxyphenyl)-4H-chromene;
2-Amino-3-cyano-7-methoxy-4-(3-cyanophenyl)-4H-chromene;
2-Amino-3-cyano-7-methoxy-4-(3-chlorophenyl)-4H-chromene;
2-Amino-3-cyano-7-methoxy-4-(3-nitrophenyl)-4H-chromene;
2-Amino-3-cyano-7-methoxy-4-(3-bromophenyl)-4H-chromene;
2-Amino-3-cyano-7-methoxy-4-(5-methyl-3-pyridyl)-4H-chromene;
2-Amino-3-cyano-7-methoxy-4-(5-methoxy-3-pyridyl)-4H-chromene;
2-Amino-3-cyano-7-methoxy-4-(5-methylthio-3-pyridyl)-4H-chromene;
2-Amino-3-cyano-7-methoxy-4-(5-chloro-3-pyridyl)-4H-chromene;
2-Amino-3-cyano-7-methoxy-4-(5-bromo-3-pyridyl)-4H-chromene;
2-Amino-3-cyano-7-methyl-4-(3-bromo-4,5-dimethoxyphenyl)-4H-chromene;
2-Amino-3-cyano-7-chloro-4-(3-bromo-4,5-dimethoxyphenyl)-4H-chromene;
2-Amino-3-cyano-7-bromo-4-(3-bromo-4,5-dimethoxyphenyl)-4H-chromene;
2-Amino-3-cyano-7-bromo-4-(5-methyl-3-pyridyl)-4H-chromene;
2-Amino-3-cyano-7-chloro-4-(5-methyl-3-pyridyl)-4H-chromene;
2-Amino-3-cyano-7-ethylamino-4-(3-bromo-4,5-dimethoxyphenyl)-4H-chromene;
2-Amino-3-cyano-7-ethylamino-4-(5-methyl-3-pyridyl)-4H-chromene; and
2-Amino-3-cyano-7-hydroxy-4-(3-bromo-4,5-dimethoxyphenyl)-4H-chromene.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which can be optionally substituted.

Useful alkoxy groups include oxygen substituted by one of the $C_{1-10}$ alkyl groups mentioned above, which can be optionally substituted.

Useful alkylthio groups include sulphur substituted by one of the $C_{1-10}$ alkyl groups mentioned above, which can be optionally substituted. Also included are the sulfoxides and sulfones of such alkylthio groups.

Useful amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group can be optionally substituted.

Optional substituents on the alkyl groups include one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl($C_2$–$C_6$)alkenyl, $C_6$–$C_{10}$ aryl($C_2$–$C_6$)alkynyl, saturated and unsaturated heterocyclic or heteroaryl. Optional substituents on the aryl, aralkyl and heteroaryl groups include one or more halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy or carboxy.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Preferably the arylalkyl group is benzyl, phenethyl or naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyriridinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[11,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

Certain of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy, Tris(hydroxymethyl) aminomethane (TRIS, tromethane) and N-methylglucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof such as succinic and fumaric anhydrides according to methods known in the art); imines of amino containing compounds (e.g., those obtained by condensation with a $C_{1-4}$ aldehyde or ketone according to methods known in the art); carbamate of amino containing compounds such as those described by Leu, et. al., (J. Med. Chem. 42:3623–3628 (1999)) and Greenwald, et. al., (J. Med. Chem. 42:3657–3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I–IV can be prepared as illustrated by exemplary reaction in Scheme 1. Reaction of a phenol with a benzaldehyde and malononitrile in the presence a base such as piperidine or N,N-diisopropylethylamine produced the substituted chromene. The reaction also can be run by reacting an aldehyde with malononitrile in the presence a base such as piperidine first, the intermediate was then treated with a phenol and cyclized to give the final product as shown by exemplary reactions in Scheme 2. The 2-amino group can be modified by acylation to give the amide as shown by exemplary reaction in Scheme 3.

Scheme 1

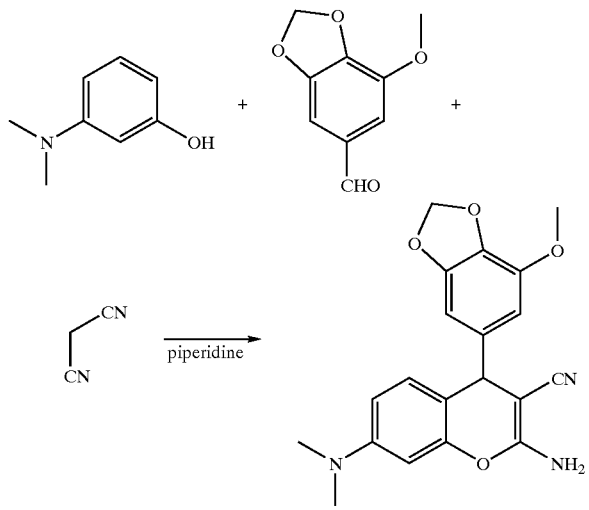

Scheme 2

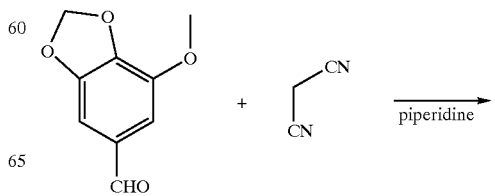

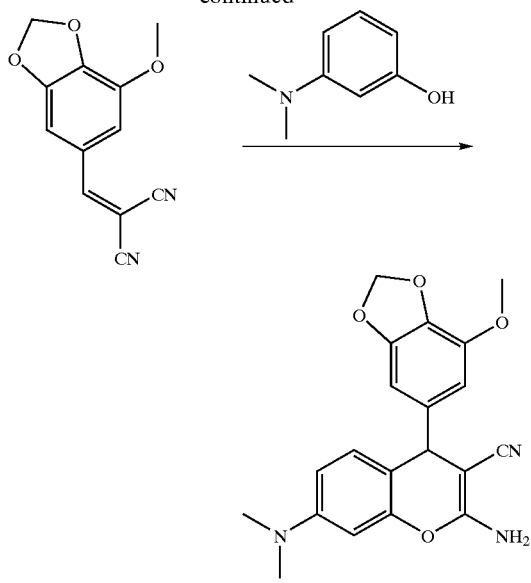

Scheme 3

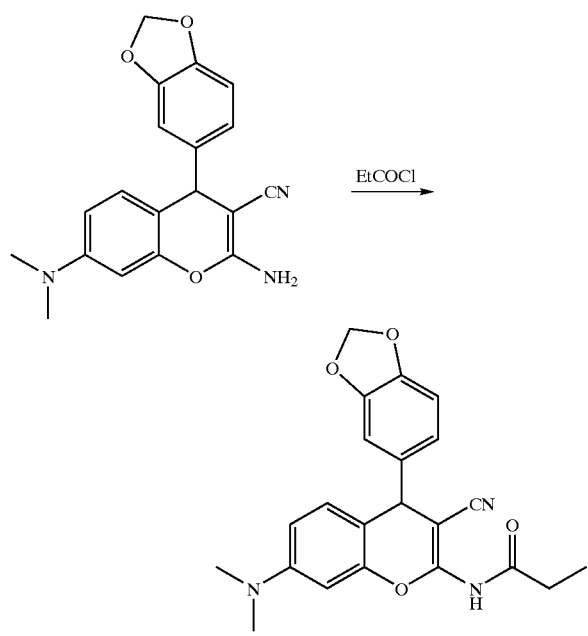

An important aspect of the present invention is the discovery that compounds having Formula I–IV are activators of caspases and inducers of apoptosis. Therefore, these compounds are expected to be useful in a variety of clinical conditions in which there is uncontrolled cell growth and spread of abnormal cells, such as in the case of cancer.

Another important aspect of the present invention is the discovery that compounds having Formula I–IV are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are expected to be useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I–IV, which functions as a caspase cascade activator and inducer of apoptosis.

The present invention also include a therapeutic method comprising administering to an animal an effective amount of a compound, or a pharmaceutically acceptable salt or prodrug of said compound of Formulae I–IV, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

Another embodiment of the present invention is directed to a composition effective to inhibit neoplasia comprising a compound, or a pharmaceutically acceptable salt or prodrug of said compound of Formulae I–IV, which functions as a caspase cascade activator and inducer of apoptosis, in combination with at least one known cancer chemotherapeutic agent, or a pharmaceutically acceptable salt of said agent. Examples of known anti-cancer agents which can be used for combination therapy include, but are not limited to, alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from the at least one known cancer chemotherapeutic agent. In one embodiment, the compound of the invention and the at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and the at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugate of said compound of Formulae I–IV, which functions as a caspase cascade activator and inducer of apoptosis, in bioconjugation with at least one known therapeutically useful antibody, such as Herceptin® or Rituxan®, growth factors such as DGF, NGF, cytokines such as IL-2, IL-4, or any molecule that binds to the cell surface. The antibodies and other molecules will deliver compound of Formulae I–V to its target and make them effective anticancer agents. The bioconjugates also could enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of said compound of Formulae I–IV, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I–IV, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13–21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133:629–633 (1998) and Vaishnaw, A. K, et al., *J. Clin. Invest.* 103:355–363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475–483 (1998)). It is therefore evident that many types of autoimmune disease are caused by defects of the apoptotic process, and one treatment strategy would be to turn on apoptosis in the lymphocytes that are causing autoimmune disease (O'Reilly, L. A. & Strasser, A., *Inflamm. Res.* 48:5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603–608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, and both of which were resistant to apoptosis induced by anti-Fas antibody in the absence of bisindolylmaleimide VII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42–48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore the application of a Fas-dependent apoptosis enhancer such as bisindolylmaleimide VIII may be therapeutically useful for the more effective elimination of detrimental cells and inhibition of T cell-mediated autoimmune diseases. Therefore an effective amount of a compound, or a pharmaceutically acceptable salt or prodrug of the compound of Formulae I–IV, which functions as a caspase cascade activator and inducer of apoptosis, should be an effective treatment for autoimmune disease.

Psoriasis is a chronic skin disease that is characterized by scaly red patches. Psoralen plus ultraviolet A (PUVA) is a widely used and effective treatment for psoriasis vulgaris and Coven, et al., *Photodermatol. Photoimmunol. Photomed.* 15:22–27 (1999), reported that lymphocytes treated with psoralen 8-MOP or TMP plus UVA displayed DNA degradation patterns typical of apoptotic cell death. Ozawa, et at, *J. Exp. Med.* 189:711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240–245 (1998), reported that low doses of methotrexate may induce apoptosis and this mode of action could explain the reduction in epidermal hyperplasia during treatment of psoriasis with methotrexate. Therefore an effective amount of a compound, or a pharmaceutically acceptable salt or prodrug of the compound of Formulae I–IV, which functions as a caspase cascade activator and inducer of apoptosis, should be an effective treatment for psoriasis.

Synovial cell hyperplasia is a characteristic of patients with rheumatoid arthritis (RA). Excessive proliferation of RA synovial cells as well as defective in synovial cell death might be responsible for the synovial cell hyperplasia. Wakisaka, et al, *Clin. Exp. Immunol.* 114:119–128 (1998), found that although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells, and lead to pannus formation and the destruction of joints in patients with RA. Therefore an effective amount of a compound, or a pharmaceutically acceptable salt or prodrug of the compound of Formulae I–IV, which functions as a caspase cascade activator and inducer of apoptosis, should be an effective treatment for rheumatoid arthritis.

There have been accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375–380 (1997)). Boirivant, et al., *Gastroenterology* 116:557–565 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore an effective amount of a compound, or a pharmaceutically acceptable salt or prodrug of the compound of Formulae I–IV, which functions as a caspase cascade activator and inducer of apoptosis, should be an effective treatment for inflammation and inflammatory bowel disease.

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day of the body weight of the mammal being treated for apoptosis-mediated disorders. Preferably, about 0.01 to about 10 mg/kg is orally administered to treat or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg. If a known cancer chemotherapeutic agent is also administered, it is administered in an amount with is effective to achieve its intended purpose. The amounts of such known cancer chemotherapeutic agents effective for cancer are well known to those of skill in the art.

The unit oral dose may comprise from about 0.01 to about 50 mg, preferably about 0.1 to about 10 mg of the compound of the invention. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400) or cremophor, or cyclodextrins. Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Example 1

2-Amino-3-cyano-7-dimethylamino-4-(3,4-methylenedioxyphenyl)-4H-chromene

To a mixture of 3-dimethylaminophenol (489 mg, 3.56 mmol), piperonal (535 mg, 3.56 mmol), and malononitrile (233 mg, 3.53 mmol) in ethanol (20 ml) was added piperidine (0.70 ml, 7.1 mmol). The mixture was stirred at room temperature for 2 h and the resulting solid was collected by filtration, washed with methanol and dried in vacuo to yield the title compound as a yellow solid (940 mg, 2.80 mmol, 79%). $^1$H NMR (DMSO-$d_6$): 6.83–6.77 (m, 4H), 6.66–6.64 (m, 2H), 6.47–6.44 (m, 1H), 6.21 (s, 1H), 5.96 (s, 1H), 5.95 (s, 1H), 4.53 (s, 1H), 2.85 (s, 6H).

Example 2

2-Amino-3-cyano-7-dimethylamino-4-(2-naphthyl)-4H-chromene

The title compound was prepared as a tan solid from 2-naphthylaldehyde in 73% yield as described in Example 1. $^1$H NMR (DMSO-$d_6$): 7.89–7.81 (m, 3H), 7.74 (s, 1H), 7.52–7.44 (m, 2H), 7.23–7.20 (m, 1H), 6.89 (s, 2H), 6.77 (d, J=8.7, 1H), 6.43–6.40 (m, 1H), 6.25 (s, 1H), 4.76 (s, 1H), 2.84 (s, 6H).

Example 3

3-Cyano-7-dimethylamino-4-(3,4-methylenedioxyphenyl)-2-propionamido-4H-chromene

To a solution of 2-amino-3-cyano-7-dimethylamino-4-(3,4-methylenedioxyphenyl)-4H-chromene (102 mg, 0.30 mmol) in dichloromethane (5 ml) was added pyridine (0.7 ml) at 0° C., followed by propionyl chloride (0.3 ml). The mixture was then stirred at room temperature for 4 h, diluted with 1:1 hexane/EtOAc (80 ml), washed with water, 2N HCl, water and brine, dried over sodium sulfate and concentrated in vacuo. The residue was purified by chromatography (4:1 hexane/EtOAc) to yield the title compound as a yellow solid (16 mg, 14%). $^1$H NMR (CDCl$_3$): 6.85–6.76 (m, 4H), 6.51–6.48 (m, 1H), 6.31 (m, 1H), 6.00–5.95 (m, 2H), 4.80 (s, 1H), 2.95 (s, 6H), 2.31 (q, J=7.5, 2H), 1.14 (t, J=7.5, 3H).

Example 4

2-Amino-3-cyano-7-dimethylamino-4-(4-methyl-3-nitropheyl)-4H-chromene

The title compound was prepared as a gray solid from 4-methyl-3-nitrobenzaldehyde in 60% yield as described in Example 1. $^1$H NMR (CDCl$_3$): 7.78 (d, J=2.1, 1H), 7.40 (d, J=2.1, 1H), 7.37 (d, J=2.1, 1H), 6.75–6.72 (m, 1H), 6.44–6.40 (m, 1H), 6.30 (d, J=2.1, 1H), 4.72 (s, 1H), 4.62 (bs, 2H), 2.94 (s, 6H), 2.56 (s, 3H).

Example 5

2-Amino-3-cyano-7-diethylamino-4-(3-methoxy-4,5-methylenedioxyphenyl)-4H-chromene The title compound was prepared as a yellow solid from 5-methoxypiperonal and 3-(diethylamino)phenol as described in Example 1. $^1$H NMR (CDCl$_3$): 6.79–6.76 (m, 1H), 6.44 (d, J=1.2, 1H), 6.39–6.36 (m, 1H), 6.33 (d, J=1.8, 1H), 6.22 (d, J=2.7, 1H), 5.93–5.91 (m, 2H), 4.54 (s, 2H), 4.53 (s, 1H), 3.90 (s, 3H), 3.31 (q, J=7.2, 4H), 1.14 (t, J=7.2, 6H).

Example 6

2-Amino-3-cyano-7-dimethylamino-4-(4-carboxyphenyl)-4H-chromene

The title compound was prepared as a brown solid from 4-carboxybenzaldehyde as described in Example 1. $^1$H NMR (DMSO-d$_6$): 7.80 (d, J=8.4, 2H), 7.14 (d, J=8.4, 2H), 6.86 (s, 2H), 6.78 (d, J=8.4, 2H), 6.47–6.43 (m, 1H), 6.23 (d, J=2.4, 1H), 4.63 (s, 1H), 2.86 (s, 6H).

Example 7

2-Amino-3-cyano-7-dimethylamino-4-(4N-oxide-pyridyl)-4H-chromene

The title compound was prepared as a brown solid from 4-pyridinecarboxaldehyde N-oxide as described in Example 1. $^1$H NMR (CDCl$_3$): 8.14 (d, J=7.2, 2H), 7.11 (d, J=7.2, 2H), 6.74 (d, J=9.0, 1H), 6.48–6.44 (m, 1H), 6.30 (d, J=2.7), 4.69 (s, 2H), 4.67 (s, 1H), 2.96 (s, 6H).

Example 8

2-Amino-3-cyano-7-dimethylamino-4-(2-imidazolyl)-4H-chromene

The title compound was prepared as a gray solid from imidazole-2-carboxaldehyde as described in Example 1. $^1$H NMR (DMSO-d$_6$): 6.96 (s, 1H), 6.86–6.84 (m, 3H), 6.74 (s, 1H), 6.48–6.44 (m, 1H), 6.20 (d, J=2.4, 1H), 4.74 (s, 1H), 2.85 (s, 6H).

Example 9

2-Amino-3-cyano-7-dimethylamino-4-(3-pyridyl)-4-chromene

The title compound was prepared as a brown solid from 3-pyridinecarboxaldehyde as described in Example 1. $^1$H NMR (CDCl$_3$): 8.49–8.47 (m, 2H), 7.52–7.49 (m, 1H), 7.26–7.22 (m, 1H), 6.75 (d, J=8.7, 1H), 6.45–6.41 (m, 1H), 6.30 (d, J=2.4, 1H), 4.69 (s, 1H), 4.62 (s, 2H), 2.93 (s, 6H).

Example 10

2-Amino-3-cyano-7-dimethylamino-4-(3-bromo-4,5-dimethoxyphenyl)-4H-chromene

The title compound was prepared as an off-white solid from 5-bromoveratraldehyde as described in Example 1. $^1$H NMR (CDCl$_3$): 6.89 (d, J=1.8, 1H), 6.79 (d, J=8.7, 1H), 6.72 (d, J=1.8, 1H), 6.46–6.43 (m, 1H), 6.28 (d, J=2.7, 1H), 4.58 (s, 1H), 4.57 (s, 2H), 3.84 (s, 3H), 3.83 (s, 3H), 2.94 (s, 6H).

Example 11

2-Amino-3-cyano-7-dimethylamino-4-(3,4-ethylenedioxyphenyl)-4H-chromene

The title compound was prepared as a grey solid from 1,4-benzodioxan-6-carboxaldehyde as described in Example 1. $^1$H NMR (CDCl$_3$): 6.83–6.77 (m, 2H), 6.71–6.67 (m, 2H), 6.45–6.41 (m, 1H), 6.27 (d, J=2.4, 1H), 4.54 (s, 1H), 4.52 (s, 2H), 4.22 (s, 4H), 2.92 (s, 6H).

Example 12

2-Amino-3-cyano-7-dimethylamino-4-(3,4-dimethoxyphenyl)-4H-chromene

The title compound was prepared as an off-white solid from 3,4-dimethoxybenzaldehyde as described in Example 1. $^1$H NMR (CDCl$_3$): 6.81 (s, 1H), 6.79 (s, 1H), 6.75 (d, J=1.8, 1H), 6.69 (d, J=1.8, 1H), 6.45–6.41 (m, 1H), 6.29 (d, J=3.0, 1H), 4.60 (s, 1H), 4.54 (s, 2H), 3.85 (s, 3H), 3.83 (s, 3H), 2.93 (s, 6H).

Example 13

2-Amino-3-cyano-5,7-dimethoxy-4-(3-methoxy-4,5-methylenedioxyphenyl)-4H-chromene The title compound was prepared as a yellow solid from 5-methoxypiperonal and 3,5-dimethoxyphenyl as described in Example 1. $^1$H NMR (CDCl$_3$): 6.43 (d, J=1.5, 1H), 6.27 (d, J=1.5, 1H), 6.20 (s, 2H), 5.92–5.90 (m, 2H), 4.61 (s, 1H), 4.51 (s, 2H), 3.88 (s, 3H), 3.79 (s, 3H), 3,67 (s, 3H).

Example 14

2-Amino-3-cyano-4-(3-methoxy-4,5-methylenedioxyphenyl)-6,7-methylenedioxy-4H-chromene The title compound was prepared as a light yellow solid from 5-methoxypiperonal and sesamol as described in Example 1. $^1$H NMR (CDCl$_3$): 6.51 (s, 1H), 6.40 (d, J=1.2, 1H), 6.38 (d, J=0.6, 1H), 6.31 (d, J=1.5, 1H), 5.95–5.91(m, 4H), 4.55 (s, 2H), 4.52 (s, 1H), 3.90 (s, 3H).

Example 15

2-Amino-3-cyano-6,7-dimethoxy-4-(3-methoxy-4,5-methylenedioxyphenyl)-4H-chromene The title compound was prepared as a light yellow solid from 5-methoxypiperonal and 3,4-dimethoxyphenol as described in Example 1. $^1$H NMR (CDCl$_3$): 6.54 (s, 1H), 6.41 (d, J=1.8, 1H), 6.38 (s, 1H), 6.31 (d, J=1.8, 1H), 5.95–5.94 (m, 2H), 4.57 (s, 1H), 4.54 (s, 2H), 3.90 (s, 3H), 3.87 (s, 3H), 3.74 (s, 3H).

Example 16

2-Amino-3-cyano-7-dimethylamino-4-(2-chloro-3-quinolyl)-4H-chromene

The title compound was prepared as a yellow solid from 2-chloro-3-quinolinecarboxaldehyde as described in Example 1. $^1$H NMR (CDCl$_3$): 8.02 (s, 1H), 7.99 (s, 1H), 7.77–7.68 (m, 2H), 7.55–7.50 (m, 1H), 6.88 (d, J=9.0, 1H), 6.41–6.38 (m, 1H), 6.31 (d, J=2.4, 1H), 5.36 (s, 1H), 4.70 (s, 1H), 2.93 (s, 6H).

Example 17

2-Amino-3-cyano-7-dimethylamino-4-(5-chloro-2-nitrophenyl)-4H-chromene

The title compound was prepared as a yellow solid from 5-chloro-2-nitrobenzaldehyde as described in Example 1. $^1$H NMR (DMSO-$_6$): 7.95 (d, J=8.7, 1H), 7.59–7.55 (m, 1H), 7.26 (d, J=2.1, 1H), 7.05 (s, 2H), 6.79 (d, J=8.7, 1H), 6.50–6.46 (m, 1H), 6.26 (d, J=3.0, 1H), 5.19 (s, 1H), 2.89 (s, 6H).

Example 18

2-Amino-3-cyano-7-dimethylamino-4-(2-chloro-5-nitrophenyl)-4H-chromene

The title compound was prepared as a yellow solid from 2-chloro-5-nitrobenzaldehyde as described in Example 1. $^1$H NMR (CDCl$_3$): 8.03–8.00 (m, 2H), 7.55 (d, J=9.6, 1H), 6.78 (d, J=8.7, 1H), 6.42–6.39 (m, 1H), 6.31 (d, J=2.4, 1H), 5.41 (s, 1H), 4.70 (s, 2H), 2.94 (s, 6H).

Example 19

2-Amino-3-cyano-7-dimethylamino-4-(3-methoxy-4,5-methylenedioxyphenyl)-4H-chromene

To a mixture of 3-dimethylaminophenol (761 mg, 5.5 mmol), 5-methoxypiperonal (1.0 g, 5.5 mmol), and malononitrile (367 mg, 5.5 mmol) in ethanol (20 ml) was added piperidine (1.2 ml, 11.1 mmol). The mixture was stirred at room temperature overnight and the solvent was evaporated. The resulting solid was collected by filtration, and washed with diethyl ether. The solid was recrystallized in DMSO/water to give the title compound as a light brown solid (1.5 g, 4.1 mmol, 74%). $^1$H NMR (DMSO-d$_6$): 6.85 (s, 1H), 6.82 (s, 2H), 6.52 (d, J=1.5, 1H), 6.49–6.45 (m, 1H), 6.29 (d, J=1.5, 1H), 6.21 (d, J=2.7, 1H), 5.94 (d, J=6.3, 2H), 4.54 (s, 1H), 3.81 (s, 3H), 2.86 (s, 6H).

Example 20

2-Amino-3-cyano-7-dimethylamino-4-(2-bromo-4,5-dimethoxyphenyl)-4H-chromene

The title compound was prepared from 6-bromoveratraldehyde as described in Example 19. $^1$H NMR (DMSO$_6$): 7.10 (s, 1H), 6.87 (s, 2H), 6.72 (d, J=9.0, 1H), 6.66 (s, 1H), 6.47–6.43 (m, 1H), 6.21 (d, J=2.4, 1H), 5.03 (s, 1H), 3.77 (s, 3H), 3.63 (s, 3H), 2.86 (s, 6H).

Example 21

2-Amino-3-cyano-7-dimethylamino-4-(2-chloro-4,5-methylenedioxyphenyl)-4H-chromene

The title compound was prepared from 6-chloropiperonal in a yield of 80% as described in Example 1. $^1$H NMR (DMSO-d$_6$): 7.03 (s, 1H), 6.87 (s, 2H), 6.72 (d, J=8.7, 1H), 6.59 (s, 1H), 6.48–6.44 (m, 1H), 6.22 (d, J=2.4, 1H), 6.05 (s, 1H), 6.01 (s, 1H), 5.04 (s, 1H), 2.86 (s, 6H).

Example 22

2-Amino-3-cyano-7-dimethylamino-4-(2,4,5-trimethoxyphenyl)-4H-chromene

The title compound was prepared from 2,4,5-trimethoxybenzaldehyde as described in Example 19. $^1$H NMR (DMSO-d$_6$): 6.80 (d, J=8.7, 1H), 6.71 (s, 2H), 6.68 (s, 1H), 6.55 (s, 1H), 6.44–6.40 (m, 1H), 6.20 (d, J=2.4, 1H), 4.88 (s, 1H), 3.76 (d, J=3.9, 6H), 3.59 (s, 3H), 2.84 (s, 6H).

Example 23

2-Amino-3-cyano-7-dimethylamino-4-(2,3,4-trimethoxyphenyl)-4H-chromene

The title compound was prepared from 2,3,4-trimethoxybenzaldehyde as described in Example 19. $^1$H NMR (DMSO-d$_6$): 6.73–6.71 (m, 5H), 6.45–6.41 (m, 1H), 6.22 (d, J=2.4, 1H), 4.74 (s, 1H), 3.74 (d, J=5.1, 6H), 3.66 (s, 3H), 2.85 (s, 6H).

Example 24

2-Amino-3-cyano-7-dimethylamino-4-(3,4,5-trimethoxphenyl)-4H-chromene

The title compound was prepared from 3,4,5-trimethoxybenzaldehyde in a yield of 78% as described in Example 1. $^1$H NMR (DMSO-d6): 6.90–6.94 (m, 3H), 6.48–6.46 (m, 3H), 6.23 (s, 1H), 4.57 (s, 1H), 3.72 (s, 3H), 2.87 (s, 6H).

Example 25

2-Amino-3-cyano-7-dimethylamino-4-(2,3-dimethoxyphenyl)-4H-chromene

The title compound was prepared from 2,3-dimethoxybenzaldehyde as described in Example 19. $^1$H NMR (DMSO-d$_6$): 6.98 (t, J=7.2, 1H), 6.88 (d, J=7.5, 1H), 6.77 (s, 2H), 6.72 (d, J=8.4, 1H), 6.61 (d, J=7.2, 1H), 6.44–6.40 (m, 1H), 6.22 (d, J=1.8, 1H), 4.86 (s, 1H), 3.79 (s, 3H), 3.65 (s, 3H), 2.85 (s, 6H).

Example 26

2-Amino-3-cyano-7-dimethylamino-4-(2,4-dimethoxyphenyl)-4H-chromene

The title compound was prepared from 2,4-dimethoxybenzaldehyde as described in Example 19. $^1$H NMR (DMSO-d$_6$): 6.85 (d, J=8.4, 1H), 6.80 (d, J=8.7, 1H), 6.71 (s, 2H), 6.54 (d, J=2.4, 1H), 6.47–6.40 (m, 2H), 6.19 (d, J=2.1, 1H), 4.88 (s, 1H), 3.78 (s, 3H), 3.72 (s, 3H), 2.84 (s, 6H).

Example 27

2-Amino-3-cyano-7-dimethylamino-4-(4-tert-butylphenyl)-4H-chromene

The title compound was prepared from 4-tert-butylbenzaldehyde in a yield of 50% as described in Example 1. $^1$H NMR (DMSO-d$_6$): 7.31 (d, J=8.1, 2H), 7.07 (d, J=8.7, 1H), 6.82 (s, 2H), 6.78 (s, 1H), 6.47–6.46 (m, 1H), 6.23 (d, J=2.1, 1H), 4.55 (s, 1H), 2.86 (s, 6H), 1.24 (s, 9H).

Example 28

2-Amino-3-cyano-7-dimethylamino-4-(3,4-dimethylphenyl)-4H-chromene

The title compound was prepared from 3,4-methylbenzaldehyde in a yield of 29% as described in Example 1. $^1$H NMR (DMSO-$d_6$): 7.04 (d, J=7.5, 1H), 6.90–6.86 (m, 2H), 6.77 (d, J=3.3, 2H), 6.73 (s, 1H), 6.45–6.42 (m, 1H), 6.21(d, J=2.7, 1H), 4.50 (s, 1H), 2.85 (s, 6H), 2.16 (s, 6H).

Example 29

2-Amino-3-cyano-7-dimethylamino-4-(3,5-dimethylphenyl)-4H-chromene

The title compound was prepared from 3,5-dimethylbenzaldehyde as described in Example 19. $^1$H NMR (DMSO-$d_6$): 6.82–6.75 (m, 6H), 6.46–6.42 (m, 1H), 6.22 (d, J=2.4, 1H), 4.50 (s, 1H), 2.86 (s, 6H), 2.22 (s, 6H).

Example 30

2-Amino-3-cyano-7-dimethylamino-4-(2-fluoro-5-methoxyphenyl)-4H-chromene

The title compound was prepared from 2-fluoro-5-methoxy-benzaldehyde. The resulting reaction solution was purified by column chromatography to give the title compound as light yellow solid. $^1$H NMR (DMSO-$d_6$): 7.07 (t, J=9.9, 1H), 6.90 (s, 2H), 6.84–6.78 (m, 2H), 6.71–6.68 (m, 1H), 6.48–6.45 (m, 1H), 6.23 (d, J=1.8, 1H), 4.81 (s, 1H), 3.69 (s, 3H), 2.86 (s, 6H).

Example 31

2Amino-3-cyano-7-dimethylamino-4-phenyl-4H-chromene

The title compound was prepared from benzaldehyde in a yield of 74% as described in Example 1. $^1$H NMR (DMSO-$d_6$): 7.32–7.27 (m, 2H), 7.22–7.14 (m, 3H), 6.82 (s, 2H), 6.78 (d, J=8.7, 1H), 6.47–6.43 (m, 1H), 6.23 ( d, J=2.4, 1H), 4.59 (s, 1H), 2.86 (s, 6H).

Example 32

2-Amino-3-cyano-7-dimethylamino-4-(2-fluro-3-trifluoromethylphenyl)-4H-chromene

The title compound was prepared from 2-fluoro-3-trifluoromethyl-benzaldehyde with N,N-diisopropylethylamine and was isolated as a pale yellow solid in a yield of 84% as described in Example 30. $^1$H NMR (DMSO-$d_6$): 7.66 (t, J=7.2, 1H), 7.54 (t, J=7.2, 1H), 7.38 (t, J=7.2, 1H), 6.99 (s, 2H), 6.79 (d, J=8.7, 1H), 6.50–6.46 (m, 1H), 6.25 (d, J=2.4, 1H), 5.02 (s, 1H), 2.88 (s, 6H).

Example 33

2-Amino-3-cyano-7-dimethylamimo-4-(4-fluro-3-trifluoromethylphenyl)-4H-chromene

The title compound was prepared from 4-fluoro-3-trifluoromethyl-benzaldehyde as a light yellow solid in a yield of 4% as described in Example 32. $^1$H NMR (DMSO-$d_6$): 7.59 (d, J=7.8, 1H), 7.50–7.44 (m, 2H), 6.99 (s, 2H), 6.79 (d, J=8.4, 1H), 6.49–6.46 (m, 1H), 6.24 (d, J=2.1, 1H), 4.83 (s, 1H), 2.87 (s, 6H).

Example 34

2-Amino-3-cyano-7-dimethylamino-4-(2,4,5-triflourophenyl)-4H-chromene

The title compound was prepared from 2,4,5-trifluorobenzaldehyde as a pale yellow solid in a yield of 14% as described in Example 32. $^1$H NMR (DMSO-$d_6$): 7.55–7.46 (m, 1H), 7.34–7.25 (m, 1H), 6.95 (s, 2H), 6.79 (d, J=8.7, 1H), 6.49–6.45 (m, 1H), 6.23 (d, J=2.4, 1H), 4.87 (s, 1H), 2.87 (s, 6H).

Example 35

2-Amino-3-cyano-7-dimethylamino-4-(2,3,4-trifluorophenyl)-4H-chromene

The title compound was prepared from 2,3,4-trifluorobenzaldehyde as a white solid in a yield of 14% as described in Example 32. $^1$H NMR (DMSO-$d_6$): 7.32–7.24 (m, 1H), 7.07–7.02 (m, 1H), 6.99 (s, 2H), 6.80 (d, J=8.4, 1H), 6.49–6.46 (m, 1H), 6.23 (d, J=2.4, 1H), 4.94 (s, 1H), 2.87 (s, 6H).

Example 36

2-Amino-3-cyano-7-dimethylamino-4-(2-fluoro-5-nitrophenyl)-4H-chromene

The title compound was prepared from 2-fluoro-5-nitrobenzaldehyde as a yellow solid in a yield of 13% as described in Example 32. $^1$H NMR (DMSO-$d_6$): 8.23–8.17 (m, 1H), 8.13–8.10 (m, 1H), 7.48 (t, J=9.9, 1H), 7.04 (s, 2H), 6.83 (d, J=8.7, 1H), 6.49–6.45 (m, 1H), 6.26 (d, J=2.4, 1H), 5.07 (s, 1H), 2.88 (s, 6H).

Example 37

2-Amino-3-cyano-7-dimethylamino-4-(4-chloro-3-nitrophenyl)-4H-chromene

The title compound was prepared from 4-chloro-3-nitrobenzaldehyde as a yellow solid in a yield of 25% as described in Example 1. $^1$H NMR (CDCl$_3$): 7.65 (d, J=1.8, 1H), 7.49 (d, J=8.1, 1H), 7.42–7.38 (m, 1H), 6.72 (d, J=8.4, 1H), 6.45–6.42 (m, 1H), 6.30 (d, J=2.4, 1H), 4.73 (s, 1H), 4.68 (s, 2H), 2.95 (s, 6H).

Example 38

2-Amino-3-cyano-7-dimethylamino-4-(3-nitrophenyl)-4H-chromene

The title compound was prepared from 3-nitrobenzaldehyde as a yellow solid in a yield of 46% as described in Example 1. $^1$H NMR (DMSO-$d_6$): 8.10 (d, J=7.2, 1H), 8.02 (s, 1H), 7.65–7.63 (m, 2H), 7.03 (s, 2H), 6.83 (d, J=8.7, 1H), 6.49–6.46 (m, 1H), 6.26 (d, J=2.1, 1H), 4.89 (s, 1H), 2.87 (s, 6H).

Example 39

2-Amino-3-cyano-7-dimethylamino-4-cyclohexyl-4H-chromene

The title compound was prepared from cyclohexanecarboxaldehyde as a pale yellow solid in a yield of 31% as described in Example 30. $^1$H NMR (1DMSO-$d_6$): 6.96 (d, J=8.4, 1H), 6.72 (s, 2H), 6.53–6.49 (m, 1H), 6.20 (d, J=2.4, 1H), 3.19 (d, J=3.3, 1H), 2.87 (s, 6H), 2.82 (s, 1H), 1.65–0.86 (m, 10H).

Example 40

2-Amino-7-dimethylamino-3-ethoxycarbonyl-4-(3-methoxy-4,5-methylenedioxy)phenyl-4H-chromene

The title compound was prepared as a tan solid from ethyl cyanoacetate in 25% yield as described in Example 1. $^1$H NMR (DMSO-d₆): 6.94 (d, J=8.4, 1H), 6.45–6.23 (m, 6H), 5.88–5.86 (m, 2H), 4.75 (s, 1H), 4.08 (q, J=7.0, 2H), 3.87 (s, 3H), 2.91 (s, 6H), 1.20 (t, J=7.0, 3H).

Example 41

2-Amino-3-cyano-7-dimethylamino-4-(3-fluoro-4-trifluoromethylphenyl)-4H-chromene The title compound was prepared from 3-fluoro-4-trifluoromethyl-benzaldehyde as a yellow solid as described in Example 19. ¹H NMR (DMSO-d₆): 7.75 (t, J=7.65, 1H), 7.33 (d, J=11.4, 1H), 7.20 (d, J=8.4, 1H), 7.02 (s, 2H), 6.83 (d, J=8.7, 1H), 6.50–6.46 (m, 1H), 6.24 (d, J=2.4, 1H), 4.81 (s, 1H), 2.87 (s, 6H).

Example 42

2-Amino-3-cyano-7-dimethylamino-4-(3,4-difluoro-5-trifluoromethylphenyl)-4H-chromene The title compound was prepared from 3,4-difluoro-5-trifluoromethyl-benzaldehyde as a white solid in a yield of 50% as described in Example 1. ¹H NMR (DMSO-d₆): 7.65–7.60 (m, 1H), 7.44 (d, J=5.1, 1H), 7.05 (s, 2H), 6.83 (d, J=8.7, 1H), 6.51–6.47 (m, 1H), 6.24 (d, J=2.7, 1H), 4.86 (s, 1H), 2.88 (s, 6H).

Example 43

2-Amino-3-cyano-7-dimethylamino-4-(2-chloro5-trifluoromethylphenyl)-4H-chromene

The title compound was prepared from 2-chloro-5-trifluoromethyl-benzaldehyde as a light pink solid in a yield of 22% as described in Example 1. ¹H NMR (DMSO-d₆): 7.71–7.66 (m, 2H), 7.55 (s, 1H), 7.00 (s, 2H), 6.72 (d, J=8.7, 1H), 6.45 (d, J=7.5, 1H), 6.25 (s, 1H), 5.23 (s, 1H), 2.87 (s, 6H).

Example 44

2-Amino-3-cyano-7-dimethylamino-4-(3,4-dibenzyloxyphenyl)-4H-chromene

The title compound was prepared from 3,4-dibenzyloxybenzaldehyde as a white solid in a yield of 38% as described in Example 1. ¹H NMR (DMSO-d₆): 7.44–7.31 (m, 10H), 6.99 (d, J=8.4, 1H), 6.92 (d, J=1.8, 1H), 6.79 (s, 1H), 6.75 (d, J=9.0, 1H), 6.69–6.65 (m, 1H), 6.44–6.40 (m, 1H), 6.21 (d, J=2.4, 1H), 5.06–5.05 (m, 4H), 4.52 (s, 1H), 2.86 (s, 6H).

Example 45

2-Amino-3-cyano-7-dimethylamino-4-(3-phenoxyphenyl)-4H-chromene

The title compound was prepared from 3-phenoxybenzaldehyde as a yellow solid in a yield of 10% as described in Example 30. ¹H NMR (DMSO-d₆): 7.41–7.36 (m, 2H), 7.30 (t, J=7.8, 1H), 7.17–7.11 (m, 1H), 7.01–6.98 (m, 2H), 6.93 (d, J=7.5, 1H), 6.86 (s, 3H), 6.83 (d, J=8.4, 1H), 6.79–6.76 (m, 1H), 6.50–6.46 (m, 1H), 6.22 (d, J=2.7, 1H), 4.62 (s, 1H), 2.87 (s, 6H).

Example 46

2-Amino-3-cyano-7-dimethylamino-4-(4-n-octyloxyphenyl)-4H-chromene

The title compound was prepared from 4-n-octyloxybenzaldehyde as a white solid in a yield of 14% as described in Example 1. ¹H NMR (DMSO-d₆): 7.05 (d, J=8.7, 2H), 6.84 (d, J=8.7, 2H), 6.77 (s, 2H), 6.76 (d, J=9.0, 1H), 6.47–6.43 (m, 1H), 6.22 (d, J=2.4, 1H), 4.53 (s, 1H), 3.90 (t, J=6.6, 2H), 2.86 (s, 6H), 1.70–1.65 (m, 2H), 1.38–1.26 (m, 10H), 0.854 (t, J=6.6, 3H).

Example 47

2-Amino-3-cyano-7-dimethylamino-4-(4-n-dodecyloxyphenyl)-4H-chromene

The title compound was prepared from 4-n-dodecyloxybenzaldehyde as a yellow solid in a yield of 65% as described in Example 1. ¹H NMR (DMSO-d₆): 7.04 (d, J=8.4, 2H), 6.85–6.74 (m, 5H), 6.46–6.43 (m, 1H), 6.21 (d, J=2.1, 1H), 4.53 (s, 1H), 3.90 (t, J=6.3, 2H), 2.85 (s, 6H), 1.67–1.65 (m, 2H), 1.24 (s, 18H), 0.84 (t, J=3.6, 3H).

Example 48

2-Amino-3-cyano-7-dimethylamino-4-(5-fluoro-2-nitrophenyl)-4H-chromene

The title compound was prepared from 5-fluoro-2-nitrobenzaldehyde as a yellow solid in a yield of 7% as described in Example 30. ¹H NMR (DMSO-d₆): 8.05–8.00 (m, 1H), 7.39–7.33 (m, 1H), 7.09–7.04 (m, 1H), 7.02 (s, 2H), 6.79 (d, J=8.7, 1H), 6.50–6.46 (m, 1H), 6.25 (d, J=2.4, 1H), 5.23 (s, 1H), 2.88 (s, 6H).

Example 49

2-Amino-3-cyano-7-dimethylamino-4-(4-(4-fluorobenzyloxy)-3-nitrophenyl)-4H-chromene The title compound was prepared from 4-(4-fluorobenzyloxy)-3-nitro-benzaldehyde as a yellow solid in a yield of 31% as described in Example 30. ¹H NMR (DMSO-d₆): 7.69 (d, J=2.1, 1H), 7.52–7.39 (m, 4H), 7.27–7.21 (m, 2H), 6.92 (s, 2H), 6.80 (d, J=9.0, 1H), 6.49–6.46 (m, 1H), 6.23 (d, J=2.4, 1H), 5.25 (s, 2H), 4.74 (s, 1H), 2.87 (s, 6H).

Example 50

2-Amino-3-cyano-7-dimethylamino-4-(4-chloro-3-trifluoromethylphenyl)-4H-chromene The title compound was prepared from 4-chloro-3-trifluoromethyl-benzaldehyde as a white solid in a yield of 46% as described in Example 1. ¹H NMR (DMSO-d₆): 7.68 (d, J=8.4, 2H), 7.46 (d, J=8.4, 1H), 6.98 (s, 2H), 6.80 (d, J=8.7, 1H), 6.49–6.46 (m, 1H), 6.24 (d, J=2.7, 1H), 4.84 (s, 1H), 2.87 (s, 6H).

Example 51

2-Amino-3-cyano-7-dimethylamino-4-(2,3-difluoro-4-trifluoromethylphenyl)-4H-chromene The title compound was prepared from 2,3-difluoro-4-trifluoromethyl-benzaldehyde as a brown solid in a yield of 92% as described in Example 19. ¹H NMR (DMSO-d₆): 7.60 (t, J=7.5, 1H), 7.21 (t, J=7.2, 1H), 7.06 (s, 2H), 6.83 (d, J=8.7, 1H), 6.50–6.46 (m, 1H), 6.26 (d, J=2.4, 1H), 5.07 (s, 1H), 2.88 (s, 6H).

Example 52

2-Amino-3-cyano-7-dimethylamino-4-(2-carboxyphenyl)-4H-chromene

The title compound was prepared from 2-carboxybenzaldehyde as a white solid in a yield of 52% as described in Example 1. ¹H NMR (DMSO-d₆): 7.57 (d, J=6.9, 1H), 7.21–7.14 (m, 2H), 7.07 (t, J=6.9, 1H), 6.99 (d, J=7.8, 1H), 6.66 (s, 2H), 6.40–6.36 (m, 1H), 6.18 (d, J=2.1, 1H), 5.99 (s, 1H), 2.83 (s, 6H).

Example 53

2-Amino-3-cyano-7-dimethylamino-4-(3-carboxyphenyl)-4H-chromene

The title compound was prepared from 3-carboxybenzaldehyde as a yellow solid in a yield of 80% as described in Example 1. ¹H NMR (DMSO-d₆): 7.72–7.68 (m, 1H), 7.64 (s, 1H), 7.29–7.25 (m, 2H), 6.84 (s, 2H), 6.76 (d, J=9.0, 1H), 6.47–6.43 (m, 1H), 6.23 (d, J=2.7, 1H), 4.62 (s, 1H), 2.86 (s, 6H).

Example 54

2-Amino-3-cyano-7-dimethylamino-4-(3,5-dibenzloxyphenyl)-4H-chromene

The title compound was prepared from 3,5-dibenzyloxybenzaldehyde as a white solid in a yield of 58% as described in Example 1. ¹H NMR (DMSO-d₆): 7.45–7.32 (m, 10H), 6.83–6.80 (m, 3H), 6.54–6.53 (m, 1H), 6.46–6.41 (m, 3H), 6.21 (d, J=2.7, 1H), 5.02 (s, 4H), 4.52 (s, 1H), 2.86 (s, 6H).

Example 55

2-Amino-3-cyano-7-dimethylamino-4-(3-(4-methoxyphenoxy)phenyl)-4H-chromene

The title compound was prepared from 3-(4-methoxyphenoxy)benzaldehyde as a white solid in a yield of 12% as described in Example 30. ¹H NMR (DMSO-d₆): 7.24 (t, J=7.8, 1H), 7.01–6.93 (m, 4H), 6.86–6.78 (m, 5H), 6.68–6.64 (m, 1H), 6.50–6.46 (m, 1H), 6.22 (d, J=2.4, 1H), 4.59 (s, 1H), 3.75 (s, 3H), 2.86 (s, 6H).

Example 56

2-Amino-3-cyano-7-dimethylamino-4-(3,5-dimethoxyphenyl)-4H-chromene

The title compound was prepared from 3,5-dimethoxybenzaldehyde as a white solid in a yield of 38% as described in Example 1. ¹H NMR (DMSO-d₆): 6.85 (d, J=8.7, 1H), 6.81 (s, 2H), 6.48–6.44 (m, 1H), 6.36–6.34 (m, 1H), 6.31 (d, J=2.1, 2H), 6.22 (d, J=2.4, 1H), 4.52 (s, 1H), 3.70 (s, 6H), 2.86 (s, 6H).

Example 57

2-Amino-3-cyano-7-dimethylamino-4-(3,5-dichlorophenyl)-4H-chromene

The title compound was prepared from 3,5-dichlorobenzaldehyde as a sandy solid in a yield of 24% as described in Example 19. ¹H NMR (DMSO-d₆): 7.47 (t, J=1.8, 1H), 7.20 (d, J=2.1, 2H), 6.98 (s, 2H), 6.83 (d, J=8.7, 1H), 6.51–6.47 (m, 1H), 6.24 (d, J=2.4, 1H), 4.73 (s, 1H), 2.88 (s, 6H).

Example 58

2-Amino-3-cyano-7-dimethylamino-4-(3-benzyloxyphenyl)-4H-chromene

The title compound was prepared from 3-benzyloxybenzaldehyde in a yield of 76% as described in Example 1. ¹H NMR (DMSO-d₆): 7.46–7.33 (m, 5H), 7.22 (t, J=7.8, 1H), 6.87–6.74 (m, 6H), 6.46–6.43 (m, 1H), 6.22 (d, J=2.1, 1H), 5.04 (s, 2H), 4.56 (s, 1H), 2.86 (s, 6H).

Example 59

2-Amino-3-cyano-7-dimethylamino-4-(5-fluoro-2-trifluoromethylphenyl)-4H-chromene The title compound was prepared from 5-fluoro-2-trifluoromethyl-benzaldehyde as a brown solid in a yield of 21% as described in Example 19. ¹H NMR (DMSO-d₆): 7.84–7.79 (m, 1H), 7.32–7.27 (m, 1H), 7.01 (s, 2H), 6.98–6.94 (m, 1H), 6.59 (d, J=9.0, 1H), 6.49–6.45 (m, 1H), 6.28 (d, J=2.4, 1H), 4.95 (s, 1H), 2.88 (s, 6H).

Example 60

2-Amino-3-cyano-7-dimethylamino-4-(3-dodecyloxyphenyl)-4H-chromene

The title compound was prepared from 3-dodecyloxybenzaldehyde as a white solid in a yield of 54% as described in Example 1. ¹H NMR (DMSO-d₆): 7.19 (t, J=7.8, 1H), 6.83–6.69 (m, 6H), 6.47–6.43 (m, 1H), 6.22 (d, J=2.7, 1H), 4.55 (s, 1H), 3.90 (t, J=6.3, 2H), 2.86 (s, 6H), 1.70–1.65 (m, 2H), 1.38–1.24 (m, 18H), 0.85 (t, J=6.6, 3H).

Example 61

2-Amino-3-cyano-7-dimethylamino-4-(4-carboxaldehydephenyl)-4H-chromene

The title compound was prepared from terephthaldicarboxaldehyde as a yellow solid in a yield of 2% as described in Example 30. ¹H NMR (DMSO-d₆): 9.96 (s, 1H), 7.86 (d, J=8.1, 2H), 7.39 (d, J=7.8, 2H), 6.93 (s, 2H), 6.79 (d, J=8.7, 1H), 6.48–6.44 (m, 1H), 6.25 (d, J=2.7, 1H), 4.75 (s, 1H), 2.87 (s, 6H).

Example 62

2-Amino-3-cyano-7-dimethylamino-4-(2-quinolyl)-4H-chromene

The title compound was prepared from 2-quinolinecarboxaldehyde as a pale pink solid in a yield of 31% as described in Example 1. ¹H NMR (DMSO-d₆): 8.29 (d, J=8.7, 1H), 8.02 (d, J=8.4, 1H), 7.93 (d, J=8.4, 1H), 7.76 (t, J=7.5, 1H), 7.58 (t, J=7.8, 1H), 7.28 (d, J=8.4, 1H), 7.02 (s, 1H), 6.83 (d, J=8.4, 1H), 6.44–6.40 (m, 1H), 6.28 (d, J=2.4, 1H), 4.89 (s, 1H), 2.86 (s, 6H).

Example 63

2-Amino-3-cyano-7-dimethylamino-4-(3-quinolyl)-4H-chromene

The title compound was prepared from 3-quinolinecarboxaldehyde as a yellow solid in a yield of 69% as described in Example 1. ¹H NMR (DMSO-d₆): 8.71 (d, J=2.1, 1H), 8.12 (d, J=2.1, 1H), 8.01–7.97 (m, 2H), 7.76–7.70 (m, 1H), 7.61 (t, J=7.5, 1H), 6.99 (s, 2H), 6.81 (d, J=8.7, 1H), 6.48–6.44 (m, 1H), 6.28 (d, J=8.7, 1H), 6.48–6.44 (m, 1H), 6.28 (d, J=2.4, 1H), 4.91 (s, 1H), 2.87 (s, 6H).

Example 64

2-Amino-3-cyano-7-dimethylamino-4-(phenylmethyl)-4H-chromene

The title compound was prepared from phenylacetaldehyde as a yellow solid in a yield of 3% as described in Example 30. ¹H NMR (DMSO-d₆): 7.15–7.12 (m, 3H), 6.94 (d, J=8.7, 1H), 6.86–6.83 (m, 2H), 6.56 (s, 2H), 6.50–6.47 (m, 1H), 6.03 (d, J=2.4, 1H), 3.57 (t, J=4.8, 1H), 2.94–2.88 (m, 1H), 2.85 (s, 6H), 2.80–2.74 (m, 1H).

Example 65

3-Cyano-2,7-diamino-4-(3-methoxy-4,5-methylenedioxyphenyl)-4H-chromene

The title compound was prepared from 3-aminophenol and 5-methoxypiperonal as a yellow-brown solid in a yield of 29% as described in Example 19. ¹H NMR (DMSO-d₆): 6.79 (s, 2H), 6.67 (d, J=8.1, 1H), 6.49 (d, J=1.2, 1H), 6.29–6.25 (m, 2H), 6.18 (d, J=2.4, 1H), 5.94 (d, J=5.1, 2H), 5.25 (s, 2H), 4.46 (s, 1H), 3.80 (s, 3H).

Example 66

2-Amino-3-cyano-7-dimethylamino-4-(2-pyridyl)-4H-chromene

The title compound was prepared from 2-pyridinecarboxaldehyde as a red-brown solid in a yield of 35% as described in Example 19. ¹H NMR (DMSO-d₆): 8.48–8.45 (m, 1H), 7.76–7.70 (m, 1H), 7.23–7.20 (m, 2H), 6.88 (s, 2H), 6.85 (d, J=9.0, 1H), 6.46–6.42 (m, 1H), 6.23 (d, J=3.0, 1H), 4.70 (s, 1H), 2.85 (s, 6H).

Example 67

2-Amino-3-cyano-7-dimethylamino-4-(2-phenylethyl)-4H-chromene

The title compound was prepared from hydrocinnamaldehyde as a yellow solid in a yield of 17% as described in Example 30. ¹H NMR (DMSO-d₆): 7.36–7.08 (m, 6H), 6.75 (s, 2H), 6.58–6.54 (m, 1H), 6.21 (d, J=2.4, 1H), 3.58 (t, J=6.9, 1H), 2.87 (s, 6H), 2.34–2.24 (m, 2H), 1.97–1.79 (m, 2H).

Example 68

2-Amino-3-cyano-7-dimethylamino-4-(4-methoxycarbonylphenyl)-4H-chromene

The title compound was prepared from methyl 4-formylbenzoate as a pale pink solid in a yield of 73% as described in Example 1. ¹H NMR (DMSO-d₆): 7.91 (d, J=8.1, 2H), 7.32 (d, J=8.1, 2H), 6.93 (s, 2H), 6.78 (d, J=8.7, 1H), 6.48–6.44 (m, 1H), 6.24 (d, J=2.4, 1H), 4.73 (s, 1H), 3.83 (s, 3H), 2.86 (s, 6H).

Example 69

2-Amino-3-cyano-7-dimethylamino-4-(3,4-difluoromethylenedioxyphenyl)-4H-chromene The title compound was prepared from 2,2-difluoro-5-formylbenzo-dioxole and N,N-diisopropylethylamine as a white solid in a yield of 29% as described in Example 1. ¹H NMR (DMSO-d₆): 7.34 (d, J=8.1, 1H), 7.19 (d, J=1.8, 1H), 7.04–7.01 (m, 1H), 6.91 (s, 2H), 6.79 (d, J=8.7, 1H), 6.48–6.45 (m, 1H), 6.23 (d, J=2.4, 1H), 4.70 (s, 1H), 2.86 (s, 6H).

Example 70

2-Amino-3-cyano-7-dimethylamino-4-(5-nitro-2-thienyl)-4H-chromene

The title compound was prepared from 5-nitro-2-thiophen-carboxaldehyde and N,N-diisopropylethylamine as described in Example 30. ¹H NMR (DMSO-d₆): 8.00 (d, J=5.1, 1H), 7.19 (s, 2H), 7.16 (d, J=4.2, 1H), 7.07 (d, J=8.4, 1H), 6.56–6.53 (m, 1H), 6.24 (d, J=2.4, 1H), 5.11 (s, 1H), 2.89 (s, 6H).

Example 71

2-Amino-3-cyano-7-dimethylamino-4-(5-nitro-2-furyl)-4H-chromene

The title compound was prepared from 5-nitro-2-furaldehyde and N,N-diisopropylethylamine as a brown solid as described in Example 30. ¹H NMR (DMSO-d₆): 7.63 (d, J=3.6, 1H), 7.15 (s, 2H), 7.00 (d, J=8.4, 1H), 6.65 (d, J=3.6, 1H), 6.56–6.53 (m, 1H), 6.25 (d, J=2.7, 1H), 5.00 (s, 1H), 2.89 (s, 6H).

Example 72

2-Amino-3-cyano-7-ethylamino-4-(3-methoxy-4,5-methylenedioxyphenyl)-4H-chromene

The title compound was prepared from 3-ethylaminophenol and 5-methoxypiperonal as a pale yellow solid in a yield of 34% as described in Example 30. ¹H NMR (DMSO-d₆): 6.79 (s, 2H), 6.72 (d, J=9.0, 1H), 6.50 (d, J=1.5, 1H), 6.31–6.28 (m, 2H), 6.10 (d, J=2.1, 1H), 5.95–5.93 (m, 2H), 5.77–5.74 (m, 1H), 4.48 (s, 1H), 3.80 (s, 3H), 2.99–2.95 (m, 2H), 1.12 (t, J=7.2, 3H).

Example 73

2-Amino-3-cyano-7-dimethylamino-4-(4-bromo-3,5-dimethoxyphenyl)-4H-chromene

The title compound was prepared from 4-bromo-3,5-dimethoxy-benzaldehyde as a white solid in a yield of 48% as described in Example 1. ¹H NMR (DMSO-d₆): 6.89–6.86 (m, 3H), 6.57 (s, 2H), 6.48–6.44 (m, 1H), 6.23 (d, J=2.7, 1H), 4.66 (s, 1H), 3.78 (s, 6H), 2.86 (s, 6H).

Example 74

2-Amino-3-cyano-7-dimethylamino-4-(4-pyridinyl)-4H-chromene

The title compound was prepared as a brown solid from 4-pyridine-carboxaldehyde as described in Example 1. ¹H NMR (CDCl₃): 8.54–8.52 (m, 2H), 7.13–7.11 (m, 2H), 6.75 (d, J=8.7, 1H), 6.45–6.42 (m, 1H), 6.30 (d, J=2.7, 1H), 4.64 (s, 1H), 4.63 (s, 2H), 2.94 (s, 6H).

Example 75

2-Amino-3-cyano-4-(3-methoxy-4,5-methylenedioxyphenyl)-5-methyl-pyrazo[5,4-b]-4H-pyran A solution of 5-methoxypiperonal (180.2 mg, 1 mmol), malononitrile (66 mg, 1 mmol) and N,N-diisopropylethylamine (155 mg, 1.2 mmol) in ethanol (10 ml) was stirred at room temperature for 2 h, than 3-methyl-3-pyrazolin-5-one was added. It was heated to reflux for 1 h, concentrated, and the residue was purified by column chromatography (silica gel, EtOAc/Hexane=1:1) to give 201 mg (61%) of the title compound. ¹H NMR (DMSO-d₆): 12.1 (s, 1H), 6.90 (s, 2H), 6.51 (s, 1H), 6.31 (s, 1H), 5.97 (d, 2H), 4.54 (s, 1H), 3.79 (s, 3H), 1.85 (s, 3H).

Example 76

2-Imino-3-benzoyl-7-dimethylamino-4-(3-methoxy-4,5-methylenedioxyphenyl)-chromane A solution of 5-methoxypiperonal (180.2 mg, 1 mmol), benzoylacetonitrile (66 mg, 1 mmol) and N,N- diisopropylethylamine (155 mg, 1.2 mmol) in ethanol (8 ml) was stirred at room temperature for 2 h, than 3-dimethylaminophenol was added to the solution. It was stirred at room temperature for 18 h, concentrated, and the residue was purified by column chromatography (silica gel, EtOAc/Hexane=1:1) to give 305 mg (68%) of the title compound. $^1$H NMR (CDCl$_3$): 7.80–7.77 (m, 2H), 7.50–7.42 (m, 3H), 6.88–6.30 (m, 5H), 5.95–5.94 (m, 2H), 4.73 (d), 4.45 (d, 1H), 3.88 (s, 3H), 3.35 (d, 1H), 2.86 (s, 6H).

Example 77

2-Amino-3-benzoyl-7-dimethylamino-4-(3-methoxy-4,5-methylenedioxyphenyl)-4H-chromene A solution of 2-imino-3-benzoyl-7-dimethylamino 4-(3-methoxy-4,5-methylenedioxyphenyl)-chromane (26 mg, 0.059 mmol) and triethylamine (0.1 ml) in ethanol (5 ml) was refluxed for 12 h. It was concentrated, and the residue was purified by column chromatography (silica gel, EtOAc/Hexane=1:5) to give 18 mg (72%) of the title compound. $^1$H NMR (CDCl$_3$): 7.40–7.30 (m, 2H), 7.18–7.14 (m, 2H), 6.86 (d, 1H), 6.50–6.34 (m, 2H), 6.00 (d, 1H), 5.85–5.81 (m, 2H), 5.73 (d, 1H), 4.73 (s, 1H), 3.67 (s, 3H), 2.91 (s, 6H).

Example 78

2-Imino-3-(2,2-dimethylpropanoyl)-7-dimethylamino-4-(3-methoxy-4,5-methylenedioxyphenyl)-chromane A solution of 5-methoxypiperonal (180.2 mg, 1 mmol), 4,4-dimethyl-3-oxopentanenitrile (125.2 mg, 1 mmol) and N,N-diisopropylethylamine (155.1 mg, 1.2 mmol) in ethanol (8 ml) was stirred at room temperature for 3 h, than 3-dimethylaminophenol was added to the solution. It was stirred at room temperature for 24 h, concentrated, and the residue was purified by column chromatography (silica gel, EtOAc/Hexane=1:1) to give 101 mg (24%) of the title compound. $^1$H NMR (CDCl$_3$): 6.64–6.16 (m, 5H), 5.98 (s, 2H), 4.70 (d) and 4.30 (d, 1H), 3.91 (s, 3H), 3.20 (d) and 3.02 (q, 1H), 2.91 (s, 6H), 1,30 (s, 9H).

Example 79

2-Amino-3-cyano-7-dimethylamino-4-(2-fluoro-5-trifluoromethylphenyl)-4H-chromene The title compound was prepared from 2-fluoro-5-trifluoromethyl-benzaldehyde as an orange solid in a yield of 56% as described in Example 30. $^1$H NMR (DMSO-d$_6$): 7.73–7.70 (m, 1H), 7.62–7.60 (m, 1H), 7.41 (t, J=9.45, 1H), 6.99 (s, 2H), 6.80 (d, J=8.7, 1H), 6.48–6.45 (m, 1H), 6.25 (d, J=2.7, 1H), 5.00 (s, 1H), 2.87 (s, 6H).

Example 80

2-Acetamido-3-cyano-7-dimethylamino-4-(methylenedioxy)phenyl-4H-chromene

To a solution of 2-amino-3-cyano-7-dimethylamino-4-(methylene-dioxy)phenyl-4H-chromene (43 mg, 0.13 mmol) in pyridine (1 ml) was added acetic anhydride (0.25 ml, 2.6 mmol) at room temperature. The mixture was stirred at room temperature for 3 days, then diluted with 1:1 hexane/EtOAc (40 ml), washed with water, 2N HCl, water, 2N NaOH, water and brine. The organic phase was dried over sodium sulfate and concentrated in vacuo. The residue was purified by chromatography (3:2 hexane/EtOAc) to yield the title compound as a yellow solid (4 mg, 8%). $^1$H NMR (CDCl$_3$): 6.84–6.73 (m, 4H), 6.50–6.46 (m, 1H), 6.31 (m, 1H), 5.95,5.94 (2s, 2H), 4.79 (s, 1H), 2.94 (s, 6H), 2.18 (s, 3H).

Example 81

3-Cyano-2-di(ethoxycarbonyl)amino-7-dimethylamino-4-(methylenedioxy)phenyl-4H-chromene To a solution of 2-amino-3-cyano-7-dimethylamino-4-(methylenedioxy)phenyl-4H-chromene (53 mg, 0.16 mmol) in methylenechloride (3 ml) was added pyridine (0.06 ml, 0.74 mmol), followed by ethylchloroformate (0.045 ml, 0.47 mmol). The mixture was stirred at room temperature overnight, then diluted with 1:1 hexane/EtOAc (45 ml), washed with water, 2N HCl, water and brine. The organic phase was dried over sodium sulfate and concentrated in vacuo. The residue was purified by chromatography (3:1 hexane/EtOAc) to yield the title compound as a yellow solid (5 mg, 7%). $^1$H NMR (CDCl$_3$): 6.84–6.61 (m, 4H), 6.49–6.42 (m, 1H), 6.30 (m, 1H), 5.93,5.92 (2s, 2H), 4.74 (s, 1H), 4.36 (m, 4H), 2.93 (s, 6H), 1.31 (t, J=7.2, 6H).

Example 82

2,7-Diamino-3-cyano-4-(3-bromo-4,5-dimethoxyphenyl)-4H-chromene

The title compound was prepared from 5-bromoveratraldehyde as a white solid in a yield of 37% by a procedure similar to that described for Example 19. $^1$H NMR (DMSO-d$_6$): 6.92 (d, J=1.8, 1H), 6.85 (s, 2H), 6.83 (d, J=1.8, 1H), 6.70 (d, J=8.1, 1H), 6.31–6.27 (m, 1H), 6.20 (d, J=2.1, 1H), 5.28 (s, 2H), 4.54 (s, 1H), 3.80 (s, 3H), 3.70 (d, J=0.6, 3H).

Example 83

2-Amino-7-chloroacetamido-3-cyano-4-(3-bromo-4,5-dimethoxyphenyl)-4H-chromene

To a solution of 2,7-diamino-3-cyano-4-(3-bromo-4,5-dimethoxy phenyl)-4H-chromene (50 mg, 0.124 mmol) in dichloromethane (2 ml) was added N,N-diisopropylethylamine (0.043ml, 0.247 mmol). The flask was cooled in iced water and a solution of chloroacetyl chloride (14 mg, 0.124 mmol) in dichloromethane (1 ml) was added dropwise. The reaction mixture was stirred for 3 h, diluted with ethyl acetate, then washed with water, brine and dried over anhydrous sodium sulfate, and evaporated. The resulting solid was washed with a small amount of dichloromethane to yield the title compound as a white solid in a yield of 24%. $^1$H NMR (DMSO d$_6$): 10.45 (s, 1H), 7.56 (s, 1H), 7.14–7.12 (m, 1H), 7.07 (s, 1H), 7.05 (s, 2H), 6.97 (s, 1H), 6.89 (d, J=0.9, 1H), 4.74 (s, 1H), 4.24 (s, 2H), 3.80 (s, 3H), 3.70 (s, 3H).

Example 84

2-Amino-3-cyano-7-phenylamino-4-(3-methoxy-4,5-methylenedioxyphenyl)-4H-chromene The title compound was prepared from 5-methoxypiperonal and 3-hydroxydiphenylamine as a yellow solid by a procedure similar to that described for Example 30. $^1$H NMR (DMSO-d$_6$): 8.31 (s, 1H), 7.26 (t, J=10.5, 2H), 7.07 (d, J=7.8, 2H), 6.91–6.88 (m, 4H), 6.77–6.73 (m, 1H), 6.65 (d, J=2.7, 1H), 6.55 (d, J=1.5, 1H), 6.34 (d, J=1.5, 1H), 5.95 (d, J=4.5, 2H), 4.57 (s, 1H), 3.82 (s, 3H).

Example 85

2-Amino-3-cyano-7-ethylamino-6-methyl-4-(3-methoxy-4,5-methylenedioxyphenyl)-4H-chromene

The title compound was prepared from 5-methoxypiperonal and 3-ethylamino-p-cresol as a light yellow solid in a yield of 21% by a procedure similar to that described for Example 30. $^1$H NMR (DMSO-d$_6$): 6.75 (s, 2H), 6.59 (s, 1H), 6.49 (d, J=1.2, 1H), 6.27 (d, J=1.2, 1H), 6.05 (s, 1H), 5.94 (d, J=5.1, 2H), 4.94 (t, J=5.1, 1H), 4.46 (s, 1H), 3.81 (s, 3H), 3.07–3.01 (m, 2H), 1.95 (s, 3H), 1.170 (t, J=6.9, 3H).

Example 86

3-Cyano-2,7-diamino-8-methyl-4-(3-methoxy-4,5-methylenedioxyphenyl)-4H-chromene

The title compound was prepared from 5-methoxypiperonal and 3-amino-o-cresol as a yellow solid in a yield of 18% by a procedure similar to that described for Example 30. $^1$H NMR (DMSO-d$_6$): 6.80 (s, 2H), 6.57 (d, J=8.1, 1H), 6.48 (d, J=1.5, 1H), 6.34 (d, J=8.4, 1H), 6.26 (d, J=1.5, 1H), 5.93 (d, J=4.8, 2H), 4.98 (s, 2H), 4.46 (s, 1H), 3.80 (s, 3H), 2.00 (s, 3H).

Example 87

2-Amino-3-cyano-7-dimethylamino-4-(3-bromophenyl)-4H-chromene

The title compound was prepared from 3-bromobenzaldehyde as a yellow solid in a yield of 62% by a procedure similar to that described for Example 30. $^1$H NMR (DMSO-d$_6$): 7.43–7.39 (m, 1H), 7.33 (t, J=1.8, 1H), 7.29 (t, J=10.2, 1H), 7.20–7.17 (m, 1H), 6.92 (s, 2H), 6.81 (d, J=8.4, 1H), 6.49–6.45 (m, 1H), 6.24 (d, J=2.7, 1H), 4.66 (s, 1H), 2.87 (s, 6H).

Example 88

2-Amino-3-cyano-7-dimethylamino-4-ethyl-4H-chromene

The title compound was prepared from propionaldehyde as a sticky yellow solid in a yield of 5% by a procedure similar to that described for Example 30. $^1$H NMR (DMSO-d$_6$): 7.02 (d, J=8.7, 1H), 6.67 (s, 2H), 6.55–6.51 (m, 1H), 6.18 (d, J=2.4, 1H), 3.45 (t, J=4.5, 1H), 2.87 (s. 6H), 1.63–1.57 (m, 2H), 0.66 (t, J=7.5, 3H).

Example 89

2-Amino-3-cyano-7-dimethylamino-4-(3,5-dibromophenyl)-4H-chromene

The title compound was prepared from 3,5-dibromobenzaldehyde as a yellow solid in a yield of 9% by a procedure similar to that described for Example 19. $^1$H NMR (DMSO-d$_6$): 7.70 (s, 1H), 7.36 (d, J=1.2, 2H), 7.00 (s, 2H), 6.83 (d, J=8.7, 1H), 6.51–6.47 (m, 1H), 6.23 (d, J=2.7, 1H), 4.71 (s, 1H), 2.88 (s, 6H).

Example 90

2-Amino-3-cyano-7-dimethylamino-4-(3-cyanophenyl)-4H-chromene

The title compound was prepared from 3-cyanobenzaldehyde as a yellow solid in a yield of 25% by a procedure similar to that described for Example 30. $^1$H NMR (DMSO-d$_6$): 7.70 (d, J=7.5, 1H), 7.65 (s, 1), 7.56–7.50 (m, 2H), 6.96 (s, 2H), 6.79 (d, J=8.4, 1H), 6.49–6.45 (m, 1H), 6.24 (d, J=2.4, 1H), 4.75 (s, 1H), 2.87 (s, 6H).

Example 91

2-Amino-3-cyano-7-dimethylamino-4-(3-methoxyphenyl)-4H-chromene

The title compound was prepared from m-anisaldehyde as a yellow solid in a yield of 19% by a procedure similar to that described for Example 30. $^1$H NMR (CDCl$_3$): 7.19 (t, J=0.6, 1H), 6.82–6.72 (m, 4H), 6.44–6.40 (m, 1H), 6.28 (d, J=2.7, 1H), 4.61 (s, 1H), 4.54 (s, 2H), 3.77 (s, 3H), 2.92 (s, 6H).

Example 92

2-Amino-3-cyano-7-dimethylamino-4-(3-chlorophenyl)-4H-chromene

The title compound was prepared from 3-chlorobenzaldehyde as a yellow solid in a yield of 33% by a procedure similar to that described for Example 30. $^1$H NMR (DMSO-d$_6$): 7.35 (t, J=7.5, 1H), 7.29–7.25 (m, 1H), 7.19 (t, J=1.8, 1H), 7.16–7.13 (m, 1H), 6.91 (s, 2H), 6.81 (d, J=8.4, 1H), 6.49–6.45 (m, 1H), 6.23 (d, J=2.7, 1H), 4.66 (s, 1H), 2.87 (s, 6H).

Example 93

2-Amino-3-cyano-7-dimethylamino-4-(3-methylphenyl)-4H-chromene

The title compound was prepared from m-tolualdehyde as a white solid in a yield of 24% by a procedure similar to that described for Example 1. $^1$H NMR (DMSO-d$_6$): 7.18 (t, J=7.5, 1H), 7.00 (d, J=7.2, 1H), 6.95 (d, J=2.1, 2H), 6.80 (s, 2H), 6.78 (d, J=8.7, 1H), 6.46–6.43 (m, 1H), 6.22 (d, J=2.4, 1H), 4.54 (s, 1H), 2.86 (s, 6H), 2.26 (s, 3H).

Example 94

2-Amino-3-cyano-4-(3-methoxy-4,5-methylenedioxyphenyl)-4H-indolo[4,5-b]pyran

The title compound was prepared from 5-methoxypiperonal and 4-hydroxyindole as a light yellow solid by a procedure similar to that described for Example 30. $^1$H NMR (CDCl$_3$): 8.34 (s, 1H), 7.21 (t, J=2.7, 1H), 7.10 (d, J=8.7, 1H), 6.76 (d, J=8.4, 1H), 6.64 (d, J=2.4, 1H), 6.46 (d, J=1.2, 1H), 6.34 (d, J=1.5, 1H), 5.91 (d, J=5.7, 2H), 4.74 (s, 1H), 4.68 (s, 2H), 3.88 (s, 3H).

Example 95

2-Amino-3-cyano-4-(2-bromo-4,5-dimethoxyphenyl)-4H-indolo[4,5-b]pyran

The title compound was prepared from 6-bromoveratraldehyde and 4-hydroxyindole as a yellow solid in a yield of 38% by a procedure similar to that described for Example 30. $^1$H NMR (DMSO-d$_6$): 11.31 (s, 1H), 7.35 (t, J=2.7, 1H), 7.11 (s, 1H), 7.09 (d, J=9.6, 1H), 6.94 (s, 2H), 6.67 (s, 1H), 6.62 (d, J=8.4, 1H), 6.46 (s, 1H), 5.23 (s, 1H), 3.77 (s, 3H), 3.59 (s, 3H).

Example 96

2-Amino-3-cyano-4-(2-bromo-4,5-dimethoxyphenyl)-8-methyl-4H-indolo[4,5-b]pyran

The title compound was prepared from 6-bromoveratraldehyde and 4-hydroxy-2-methylindole as a yellow solid in a yield of 53% by a procedure similar to that described for Example 1. $^1$H NMR (DMSO-d$_6$): 11.13 (s, 1H), 7.10 (s, 1H), 6.96 (d, J=8.4, 1H), 6.90 (s, 2H), 6.64 (s, 1H), 6.52 (d, J=8.4, 1H), 6.15 (s, 1H), 5.20 (s, 1H), 3.77 (s, 3H), 3.58 (s, 3H), 2.37 (s, 3H).

Example 97

2-Amino-3-cyano-4-(3-bromo-4,5-dimethoxyphenyl)-4H-indolo[4,5-b]pyran

The title compound was prepared from 5-bromoveratraldehyde and 4-hydroxyindole as a pale yellow solid in a yield of 10% by a procedure similar to that described for Example 19. $^1$H NMR (DMSO-d$_6$): 11.33 (s, 1H), 7.36 (t, J=2.4, 1H), 7.12 (d, J=8.4, 1H), 7.00 (s, 2H), 6.98 (s, 1H), 6.87 (d, J=1.8, 1H), 6.74 (d, J=8.7, 1H), 6.46 (s, 1H), 4.80 (s, 1H), 3.80 (s, 3H), 3.69 (s, 3H).

Example 98

2-Amino-3-cyano-4-(3-bromo-4,5-dimethoxyphenyl)-8-methyl-4H-indolo[4,5-b]pyron The title compound was prepared from 5-bromoveratraldehyde and 4-hydroxy-2-methylindole as a white solid in a yield of 48% by a procedure similar to that described for Example 1. $^1$H NMR (DMSO-d$_6$): 11.15 (s, 1H), 6.99 (d, J=8.7, 1H), 6.97 (s, 1H), 6.94 (s, 2H), 6.85 (d, J=1.8, 1H), 6.64 (d, J=8.4, 1H), 6.16 (s, 1H), 4.77 (s, 1H), 3.79 (s, 3H), 3.69 (s, 3H), 2.38 (s, 3H).

Example 99

2-Amino-3-cyano-4-(3,4,5-trimethoxyphenyl)-4H-indolo[4,5-b]pyran

The title compound was prepared from 3,4,5-trimethoxybenzaldehyde and 4-hydroxyindole as a white solid in a yield of 43% by a procedure similar to that described for Example 1. $^1$H NMR (DMSO-d$_6$): 11.29 (s, 1H), 7.35 (t, J=2.7, 1H), 7.10 (d, J=9.0, 1H), 6.90 (s, 2H), 6.76 (d, J=8.4, 1H), 6.52 (s, 2H), 6.46–6.45 (m, 1H), 6.75 (s, 1H), 3.70 (s, 6H), 3.62 (s, 3H).

Example 100

2-Amino-3-cyano-4-(3-nitrophenyl)-4H-indolo[4,5-b]pyran

The title compound was prepared from 3-nitrobenzaldehyde and 4-hydroxyindole as a yellow solid in a yield of 17% by a procedure similar to that described for Example 30. $^1$H NMR (DMSO-d$_6$): 8.30 (s, 1H), 8.12–8.08 (m, 1H), 8.05 (t, J=2.1, 1H), 7.64–7.61 (m, 1H), 7.49 (t, J=7.8, 1H), 7.24 (d, J=2.7, 1H), 7.13–7.10 (m, 1H), 6.69–6.66 (m, 2H), 4.99 (s, 1H), 4.78 (s, 2H).

Example 101

2-Amino-3-cyano-4-(3,5-dimethoxyphenyl)-4H-indolo[4,5-b]pyran

The title compound was prepared from 3,5-dimethoxybenzaldehyde and 4-hydroxyindole as a yellow solid in a yield of 12% by a procedure similar to that described for Example 30. $^1$H NMR (DMSO-d$_6$): 11.30 (s, 1H), 7.35 (t, J=2.7, 1H), 7.09 (d, J=8.7, 1H), 6.91 (s, 2H), 6.73 (d, J=8.4, 1H), 6.45 (s, 1H), 6.34 (s, 3H), 4.70 (s, 1H), 3.68 (s, 6H).

Example 102

2-Amino-3-cyano-4-(3-cyanophenyl)-4H-indolo[4,5-b]pyran

The title compound was prepared from 3-cyanobenzaldehyde and 4-hydroxyindole as a pale yellow solid in a yield of 33% by a procedure similar to that described for Example 30. $^1$H NMR (DMSO-d$_6$): 11.34 (s, 1H), 7.71–7.68 (m, 2H), 7.54–7.52 (m, 2H), 7.37 (t, J=3.9, 1H), 7.11 (d, J=8.4, 1H), 7.04 (s, 2H), 6.67 (d, J=8.7, 1H), 6.47 (s, 1H), 4.93 (s, 1H).

Example 103

2-Amino-3-cyano-4-(3-bromo-4,5-dimethoxyphenyl)-4H-naphtho[1,2-b]pyran

The title compound was prepared from 5-bromoveratraldehyde and 1-naphthol as a white solid in a yield of 20% by a procedure similar to that described for Example 1. $^1$H NMR (DMSO-d$_6$): 8.23 (d, J=8.1, 1H), 7.91 (d, J=8.1, 1H), 7.67–7.59 (m, 3H), 7.23 (s, 2H), 7.20 (d, J=8.4, 1H), 7.06 (s, 1H), 6.95 (d, J=1.8, 1H), 4.93 (s, 1H), 3.80 (s, 3H), 3.70 (s, 3H).

Example 104

2-Amino-3-cyano-4-(3,4,5-trimethoxyphenyl)-4H-naphtho[1,2-b]pyran

The title compound was prepared from 3,4,5-trimethoxybenzaldehyde and 1-naphthol as a white solid in a yield of 8% by a procedure similar to that described for Example 19. $^1$H NMR (DMSO-d$_6$): 8.23 (d, J=8.1, 1H), 7.90 (d, J=8.4, 1H), 7.66–7.55 (m, 3H), 7.20 (d, J=8.7, 1H), 7.15 (s, 2H), 6.58 (s, 2H), 4.87 (s, 1H), 3.71 (s, 6H), 3.63 (s, 3H).

Example 105

2-Amino-3-cyano-4-(4-bromo-3,5-dimethoxyphenyl)-4H-naphtho[1,2-b]pyran

The title compound was prepared from 4-bromo-3,5-dimethoxy-benzaldehyde and 1-naphthol as a white solid in a yield of 32% by a procedure similar to that described for Example 1. $^1$H NMR (DMSO-d$_6$): 8.24 (d, J=7.8, 1H), 7.91 (d, J=7.5, 1H), 7.67–7.56 (m, 3H), 7.21 (s, 2H), 7.19 (d, J=8.4, 1H), 6.67 (s, 2H), 4.97 (s, 1H), 3.78 (s, 6H).

Example 106

2-Amino-3-cyano-4-(3-methoxy-4,5-methylenedioxyphenyl)-4H-naphtho[1,2-b]pyran The title compound was prepared from 5-methoxypiperonal and 1-naphthol as a white solid by a procedure similar to that described for Example 30. $^1$H NMR (DMSO-d$_6$): 8.22 (d, J=7.8, 1H), 7.90 (d, J=8.1, 1H), 7.66–7.55 (m, 3H), 7.16 (d, J=8.7, 1H), 7.15 (s, 2H), 6.62 (s, 1H), 6.40 (s, 1H), 5.94 (d, J=8.7, 2H), 4.84 (s, 1H), 3.81 (s, 3H).

Example 107

2-Amino-3-cyano-7-dimethylamino-4-(3,5-difluorophenyl)-4H-chromene

The title compound was prepared from 3,5-difluorobenzaldehyde as a light yellow solid in a yield of 21% by a procedure similar to that described for Example 19. $^1$H NMR (DMSO-d$_6$): 7.12–7.04 (m, 1H), 6.96 (s, 2H), 6.90–6.83 (m, 3H), 6.50–6.46 (m, 1H), 6.23 (d, J=2.7, 1H), 4.72 (s, 1H), 2.87 (s, 6H).

Example 108

2-Amino-3-cyano-7-dimethylamino-4-(3,5-bis(trifluoromethyl)phenyl)-4H-chromene

The title compound was prepared from 3,5-bis(trifluoromethyl)-benzaldehyde as a white solid in a yield of 13% by a procedure similar to that described for Example 19. $^1$HNMR (DMSO-d$_6$): 8.01 (s, 1H), 7.86 (s, 2H), 7.06 (s, 2H), 6.83 (d, J=8.4, 1H), 6.51–6.48 (m, 1H), 6.26 (d, J=2.1, 1H), 5.01 (s, 1H), 2.88 (s, 6H).

Example 109

2-Amino-3-cyano-7-dimethylamino-4-(3-bromo-5-methoxyphenyl)-4H-chromene

The title compound was prepared from 3-bromo-5-methoxy-benzaldehyde as a white solid in a yield of 50% by a procedure similar to that described for Example 1. $^1$H NMR (DMSO-d$_6$): 6.99 (s, 1H), 6.91 (s, 2H), 6.85 (s, 1H), 6.84 (d, J=8.7, 1H), 6.77 (s, 1H), 6.49–6.46 (m, 1H), 4.61 (s, 1H), 3.75 (s, 3H), 2.87 (s, 6H).

Example 110

2-Amino-3-cyano-4-(3-methoxy-4,5-methylenedioxyphenyl)-6,7,8,9,10,11-hexahydro-4H-pyrido[3,2,1-ij]quino[5,6-b]pyran The title compound was prepared from 8-hydroxyjulolidine and 5-methoxypiperonal as a yellow solid by a procedure similar to that described for Example 19. $^1$H NMR (CDCl$_3$): 6.43 (d, J=1.5, 1H), 6.37 (s, 1H), 6.32 (d, J=1.5, 1H), 5.93–5.91 (m, 2H), 4.50 (s, 2H), 4.47 (s, 1H), 3.91 (s, 3H), 3.11–3.06 (m, 4H), 2.72 (t, J=6.6, 2H), 2.60 (t, J=6.6, 2H), 2.01–1.86 (m, 4H).

Example 111

2-Amino-3-cyano-7-dimethylamino-4-(4-chloromethylphenyl)-4H-chromene

The title compound was prepared from 4-chloromethylbenzaldehyde as a yellow solid by a procedure similar to that described for Example 30. $^1$H NMR (DMSO-d$_6$): 7.36 (d, J=8.1, 1H), 7.16 (d, J=7.8, 1H), 6.84 (s, 2H), 6.77 (d, J=8.7, 1H), 6.47–6.43 (m, 1H), 6.22 (d, J=2.7, 1H), 4.72 (s, 2H), 4.62 (s, 1H), 2.86 (s, 6H).

Example 112

2-Amino-3-cyano-7-dimethylamino-4-(3-chloromethylphenyl)-4H-chromene

The title compound was prepared from 3-chloromethylbenzaldehyde as a yellow solid by a procedure similar to that described for Example 30. $^1$H NMR (DMSO-d$_6$): 7.31 (d, J=7.8, 1H), 7.28 (s, 1H), 7.22 (s, 1H), 7.15 (d, J=6.9, 1H), 6.85 (s, 2H), 6.78 (d, J=8.7, 1H), 6.47–6.44 (m, 1H), 6.23 (d, J=2.4, 1H), 4.73 (s, 1H), 4.63 (s, 1H), 2.86 (s, 6H).

Example 113

2-Amino-3-cyano-7-dimethylamino-4-(3-cyano-4-fluorophenyl)-4H-chromene

The title compound was prepared from 2-fluoro-5-formylbenzonitrile as a yellow solid by a procedure similar to that described for Example 30. $^1$H NMR (DMSO-d$_6$): 7.78–7.75 (m, 1H), 7.58–7.52 (m, 1H), 7.48 (t, J=9.0, 1H), 6.93 (s, 2H), 6.79 (d, J=9.0, 1H), 6.49–6.45 (m, 1H), 6.23 (d, J=2.7, 1H), 4.77 (s, 1H), 2.87 (s, 6H).

Example 114

2-Amino-3-cyano-7-dimethylamino-4-(3-nitro-4-fluorophenyl)-4H-chromene

The title compound was prepared from 3-nitro-4-fluorobenzaldehyde as a yellow solid by a procedure similar to that described for Example 30. $^1$H NMR (DMSO-d$_6$): 7.97–7.95 (m, 1H), 7.60 (m, 1H), 7.56 (d, J=11.4, 1H), 7.00 (s, 2H), 6.82 (d, J=8.7, 1H), 6.50–6.46 (m, 1H), 6.24 (d, J=2.4, 1H), 4.86 (s, 1H), 2.87 (s, 6H).

Example 115

2-Amino-3-cyano-7-dimethylamino-4-(3-bromo-4,5-methylenedioxyphenyl)-4H-chromene The title compound was prepared from 5-bromopiperonal as a light brown solid by a procedure similar to that described for Example 1. $^1$H NMR (DMSO-d$_6$): 6.87 (s, 2H), 6.84–6.80 (m, 2H), 6.67 (d, J=1.2, 1H), 6.50–6.46 (m, 1H), 6.22 (d, J=2.4, 1H), 6.08 (d, J=6.9, 2H), 4.58 (s, 1H), 2.87 (s, 6H).

Example 116

2-Amino-3-cyano-7-methoxy-4-(3-bromo-4,5-dimethoxyphenyl)-4H-chromene

The title compound was prepared from 3-methoxyphenol and 5-bromoveratraldehyde as a yellow solid by a procedure similar to that described for Example 30. $^1$H NMR (DMSO-d$_6$): 7.02 (d, J=8.7, 1H), 7.00 (s, 2H), 6.98 (d, J=1.8, 1H), 6.87 (d, J=1.8, 1H), 6.71–6.68 (m, 1H), 6.56 (d, J=2.4, 1H), 4.71 (s, 1H), 3.80 (s, 3H), 3.74 (s, 3H), 3.70 (d, J=0.6, 3H).

Example 117

2-Amino-3-cyano-7-dimethylamino-4-(3-trifluoromethylthiophenyl)-4H-chromene

The title compound was prepared from 3-trifluoromethylthio-benzaldehyde as a yellow solid by a procedure similar to that described for Example 30. $^1$H NMR (DMSO-d$_6$): 7.58–7.46 (m, 1H), 7.39 (d, J=8.4, 1H), 6.92 (s, 2H), 6.80 (d, J=9.0, 1H), 6.49–6.45 (m, 1H), 6.24 (d, J=2.4, 1H), 4.75 (s, 1H), 2.87 (s, 6H).

Example 118

2-Amino-3-cyano-7-dimethylamino-4-(3-fluorophenyl)-4H-chromene

The title compound was prepared from 3-fluorobenzaldehyde as a white solid by a procedure similar to that described for Example 30. $^1$H NMR (DMSO-d$_6$): 7.39–7.31 (m, 1H), 7.06–6.95 (m, 3H), 6.89 (s, 2H), 6.82 (d, J=8.4, 1H), 6.48–6.45 (m, 1H), 6.23 (d, J=2.1, 1H), 4.66 (s, 1H), 2.86 (s, 6H).

Example 119

2-Amino-3-cyano-7-dimethylamino-4-(3-difluoromethoxyphenyl)-4H-chromene

The title compound was prepared from 3-(difluoromethoxy)-benzaldehyde as a white solid by a procedure similar to that described for Example 30. ¹H NMR (DMSO-d₆): 7.36 (t, J=7.8, 1H), 7.05–6.91 (m, 3H), 6.88 (s, 2H), 6.82 (d, J=9.0, 1H), 6.84–6.45 (m, 1H), 6.23 (d, J=2.4, 1H), 4.66 (s, 1H), 2.86 (s, 6H).

Example 120

2-Amino-3-cyano-7-dimethylamino-4-(3-hydroxyphenyl)-4H-chromene

The title compound was prepared from 3-acetoxybenzaldehyde as a white solid by a procedure similar to that described for Example 30. ¹HNMR (DMSO-d₆): 9.31 (s, 1H), 7.07 (t, J=7.8, 1H), 6.79 (t, J=4.5, 1H), 6.64–6.55 (m, 2H), 6.52 (s, 1H), 6.48–6.44 (m, 1H), 6.22 (d, J=2.4, 1H), 4.48 (s, 1H), 2.86 (s, 6H).

Example 121

2-Amino-3-cyano-7-dimethylamino-4-(3-trifluoromethoxyphenyl)-4H-chromene

The title compound was prepared from 3-(trifluoromethoxy)benzaldehyde as a yellow solid by a procedure similar to that described for Example 30. ¹H NMR (DMSO-d₆): 7.45 (t, J=7.5, 1H), 7;21–7.15 (m, 3H), 6.92 (s, 2H), 6.82 (d, J=8.7, 1H), 6.49–6.46 (m, 1H), 6.24 (d, J=2.7, 1H), 4.73 (s, 1H), 2.87 (s, 6H).

Example 122

2-Amino-3-cyano-7-dimethylamino-4-(3-methylaminophenyl)-4H-chromene

The title compound was prepared from 3-methylaminobenzaldehyde as a yellow solid by a procedure similar to that described for Example 30. ¹H NMR (DMSO-d₆): 6.99 (t, J=8.1, 1H), 6.80 (d, J=8.4, 1H), 6.74 (s, 2H), 6.47–6.43 (m, 1H), 6.35 (s, 1H), 6.33 (d, J=7.2, 2H), 6.21 (d, J=2.4, 1H), 5.64–5.59 (m, 1H), 4.41 (s, 1H), 2.85 (s, 6H), 2.62 (d, J=5.1, 3H).

Example 123

2-Amino-3-cyano-7-dimethylamino-4-(3-dimethylaminophenyl)-4H-chromene

The title compound was prepared from 3-dimethylaminobenzaldehyde as a yellow solid by a procedure similar to that described for Example 30. ¹H NMR (DMSO-d₆): 7.07 (t, J=7.8, 1H), 6.83 (d, J=8.7, 1H), 6.76 (s, 2H), 6.59 (s, 1H), 6.55–6.52 (m, 1H), 6.46–6.43 (m, 1H), 6.38 (d, J=7.5, 1H), 6.22 (d, J=2.4, 1H), 4.49 (s, 1H), 2.86 (d, J=3.9, 12H).

Example 124

2-Amino-3-cyano-7-dimethylamino-4-(3-iodo-4,5-dimethoxyphenyl)-4H-naphtho[1,2-b]pyran The title compound was prepared from 3-iodo-4,5-dimethoxy-benzaldehyde as a white solid by a procedure similar to that described for Example 1. ¹H NMR (DMSO-d₆): 8.24 (d, J=7.5, 1H), 7.91 (d, J=7.5, 1H), 7.67–7.56 (m, 3H), 7.22 (s, 2H), 7.19 (d, J=8.7, 1H), 7.13 (d, J=1.2, 1H), 7.05 (d, J=1.5, 1H), 4.90 (s, 1H), 3.78 (s, 3H), 3.67 (s, 3H).

Example 125

2-Amino-3-cyano-7-dimethylamino-4-(3-iodo-4,5-dimethoxyphenyl)-4H-chromene

The title compound was prepared from 3-iodo-4,5-dimethoxybenzaldehyde as a white solid by a procedure similar to that described for Example 1. ¹H NMR (DMSO-d₆): 7.02 (d, J=1.8, 1H), 6.96 (s, 1H), 6.88 (s, 2H), 6.86 (d, J=8.7, 1H), 6.49–6.46 (m, 1H), 6.22 (d, J=2.4, 1H), 4.59 (s, 1H), 3.78 (s, 3H), 3.66 (s, 3H), 2.87 (s, 6H).

Example 126

2-Amino-3-cyano-7-dimethylamino-4-(4-acetoxy-3,5-dimethoxyphenyl)-4H-chromene

The title compound was prepared from 4-acetoxy-3,5-dimethoxy-benzaldehyde as a yellow solid by a procedure similar to that described for Example 30. ¹H NMR (DMSO-d₆): 6.92 (d, J=9.0, 1H), 6.86 (s, 2H), 6.56 (s, 2H), 6.50–6.46 (m, 1H), 6.23 (d, J=2.4, 1H), 4.63 (s, 1H), 3.70 (s, 6H), 2.87 (s, 6H), 2.22 (s, 3H).

Example 127

2-Amino-3-cyano-7-dimethylamino-4-(4-acetoxy-3,5-dimethoxyphenyl)-4H-naphtho[1,2-b]pyran The title compound was prepared from 4-acetoxy-3,5-dimethoxy-benzaldehyde as a white solid by a procedure similar to that described for Example 1. ¹H NMR (DMSO-d₆): 8.24 (d, J=8.1, 1H), 7.90 (d, J=7.8, 1H), 7.66–7.55 (m, 3H), 7.24 (d, J=8.7, 1H), 7.20 (s, 2H), 6.66 (s, 2H), 4.94 (s, 1H), 3.70 (s, 6H), 2.22 (s, 3H).

Example 128

2-Amino-3-cyano-7-dimethylamino-4-(5-methyl-3-pyridyl)-4H-chromene

Step 1. 5-Methyl-3-pyridinemethanol. To a solution of methyl 5-methyl-3-pyridinecarboxylate (0.95 g, 6.3 mmol) in THF (10 mL) was added LiAlH₄ (300 mg, 7.9 mmol) at 0° C. The mixture was stirred at room temperature for 2 h, quenched with water, and extracted with 1:1 hexane/EtOAc (80 mL). The organic phase was washed with water and brine, dried over Na₂SO₄ and concentrated in vacuo to yield the title compound as an oil (400 mg, 3.2 mmol, 51%). ¹H NMR (CDCl₃): 8.40 (s, 1H), 8.37 (s, 1H), 7.31 (s, 1H), 4.71 (s, 2H), 2.35 (s, 3H).

Step 2. 5-methyl-3-pyridinecarboxaldehyde. A mixture of 5-methyl-3-pyridinemethanol (106 mg, 0.86 mmol) and activated MnO₂ (376 mg) in methylenechloride (10 mL) was stifled at room temperature overnight. The black solid of MnO₂ was removed by filtration. The filtrate was concentrated in vacuo to yield the title compound as an oil (100 mg, 85%). ¹H NMR (CDCl₃): 10.10 (s, 1H), 8.89 (s, 1H), 8.68 (s, 1H), 7.98 (s, 1H), 2.45 (s, 3H).

Step 3. 2-Amino-3-cyano-7-dimethylamino-4-(5-methyl-3-pyridyl)-4H-chromene. The title compound was prepared as a yellow solid from 5-methyl-3-pyridinecarboxaldehyde in 4% yield by a procedure similar to that described for example 1. ¹H NMR (DMSO-d₆): 8.22 (d, J=6.7, 1H), 7.29 (s, 1H), 6.88 (s, 2H), 6.75 (d, J=8.1, 1H), 6.44 (d, J=6.7, 1H), 6.26 (s, 1H), 4.64 (s, 1H), 2.84 (s, 6H), 2.23 (s, 3H).

Example 129

2-Amino-3-cyano-7-dimethylamino-4-(3-chloro-4,5-dimethoxyphenyl)-4H-chromene

The title compound was prepared from 3-chloro-4,5-dimethoxy-benzaldehyde as a yellow solid by a procedure similar to that described for Example 1. ¹H NMR (CDCl₃): 6.82–6.69 (m, 3H), 6.48–6.44 (m, 1H), 6.30 (d, J=2.7, 1H), 4.59 (s, 3H), 3.86 (s, 3H), 3.85 (s, 3H), 2.85 (s, 6H).

Example 130

2-Chloroacetamido-3-cyano-7-dimethylamino-4-(3-bromo-4,5-dimethoxyphenyl)-4H-chromene The title compound was prepared from 2-amino-3-cyano-7-dimethyl-amino-4-(3-bromo-4,5-dimethoxyphenyl)-4H-chromene and chloroacetyl chloride as a yellow solid by a procedure similar to that described for Example 80. $^1$H NMR (CDCl$_3$): 8.26 (s, 1H), 6.97–6.80 (m, 3H), 6.50–6.46 (m, 1H), 6.33 (d, J=2.4, 1H), 4.73 (s, 3H), 4.23 (s, 2H), 3.85 (s, 3H), 3.83 (s, 3H), 2.95 (s, 6H).

Example 131

2-Acrylamido-3-cyano-7-dimethylamino-4-(3-bromo-4,5-dimethoxyphenyl)-4H-chromene The title compound was prepared from 2-amino-3-cyano-7-dimethyl-amino-4-(3-bromo-4,5-dimethoxyphenyl)-4H-chromene and acryloyl chloride as a yellow solid by a procedure similar to that described for Example 80. $^1$H NMR (CDCl$_3$): 6.96–6.23 (m, 7H), 5.92 (d, J=10.2, 1H), 4.73 (s, 1H), 3.87 (s, 3H), 3.85 (s, 3H), 2.96 (s, 6H).

Example 132

3-Cyano-7-dimethylamino-2-succinimido-4-(3-bromo-4,5-dimethoxyphenyl)-4H-chromene The title compound was prepared from 2-amino-3-cyano-7-dimethylamino-4-(3-bromo-4,5-dimethoxyphenyl)-4H-chromene and succinyl chloride as a yellow solid by a procedure similar to that described for Example 80. $^1$H NMR (CDCl$_3$): 7.12 (d, J=1.8, 1H), 6.89–6.85 (m, 2H), 6.47 (m, 1H), 6.26 (d, J=2.7, 1H), 4.79 (s, 1H), 3.87 (s, 3H), 3.83 (s, 3H), 2.96 (s, 4H), 2.92 (s, 6H).

Example 133

3-Cyano-7-dimethylamino-2-phenylureido-4-(3-bromo-4,5-dimethoxyphenyl)-4H-chromene A mixture of 2-amino-3-cyano-7-dimethylamino-4-(3-bromo-4,5-dimethoxyphenyl)-4H-chromene (92 mg, 0.21 mmol) and phenyl isocyanate (0.1 mL) in pyridine (4 mL) was stirred at room temperature for 6 h. The mixture was diluted with 1:1 hexane/EtOAc (100 mL) then washed with water, 2N HCl, water and brine. The solution was dried over Na$_2$SO$_4$ and concentrated in vacuo. The residue was purified by chromatography to yield the title compound as a yellow solid (26 mg, 0.05 mmol, 23%). $^1$H NMR (CDCl$_3$): 7.66 (s, 1H), 7.42–7.33 (m, 5H), 7.15 (m, 1H), 6.95 (s, 1H), 6.82–6.73 (m, 2H), 6.52–6.47 (m, 1H), 6.39 (s, 1H), 4.68 (s, 1H), 3.85 (s, 3H), 3.84 (s, 1H), 2.96 (s, 6H).

Example 134

9-Acetamide-2-amino-3-cyano-4-(3-bromo-4,5-dimethoxyphenyl)-4H-indolo[4,5-b]pyran The title compound was prepared as a yellow solid by a procedure similar to that described in Example 1 in 6% yield. $^1$H NMR (DMSO-d$_6$): 11.07 (s, 1H), 7.25 (s, 1H), 7.15 (d, J=2.4, 1H), 7.06 (d, J=8.1, 1H), 7.01 (d, J=2.4, 1H), 6.91 (s, 1H), 6.85 (s, 2H), 6.70 (d, J=8.1, 1H), 4.78 (s, 1H), 3.81 (s, 3H), 3.69 (s, 3H), 3.66–3.65 (m, 1H).

Example 135

2-Amino-3-cyano-7-dimethylamino-4-(5-bromo-3-pyridyl)-4H-chromene

The title compound was prepared as a light brown solid by a procedure similar to that described in Example 128. $^1$H NMR (DMSO-d$_6$): 8.54 (s, 1H), 8.41 (s, 1H), 7.71 (s, 1H), 6.98 (s, 2H), 6.82–6.77 (m, 2H), 6.48–6.46 (m, 1H), 6.27 (s, 1H), 4.75 (s, 1H), 2.84 (s, 6H).

Example 136

2-Amino-3-cyano-7-dimethylamino-4-(6-methyl-3-pyridyl)-4H-chromene

The title compound was prepared as a tan solid by a procedure similar to that described in Example 128. $^1$H NMR (DMSO-d$_6$): 8.25 (s, 1H), 7.39–7.18 (m, 2H), 6.85 (s, 2H), 6.75 (d, J=8.4, 1H), 6.46–6.43 (m, 1H), 6.26 (s, 1H), 4.63 (s, 1H), 2.83 (s, 6H), 2.40 (s, 3H).

Example 137

2-Amino-3-cyano-7-dimethylamino-4-(6-methyl-2-pyridyl)-4H-chromene

The title compound was prepared as a tan solid by a procedure similar to that described in Example 1 in 66% yield. $^1$H NMR (CDCl$_3$): 7.49 (t, J=7.5, 1H), 7.00–6.93 (m, 3H), 6.43–6.39 (m, 1H), 6.28 (s, 1H), 4.84 (s, 1H), 4.66 (s, 2H), 2.91 (s, 6H), 2.56 (s, 3H).

Example 138

2-Amino-3-cyano-7-dimethylamino-4-(2-bromo-4,5-methylenedioxyphenyl)-4H-chromene The title compound was prepared as a yellow solid by a procedure similar to that described in Example 1 in 9% yield. $^1$H NMR (DMSO-d$_6$): 7.16 (s, 1H), 6.88 (s, 1H), 6.72 (d, J=9.0, 1H), 6.56 (s, 1H), 6.46 (dd, J=2.1, 9.0, 1H), 6.2 (d, J=2.1, 1H). 6.05 (s, 1H), 6.01 (s, 1H), 5.06 (s, 1H), 2.86 (s, 6H).

Example 139

2-Amino-3-cyano-4-(3-bromo-4,5-dimethoxyphenyl)-4H-naphtho[2,1-b]pyran

The title compound was prepared as a yellow solid by a procedure similar to that described in Example 1 in 1% yield. $^1$H NMR (DMSO-d$_6$): 7.98–7.89 (m, 3H), 7.53–7.43 (m, 2H), 7.35 (d, J=9.3, 1H), 7.08–7.06 (m, 3H), 6.76 (m, 1H), 5.34 (s, 1H), 7.35 (s, 3H), 3.66 (s, 3H), 2.50 (s, 6H).

Example 140

2-Amino-3-cyano-7-dimethylamino-4-(4-chloro-2-nitrophenyl)-4H-chromene

The title compound was prepared as a yellow solid by a procedure similar to that described in Example 1 in 5% yield. $^1$H NMR (DMSO-d$_6$): 8.03 (d, J=2.1, 1H), 7.72 (dd, J=2.1, 8.7, 1H), 7.30 (d, J=8.7, 1H), 7.03 (s, 2H), 6.75 (d, J=8.7, 1H), 6.48 (dd, J=2.1, 8.7, 1H), 6.24 (d, J=2.1, 1H), 5.08 (s, 1H), 2.88 (s, 6H).

Example 141

2-Amino-3-cyano-4-(3-bromo-4,5-dimethoxyphenyl)-4H-quino[5,6-b]pyran

To a mixture of 5-bromoveratraldehyde (245 mg, 1 mmol) and malononitrile (66 mg, 1 mmol) in ethanol (2 ml) was added piperidine (0.1 ml, 1 mmol). The mixture was stirred at room temperature for 15 min, then refluxed for 1 h, and cooled to room temperature. To the mixture was added piperidine (0.1 ml, 1 mmol) and 5-hydroxyquinoline (145 mg, 1 mmol). The mixture was refluxed for 1 h, and the solvent was evaporated. The residue was purified by chromatography on silica gel (EtOAc/hexane, 1:2), yielding the title compound (50 mg, 11%). $^1$H NMR (CDCl$_3$): 8.95 (s, 1H), 8.50 (d, J=9.0, 1H), 7.82 (d, J=9.0, 1H), 7.50 (brs, 1H), 7.30 (s, 1H), 6.92 (s, 1H), 6.76 (s, 1H), 4.82 (brs, 3H), 3.84 (s, 6H).

Example 142

2-Amino-3-cyano-4-(3-bromo-4,5-dimethoxyphenyl)-4H-isoquino-[5,6-b]pyran

The title compound was prepared from 5-hydroxyisoquinoline by a procedure similar to that described for Example 141. $^1$H NMR (CDCl$_3$): 9.23 (s, 1H), 8.66 (d, J=6.0, 1H), 7.95 (d, J=5.7, 1H), 7.69 (d, J=8.4, 1H), 7.18 (d, J=8.7, 1H), 6.92 (d, J=1.8, 1H), 6.75 (d, J=1.8, 1H), 4.85 (m, 3H), 3.84 (s, 6H).

Example 143

2-Amino-3-cyano-4-(3-bromo-4,5-dimethoxyphenyl)-4H-quino[8,7-b]pyran

The title compound was prepared from 8-hydroxyquinoline by a procedure similar to that described for Example 141. $^1$H NMR (CDCl$_3$): 9.01 (m, 1H), 8.17 (m, 1H), 7.55–7.50 (m, 2H), 7.15 (d, J=8.7, 1H), 6.98 (d, J=2.0, 1H), 6.76 (d, J=1.8, 1H), 5.07 (s, 2H), 4.86 (s, 1H), 3.83 (s, 6H).

Example 144

2-Amino-3-cyano-7-ethoxy-4-(3-bromo-4,5-dimethoxyphenyl)-4H-chromene

To a mixture of 5-bromoveratraldehyde (245 mg, 1 mmol) and malononitrile (66 mg, 1 mmol) in ethanol (2 ml) was added piperidine (0.1 ml, 1 mmol). The mixture was stirred at room temperature for 15 min, then 3-ethoxyphenol (138 mg, 1 mmol) was added and it was stirred overnight. The solvent was evaporated and the residue was purified by chromatography on silica gel (EtOAc/Hexane, 1:2) to yield the title compound. $^1$H NMR (CDCl$_3$): 6.84–6.82 (m, 2H), 6.70 (s, 1H), 6.61–6.65 (m, 1H), 6.53 (s, 1H), 4.62 (m, 3H), 4.0 (q, J=6.0, 2H), 3.82 (s, 6H), 1.4 (t, J=6.0, 3H).

Example 145

2-Amino-3-cyano-4-(3-bromo-4,5-dimethoxyphenyl)-7,8,9,10-tetrahydro-4H-naphtho[1,2-b]pyran Step 1: To a mixture of 5-bromoveratraldehyde (245 mg, 1 mmol) and malononitrile (66 mg, 1 mmol) in ethanol was added piperidine (0.1 ml, 1 mmol). The mixture was stirred at room temperature for 15 min to give the product 3,4-dimethoxy-5-bromobenzylidenemalononitrile as a yellow precipitate.

Step 2: To a stirred suspension of 3,4-dimethoxy-5-bromobenzylidenemalononitrile (293 mg, 1 mmol) and 5,6,7,8-Tetrahydro-1-naphthol (148 mg, 1 mmol) in ethanol (4 ml) was added piperidine (0.1 ml, 1 mmol), and the mixture was refluxed for 2 h. The solvent was evaporated and the residue was purified by column chromatography (EtOAc/Hexane, 1:2), yielding the title compound (6 mg, 1.4%). $^1$H NMR (CDCl$_3$): 7.89 (d, J=2.0, 1H), 6.80–6.69 (m, 3H), 4.63 (s, 3H), 3.86 (s, 3H), 3.83 (s, 3H), 2.72 (m, 4H), 1.8 (m, 4H).

Example 146

2-Amino-3-cyano-4-(3-bromo-4,5-dimethoxyphenyl)-7,8-Dimethyl-4H-chromene

The title compound was prepared from 2,3-dimethylphenol by a procedure similar to that described for Example 145. $^1$H NMR (CDCl$_3$): 6.87 (m, 2H), 6.71 (m, 2H), 4.64 (brs, 3H), 3.85–3.82 (m, 6H), 2.26 (s, 3H), 2.22 (s, 3H).

Example 147

2-Amino-3-cyano-4-(3,4,5-trimethoxyphenyl)-4H-quino[5,6-b]pyran

The title compound was prepared from 3,4,5-trimethoxybenzylidenemalononitrile (244 mg, 1 mmol) and 5-hydroxyquinoline by a procedure similar to that described for Example 145. $^1$H NMR (CDCl$_3$): 8.96 (m, 1H), 8.52 (d, J=8.7, 1H), 7.82 (d, J=9.0, 1H), 7.52 (m, 1H), 7.33 (d, J=8.7, 1H), 6.43 (s, 2H), 4.83 (m, 3H), 3.83 (s, 3H), 3.80 (s, 3H).

Example 148

Identification of 2-Amino-3-cyano-7-dimethylamino-4-(3-methoxy-4,5-methylenedioxyphenyl)-4H-chromene and Analogs as Caspase Cascade Activators and Inducers of Apoptosis in Solid Tumor Cells Human breast cancer cell lines T47D and ZR-75-1 were grown according to media component mixtures designated by American Type Culture Collection +10% FCS (Life Technologies, Inc.), in a 5% CO$_2$-95% humidity incubator at 37° C. T-47D and ZR-75-1 cells were maintained at a cell density between 30 and 80% confluency at a cell density of 0.1 to 0.6×10$^6$ cells/ml. Cells were harvested at 600×g and resuspended at 0.65×10$^6$ cells/ml into appropriate media +10% FCS. An aliquot of 45 µl of cells was added to a well of a 96-well microtiter plate containing 5 µl of a 10% DMSO in RPMI-1640 media solution containing 0.16 to 10 µl of 2-amino-3-cyano-7-dimethylamino-4-(3-methoxy-4,5-methylenedioxyphenyl)-4H-chromene (Example 19) or other test compound (0.016 to 1 µM final). An aliquot of 45 µl of cells was added to a well of a 96-well microtiter plate containing 5 µl of a 10% DMSO in RPMI-1640 media solution without test compound as the control sample. The samples were mixed by agitation and then incubated at 37° C. for 24 h in a 5% CO$_2$-95% humidity incubator. After incubation, the samples were removed from the incubator and 50 µl of a solution containing 20 µM of N-(Ac-DEVD)-N'-ethoxycarbonyl-R110 (SEQ ID NO: 1) fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2, and 500 µg/ml lysolecithin (Calbiochem) was added. The samples were mixed by agitation and incubated at room temperature. Using a fluorescent plate reader (Model 1420 Wallac Instruments), an initial reading (T=0) was made approximately 1–2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU\ (T=0) = \text{Net } RFU_{(T=3h)}$$

The activity of caspase cascade activation was determined by the ratio of the net RFU value for 2-amino-3-cyano-7-dimethylamino-4-(3-methoxy-4,5-methylenedioxyphenyl)-4H-chromene or other test compound to that of control samples. The $EC_{50}$ (nM) was determined by a sigmoidal dose-response calculation (Prism 2.0, GraphPad Software Inc.). The caspase activity (Ratio) potency ($EC_{50}$) are summarized in Table I:

TABLE I

Caspase Activity and Potency

| Example # | T-47D Ratio | T-47D EC50 (nM) | ZR-75-1 Ratio | ZR-75-1 EC50 (nM) |
|---|---|---|---|---|
| 1 | ND | ND | 4.2 | 60 |
| 4 | 6.0 | 200 | 6.6 | 150 |
| 10 | 4.2 | 10 | 5.0 | 9 |
| 14 | 5.5 | 172 | 9.0 | 96 |
| 19 | 5.5 | 87 | 6.3 | 38 |
| 38 | 12.7 | 45 | 6.5 | 22 |
| 39 | 8.4 | 250 | 2.7 | 65 |
| 94 | 6.5 | 49 | 7.8 | 25 |
| 95 | 3.8 | 720 | 5.1 | 364 |
| 96 | Inactive | Inactive | Inactive | Inactive |
| 97 | 2.7 | 6 | 5.0 | 7 |
| 99 | 2.8 | 36 | 4.3 | 23 |
| 103 | 2.2 | 17 | 4.2 | 12 |

Thus, 2-amino-3-cyano-7-dimethylamino-4-(3-methoxy-4,5-methylenedioxyphenyl)-4H-chromene (Example 19) and analogs are identified as potent caspase cascade activators and inducer of apoptosis in solid tumor cells.

Example 149

Identification of 2-Amino-3-cyano-7-dimethylamino-4-(3-methoxy-4,5-methylenedioxyphenyl)-4H-chromene and Analogs as Antineoplastic Compounds that Exhibit Inhibition of Cell Proliferation ($GI_{50}$)

T-47D and ZR-75-1 cells were grown and harvested as in Example 148. An aliquot of 90 µl of cells (2.2×10 cells/ml) was added to a well of a 96-well microtiter plate containing 10 µl of a 10% DMSO in RPMI-1640 media solution containing 1 nM to 100 µM of 2-amino-3-cyano-7-dimethylamino-4-(3-methoxy-4,5-methylenedioxyphenyl)-4H-chromene (Example 19) or other test compound (0.1 nM to 10 µM final). An aliquot of 90 µl of cells was added to a well of a 96-well microtiter plate containing 10 µl of a 10% DMSO in RPMI-1640 media solution without compound as the control sample for maximal cell proliferation ($A_{max}$). The samples were mixed by agitation and then incubated at 37° C. for 48 h in a 5% $CO_2$-95% humidity incubator. After incubation, the samples were removed from the incubator and 20 µl of CellTiter 96 $AQ_{UEOUS}$ One Solution Cell Proliferation™ reagent (Promega) was added. The samples were mixed by agitation and incubated at 37° C. for 2–4 h in a 5% $CO_2$-95% humidity incubator. Using an absorbance plate reader (Model 1420 Wallac Instruments), an initial reading (T=0) was made approximately 1–2 min after addition of the solution, employing absorbance at 490 nm. This determines the possible background absorbance of the test compounds. No absorbance for 2-amino-3-cyano-7-dimethylamino-4-(3-methoxy-4,5-methylenedioxyphenyl)-4H-chromene or its analogs was found at 490 nm. After the 24 h incubation, the samples were read for absorbance as above ($A_{Test}$).

Baseline for $GI_{50}$ (dose for 50% inhibition of cell proliferation) of initial cell numbers were determined by adding an aliquot of 90 µl of cells or 90 µl of media, respectively, to wells of a 96-well microtiter plate containing 10 µl of a 10% DMSO in RPMI-1640 media solution. The samples were mixed by agitation and then incubated at 37° C. for 0.5 h in a 5% $CO_2$-95% humidity incubator. After incubation, the samples were removed from the incubator and 20 µl of CellTiter 96 $AQ_{UEOUS}$ One Solution Cell Proliferation™ reagent (Promega) was added. The samples were mixed by agitation and incubated at 37° C. for 24 h in a 5% $CO_2$-95% humidity incubator. Absorbance was read as above, ($A_{T=0}$) defining absorbance for initial cell number used as baseline in $GI_{50}$ determinations.

Calculation:

$GI_{50}$ (dose for 50% inhibition of cell proliferation)

$$50 = 100 \times [(A_{Test} - A_{T=0})/(A_{max} - A_{T=0})]$$

The $GI_{50}$ (nM) are summarized in Table II:

TABLE II

| | $GI_{50}$ in Cancer Cells | |
|---|---|---|
| Cell lines | Example 19 GI50 (nM) | Example 1 GI50 (nM) |
| T-47D | 3 | 100 |
| ZR-75-1 | 500 | 10000 |

Thus, 2-amino-3-cyano-7-dimethylamino-4-(3-methoxy-4,5-methylenedioxyphenyl)-4H-chromene (Example 19) and 2-amino-3-cyano-7-dimethyl-amino-4-(3,4-methylenedioxyphenyl)-4H-chromene (Example 1) are identified as potent antineoplastic compound that inhibit cell proliferation.

Example 150

Figure 1B:
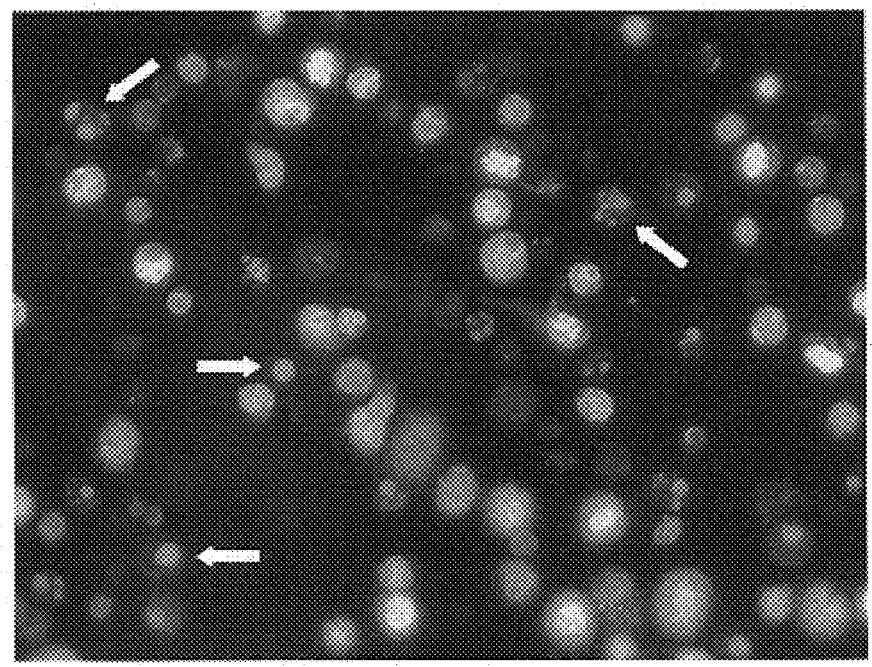

2-Amino-3-cyano-7-dimethylamino-4-(3-methoxy-4,5-methylenedioxyphenyl)-4H-chromene Induces Nuclear Fragmentation in Jurkat Cells The ability of 2-amino-3-cyano-7-dimethylamino-4-(3-methoxy-4,5-methylenedioxyphenyl)-4H-chromene to induce nuclear fragmentation was tested by treatment of Jurkat cells with the test compound followed by staining of the nucleus with Syto16, a fluorescent DNA dye. The nuclei of Jurkat cells treated with DMSO vehicle are round with dispersed chromatin that is moderately stained with Syto16 (FIG. 1A). In contrast, Jurkat cells treated with 100 nM or higher 2-amino-3-cyano-7-dimethylamino-4-(3-methoxy-4,5-methylenedioxyphenyl)-4H-chromene for 24 h have shrunken and fragmented nuclei (FIG. 1B), which is a hallmark of caspase-mediated apoptosis. These results corroborate the caspase induction assays by showing that 2-amino-3-cyano-7-dimethylamino-4-(3-methoxy-4,5-methylenedioxyphenyl)-4H-chromene can induce a key cellular marker of apoptosis.

Example 151

Figure 2:
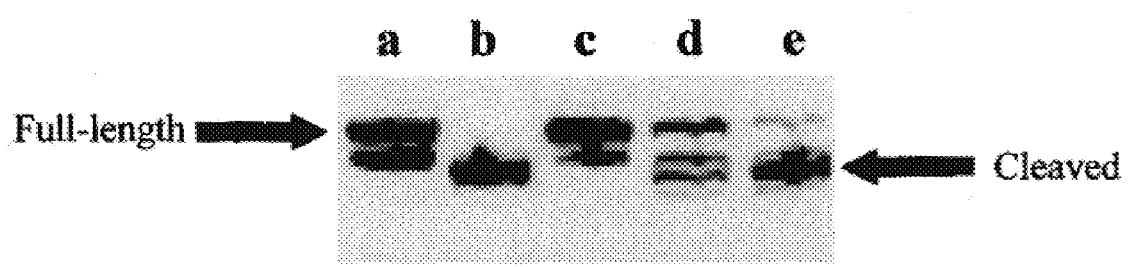
FIGS. 2A–E depict western blots of drug induced poly (ADP)ribose polymerase (PARP) cleavage in Jurkat cells.

2-Amino-3-cyano-7-dimethylamino-4-(3-methoxy-4, 5-methylenedioxyphenyl)-4H-chromene Induces PARP Cleavage in Jurkat Cells A wide range of natural substrates are cleaved by the caspases during apoptosis. One of these is poly(ADP)ribose polymerase (PARP), an enzyme important in genome surveillance. The ability of 2-amino-3-cyano-7-dimethylamino-4-(3-methoxy-4,5-methylenedioxyphenyl)-4H-chromene to induce PARP cleavage was tested by treating Jurkat cells with the compound at a concentration of 2.5 $\mu$M for 5, 15 and 30 h. Control cultures were treated with DMSO vehicle or staurosporine, a known apoptosis inducer. As illustrated in FIG. 2, 2-amino-3-cyano-7-dimethylamino-4-(3-methoxy-4,5-methylenedioxyphenyl)-4H-chromene induced PARP cleavage starting at 15 h, and by 30 h virtually all of PARP was converted into its cleaved form. These results provide additional evidence that 2-amino-3-cyano-7-dimethylamino-4-(3-methoxy-4,5-methylenedioxyphenyl)-4H-chromene induces caspase-mediated apoptosis in intact cultured cells.

Example 152

Figure 3:
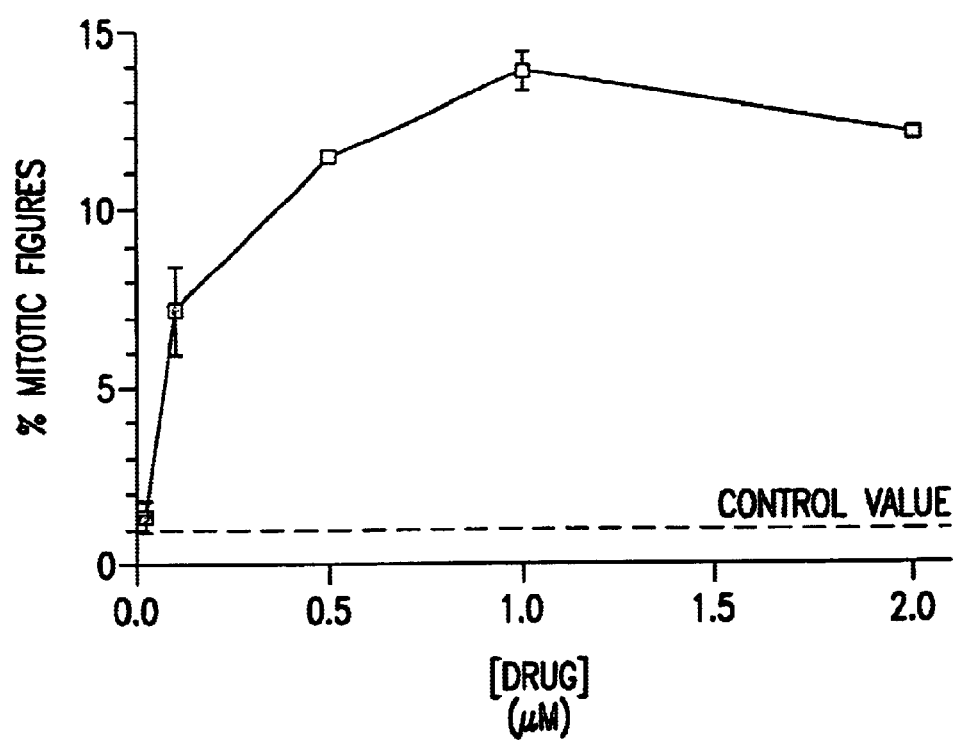
FIG. 3 is a graph showing mitotic arrest in Jurkat cells treated for 6 h with different concentrations of 2-amino-3-cyano-7-dimethylamino-4-(3-methoxy-4,5-methylenedioxyphenyl)-4H-chromene.

2-Amino-3-cyano-7-dimethylamino-4-(3-methoxy-4, 5-methylenedioxyphenyl)-4H-chromene Induces Mitotic Arrest in Jurkat Cells Jurkat cells were incubated with a range of concentrations of 2-amino-3-cyano-7-dimethylamino-4-(3-methoxy-4,5-methylenedioxyphenyl)-4H-chromene (0.02 $\mu$M to 5 $\mu$M) for 6 h under normal growth conditions; control cultures were treated with DMSO vehicle. The cells were then treated for 20 min. with 800 nM Syto 16. Cytospin preparations were then prepared and the samples were viewed by fluorescent microscopy using a fluorescein filter set. For each concentration of test compound, the number of mitotic figures were counted and expressed as a percentage of the total number of cells. Three fields from each condition were evaluated and the mean and SEM were calculated and plotted as a function of drug concentration (FIG. 3). The results show that 2-amino-3-cyano-7-dimethylamino-4-(3-methoxy-4,5-methylenedioxyphenyl)-4H-chromene is an extremely effective inducer of mitotic arrest in Jurkat cells with an $EC_{50}$ of about 125 nM.

Example 153

Figure 4A:
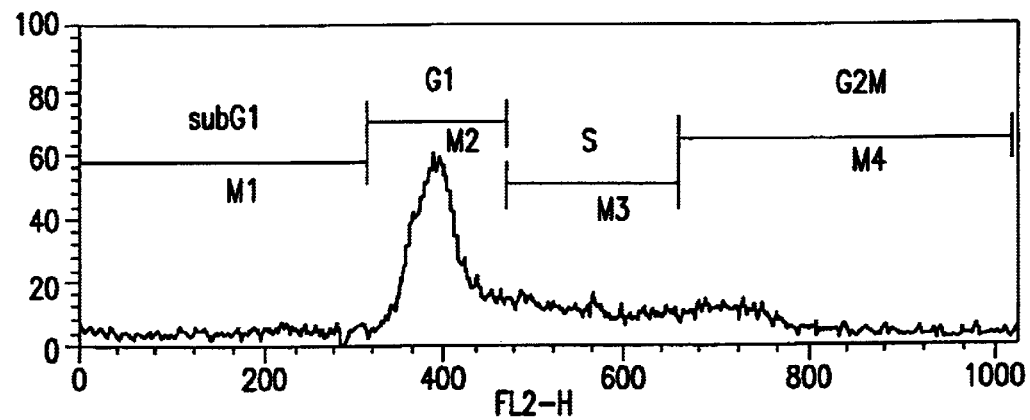
FIGS. 4A–B are graphs showing drug induced cell cycle arrest in Jurkat cells.
Figure 4B:
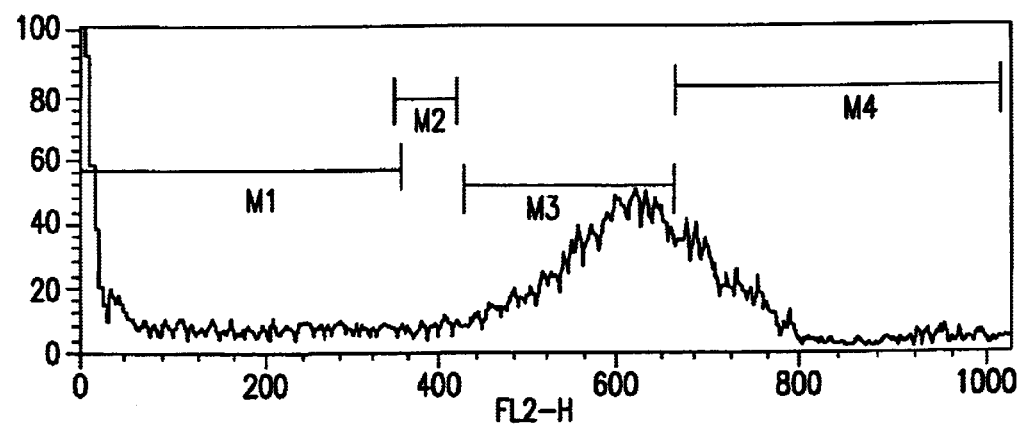
Figure 5A:
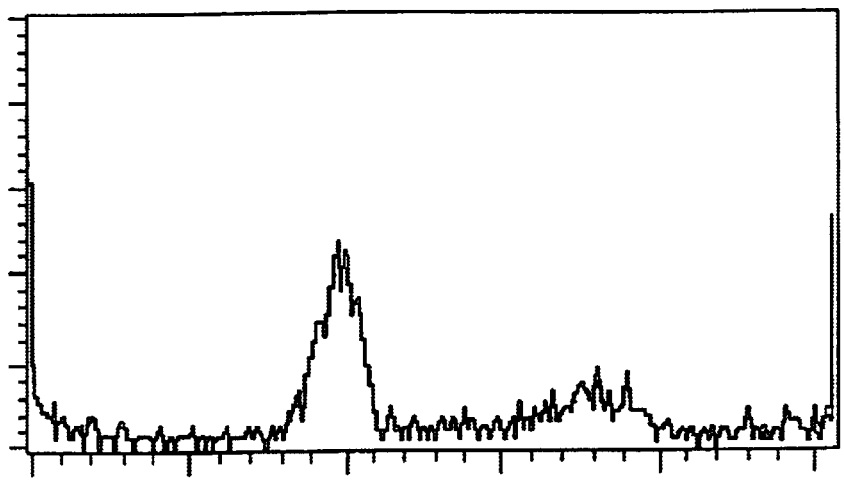
FIGS. 5A–C are graphs showing drug induced cell cycle arrest in T47D cells.
Figure 5B:
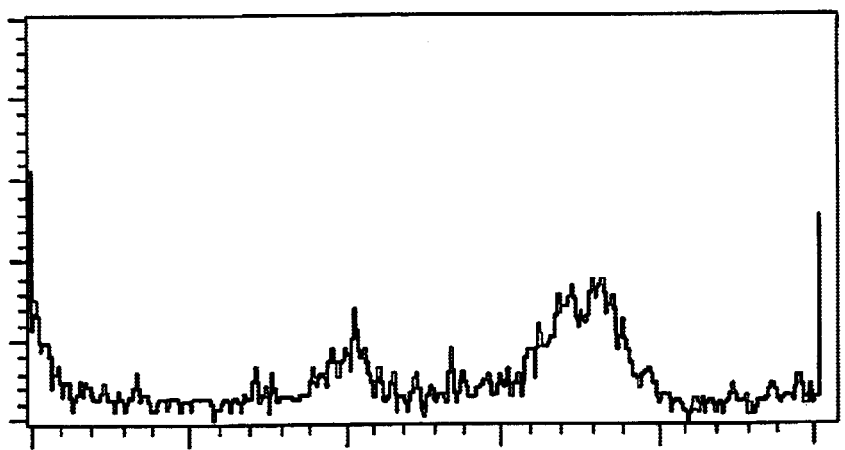
Figure 5C:
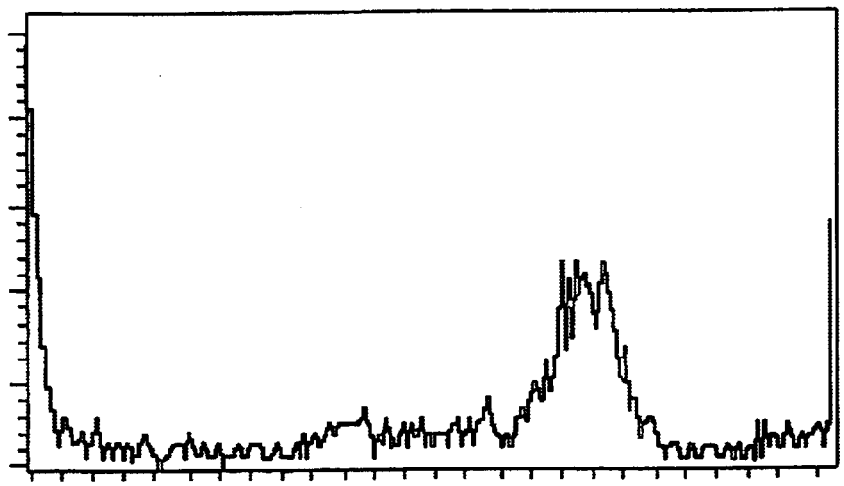
Figure 6A:
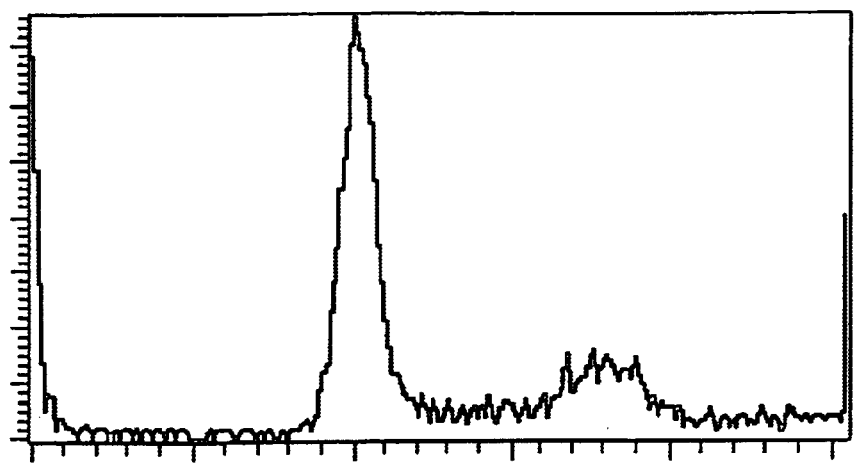
FIGS. 6A–C are graphs showing drug induced cell cycle arrest in PC-3 cells.
Figure 6B:
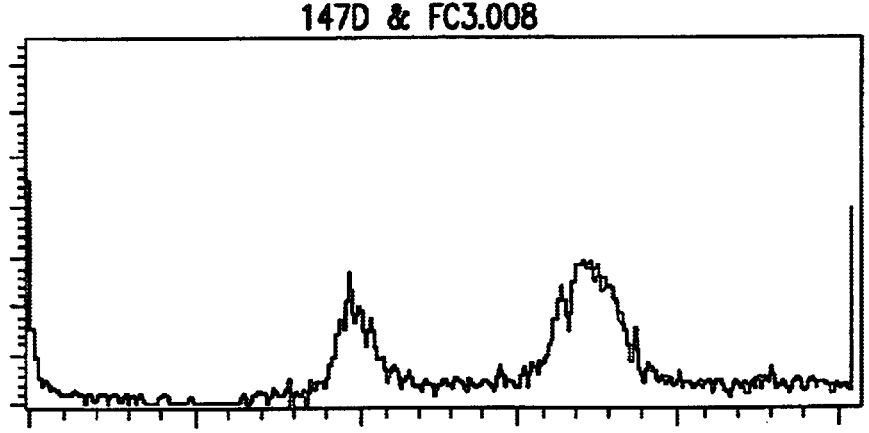
Figure 6C:
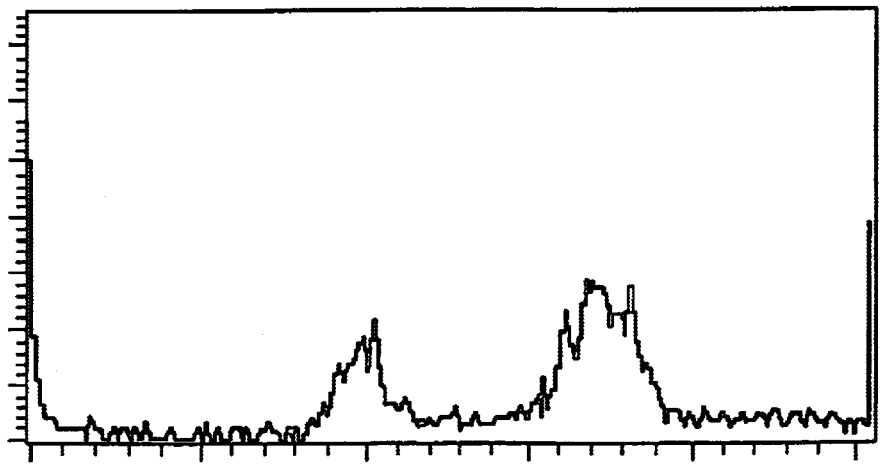

Treatment With 2-Amino-3-cyano-7-dimethylamino-4-(3-methoxy-4,5-methylenedioxyphenyl)-4H-chromene Leads to Cell Cycle Arrest in T Leukemia and Solid Tumor Cell Lines T47D, ZR-75-1 breast cancer cell lines and PC-3, an androgen-independent prostate cancer cell line were maintained and harvested as described in Example 148. Jurkat T leukemia cells were grown in RPMI 1640 media (Life Technologies, Inc.) +10% FCS (Sigma Chemical Company) in a 5% $CO_2$-95% humidity incubator at 37° C., and maintained at a cell density between 4 and $8 \times 10^5$ cells/ml. $1 \times 10^6$ cells were induced with 1 $\mu$M of 2-amino-3-cyano-7-dimethylamino-4-(3-methoxy-4,5-methylenedioxyphenyl)-4H-chromene or 2-amino-3-cyano-7-dimethylamino-4-(3,4-methylenedioxyphenyl)-4H-chromene for 18 h at 37° C. As a control, cells were also incubated with DMSO. Cells were harvested at 1200 rpm and washed twice with 5 mM EDTA/PBS. Cells were then resuspended in 300 $\mu$l EDTA/PBS and 700 ml of 100% ethanol, vortexed and incubated at room temperature for 1 h. Samples were spun down at 12000 rpm for 5 min and the supernatant was removed. A solution containing 100 $\mu$g/ml of propidium iodide and 1 mg/ml of RNAse A (fresh) was added to the samples and incubated for 1 h at room temperature. Samples were then transferred to 12×75 mm polystyrene tubes and analysed on a flow cytometer. All flow cytometry analyses were performed on FACScalibur (Becton Dickinson) using Cell Quest analysis software. FIGS. 4A–B show that 2-amino-3-cyano-7-dimethylamino-4-(3-methoxy-4,5-methylenedioxyphenyl)-4H-chromene induces cell cycle arrest in Jurkat cells. FIGS. 5A–C show that 2-amino-3-cyano-7-dimethylamino-4-(3-methoxy-4,5-methylenedioxyphenyl)-4H-chromene and 2-amino-3-cyano-7-dimethylamino-4-(3,4-methylenedioxyphenyl)-4H-chromene induce cell cycle arrest in T47D Cells. FIGS. 6A–C show that 2-amino-3-cyano-7-dimethylamino-4-(3-methoxy-4,5-methylenedioxyphenyl)-4H-chromene and 2-amino-3-cyano-7-dimethylamino-4-(3,4-methylenedioxyphenyl)-4H-chromene induce cell cycle arrest in PC-3 cells.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

---

What is claimed is:

1. A pharmaceutical composition comprising a pharmaceutically acceptable excipient or carrier and a compound of Formula I:

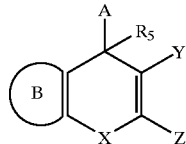

(I)

or a pharmaceutically acceptable salt or prodrug thereof, wherein:
X is O;
Y is CN;
Z is $NR_8R_9$ wherein $R_8$ and $R_9$ are independently H or $C_{1-4}$ alkyl;
$R_5$ is hydrogen or $C_{1-10}$ alkyl;
A is optionally substituted $C_{6-14}$ aryl; and
B is an optionally substituted indolo ring.

2. The pharmaceutical composition of claim 1, wherein A is optionally substituted phenyl.

3. The pharmaceutical composition of claim 1, wherein X is O, Y is CN and Z is $NH_2$.

4. The pharmaceutical composition of claim 1, wherein $R_5$ is hydrogen.

5. The pharmaceutical composition of claim 1, comprising a pharmaceutically acceptable excipient or carrier and a compound of Formula II:

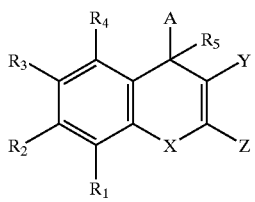

(II)

or a pharmaceutically acceptable salt or prodrug thereof, wherein:
$R_3$–$R_4$ are independently hydrogen, halo, haloalkyl, aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; $R_1$ and $R_2$, taken together with the atoms to which they are attached form a pyrrolo group, wherein said group is optionally substituted;
wherein the aryl portion of said arylalkyl, the aryl portion of said arylalkenyl and the aryl portion of said arylalkynyl are each independently $C_{6-14}$ aryl; and
said carbocyclic is $C_{3-8}$ cycloalkyl or $C_{3-8}$ cycloalkenyl.

6. The pharmaceutical composition of claim 5, wherein $R_1$ and $R_2$, are taken together to form a structure —CH=CH—N(R)—, wherein R is hydrogen, $C_{1-10}$ alkyl, haloalkyl, aryl, fused aryl, carbocyclic, alkenyl, alkynyl, arylalkyl, arylalkenyl, arylalkynyl, carbocycloalkyl, heterocycloalkyl, hydroxyalkyl or aminoalkyl.

7. The pharmaceutical composition of claim 5, wherein Z is $NH_2$.

8. The pharmaceutical composition of claim 5, wherein $R_5$ is hydrogen.

9. The pharmaceutical composition of claim 5, comprising said compound or a pharmaceutically acceptable salt or prodrug thereof, wherein said optionally substituted $C_{6-14}$ aryl is

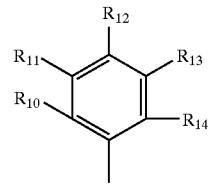

and
(a) $R_{10}$–$R_{14}$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or
(b) $R_{10}$ and $R_{11}$, or $R_{11}$ and $R_{12}$, taken together with the atoms to which they are attached form a fused portion of said optionally substituted $C_{6-14}$ aryl, wherein said fused portion is optionally substituted.

10. The pharmaceutical composition of claim 9, wherein $R_1$ and $R_2$, are taken together to form a structure —CH=CH—N(R)—, wherein R is hydrogen, $C_{1-10}$ alkyl, haloalkyl, aryl, fused aryl, carbocyclic, alkenyl, alkynyl, arylalkyl, arylalkenyl, arylalkynyl, carbocycloalkyl, heterocycloalkyl, hydroxyalkyl or aminoalkyl.

11. The pharmaceutical composition of claim 10, wherein $R_3$, $R_4$ and $R_5$ are each hydrogen.

12. A pharmaceutical composition comprising a pharmaceutically acceptable excipient or carrier and a compound selected from the group consisting of:
2-Amino-3-cyano-4-(3-methoxy-4,5-methylenedioxyphenyl)-4H-indolo[4,5-b]pyran;
2-Amino-3-cyano-4-(2-bromo-4,5-dimethoxyphenyl)-4H-indolo[4,5-b]pyran;
2-Amino-3-cyano-4-(3-bromo-4,5-dimethoxyphenyl)-4H-indolo[4,5-b]pyran;
2-Amino-3-cyano-4-(3-bromo-4,5-dimethoxyphenyl)-8-methyl-4H-indolo[4,5-b]pyran;
2-Amino-3-cyano-4-(3,4,5-trimethoxyphenyl)-4H-indolo[4,5-b]pyran;
2-Amino-3-cyano-4-(3-nitrophenyl)-4H-indolo[4,5-b]pyran;
2-Amino-3-cyano-4-(3-cyanophenyl)-4H-indolo[4,5-b]pyran;
2-Amino-3-cyano-4-(3,5-dimethoxyphenyl)-4H-indolo[4,5-b]pyran; and
9-Acetamide-2-amino-3-cyano-4-(3-bromo-4,5-dimethoxyphenyl)-4H-indolo[4,5-b]pyran.

13. The pharmaceutical composition of claim 1, wherein said excipient or carrier is selected from the group consisting of saccharides, starch pastes, gelatin, tragacanth, cellulose preparations, calcium phosphates and polyvinyl pyrrolidone.

14. The pharmaceutical composition of claim 15, wherein said excipient or carrier is a saccharide selected from the group consisting of lactose, sucrose, manitol and sorbitol.

15. The pharmaceutical composition of claim 1, wherein said excipient or carrier is a lipophilic solvent.

16. The pharmaceutical composition of claim 17, wherein said lipophilic solvent is selected from the group consisting of fatty oils, fatty acid esters, polyethylene glycols and paraffin hydrocarbons.

17. The pharmaceutical composition of claim 18, wherein said lipophilic solvent is selected from the group consisting of sesame oil, ethyl oleate, triglycerides, polyethylene glycol-400, cremophor and cyclodextrins.

18. The pharmaceutical composition of claim 1, wherein said excipient or carrier is selected from the group consisting of vegetable oils, mineral oils, white petrolatum, branched chain fats, branched chain oils, animal fats and high molecular weight alcohol (greater than $C_{12}$).

19. The pharmaceutical composition of claim 1, wherein said excipient or carrier is a saline solution.

20. A compound of Formula I:

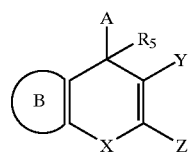

(I)

or a pharmaceutically acceptable salt or prodrug thereof, wherein:

B is optionally substituted indolo;

X is O;

Y is CN;

Z is $NR_8R_9$, wherein $R_8$ and $R_9$ are independently H or $C_{1-4}$alkyl;

$R_5$ is hydrogen or $C_{1-10}$ alkyl; and

A is optionally substituted $C_{6-14}$ aryl.

21. The compound of claim 22, wherein said compound is an optionally substituted 4H-indolo[4,5-b]pyran.

22. The compound of claim 23, wherein A is optionally substituted phenyl.

23. A compound selected from the group consisting of:

2-Amino-3-cyano-4-(3-methoxy-4,5-methylenedioxyphenyl)-4H-indolo[4,5-b]pyran;

2-Amino-3-cyano-4-(2-bromo-4,5-dimethoxyphenyl)-4H-indolo[4,5-b]pyran;

2-Amino-3-cyano-4-(3-bromo-4,5-dimethoxyphenyl)-4H-indolo[4,5-b]pyran;

2-Amino-3-cyano-4-(3-bromo-4,5-dimethoxyphenyl)-8-methyl-4H-indolo[4,5-b]pyran;

2-Amino-3-cyano-4-(3,4,5-trimethoxyphenyl)-4H-indolo[4,5-b]pyran;

2-Amino-3-cyano-4-(3-nitrophenyl)-4H-indolo[4,5-b]pyran;

2-Amino-3-cyano-4-(3-cyanophenyl)-4H-indolo[4,5-b]pyran;

2-Amino-3-cyano-4-(3,5-dimethoxyphenyl)-4H-indolo[4,5-b]pyran; and

9-Acetamide-2-amino-3-cyano-4-(3-bromo-4,5-dimethoxyphenyl)-4H-indolo[4,5-b]pyran.

24. The pharmaceutical composition of claim 1, wherein said aryl is selected from the group consisting of phenyl, naphthyl, phenanthrenyl, anthracenyl, indenyl, azulenyl, biphenyl, biphenylenyl and fluorenyl.

25. The compound of claim 20, wherein said aryl is selected from the group consisting of phenyl, naphthyl, phenanthrenyl, anthracenyl, indenyl, azulenyl, biphenyl, biphenylenyl and fluorenyl.

26. The pharmaceutical composition of claim 1, wherein said aryl is phenyl.

27. The compound of claim 20, wherein said aryl is phenyl.

* * * * *